US010426790B2

(12) United States Patent
Young et al.

(10) Patent No.: US 10,426,790 B2
(45) Date of Patent: Oct. 1, 2019

(54) TREATMENT OF ALLERGIC EYE CONDITIONS WITH CYCLODEXTRINS

(71) Applicant: Aldeyra Therapeutics, Inc., Lexington, MA (US)

(72) Inventors: Scott Young, E. Falmouth, MA (US); Todd Brady, Carlisle, MA (US); Stephen Gitu Machatha, Burlington, MA (US); David Clark, Winchester, MA (US); Susan Macdonald, Danvers, MA (US)

(73) Assignee: Aldeyra Therapeutics, Inc., Lexington, MA (US)

( * ) Notice: Subject to any disclaimer, the term of this patent is extended or adjusted under 35 U.S.C. 154(b) by 0 days.

(21) Appl. No.: 15/445,802

(22) Filed: Feb. 28, 2017

(65) Prior Publication Data

US 2017/0266220 A1    Sep. 21, 2017

Related U.S. Application Data

(60) Provisional application No. 62/300,907, filed on Feb. 28, 2016, provisional application No. 62/315,488, filed on Mar. 30, 2016.

(51) Int. Cl.
| | | |
|---|---|---|
| *A61F 9/00* | (2006.01) | |
| *A61K 9/00* | (2006.01) | |
| *A61K 9/08* | (2006.01) | |
| *C08L 5/16* | (2006.01) | |
| *A61K 31/724* | (2006.01) | |
| *C08B 37/16* | (2006.01) | |

(52) U.S. Cl.
CPC .......... *A61K 31/724* (2013.01); *A61F 9/0008* (2013.01); *A61K 9/0048* (2013.01); *A61K 9/08* (2013.01); *C08B 37/0015* (2013.01); *C08L 5/16* (2013.01)

(58) Field of Classification Search
None
See application file for complete search history.

(56) References Cited

U.S. PATENT DOCUMENTS

| | | | |
|---|---|---|---|
| 4,956,351 A | 9/1990 | Mesens et al. | |
| 5,024,998 A | 6/1991 | Bodor | |
| 5,364,637 A | 11/1994 | De et al. | |
| 5,376,645 A | 12/1994 | Stella et al. | |
| 5,419,898 A | 5/1995 | Ikejiri et al. | |
| 5,472,954 A | 12/1995 | Loftsson | |
| 5,576,311 A | 11/1996 | Guy | |
| 5,767,109 A | 6/1998 | Sanchez et al. | |
| 5,998,488 A | 12/1999 | Shinohara et al. | |
| 7,083,803 B2 | 8/2006 | Peyman | |
| 7,982,071 B2 | 7/2011 | Scott et al. | |
| 8,158,609 B1 | 4/2012 | Marsh et al. | |
| 8,791,154 B2 | 7/2014 | Gamache et al. | |
| 9,265,759 B2 | 2/2016 | Jordan et al. | |
| 9,364,471 B2 | 6/2016 | Jordan et al. | |
| 9,604,997 B2 | 3/2017 | Jordan | |
| 9,814,701 B2 | 11/2017 | Jordan et al. | |
| 10,111,862 B2 | 10/2018 | Chabala et al. | |
| 10,202,348 B2 | 2/2019 | Jordan et al. | |
| 10,213,395 B2 | 2/2019 | Brady et al. | |
| 2004/0198828 A1 | 10/2004 | Abelson et al. | |
| 2005/0130906 A1 | 6/2005 | Matier et al. | |
| 2005/0197292 A1 | 9/2005 | Smithson et al. | |
| 2005/0234018 A1 | 10/2005 | Lyons et al. | |
| 2006/0111318 A1 | 5/2006 | Okamoto | |
| 2009/0118503 A1 | 5/2009 | Sprott et al. | |
| 2010/0240624 A1 | 9/2010 | Chapin et al. | |
| 2012/0108585 A1 | 5/2012 | Vu | |
| 2012/0295967 A1* | 11/2012 | Gamache ............. | A61K 9/0048 514/450 |
| 2012/0302601 A1 | 11/2012 | Jordan et al. | |
| 2013/0165419 A1 | 6/2013 | Lindstrom et al. | |
| 2014/0038918 A1 | 2/2014 | Rodriguez-Boulan et al. | |
| 2015/0258120 A1 | 9/2015 | Zarnitsyn et al. | |
| 2015/0335632 A1 | 11/2015 | Brady et al. | |
| 2015/0344432 A1 | 12/2015 | Jordan et al. | |
| 2015/0344447 A1 | 12/2015 | Chabala et al. | |
| 2017/0239196 A1 | 8/2017 | Brady et al. | |
| 2018/0050989 A1 | 2/2018 | MacHatha et al. | |
| 2018/0092882 A1 | 4/2018 | Jordan et al. | |
| 2018/0250306 A1 | 9/2018 | Brady et al. | |
| 2018/0265474 A1 | 9/2018 | Buist et al. | |
| 2018/0354905 A1 | 12/2018 | Brady et al. | |

FOREIGN PATENT DOCUMENTS

| | | |
|---|---|---|
| EP | 1621199 A1 | 1/2006 |
| EP | 2301549 A1 | 3/2011 |
| JP | 2002-003364 A | 1/2002 |
| JP | 3736916 | 1/2006 |
| JP | 2007532648 A | 11/2007 |
| JP | 4466875 B2 | 5/2010 |

(Continued)

OTHER PUBLICATIONS

La Rosa, Italian Journal of Pediatrics 2013, 39:18.*
Abelson et al., "Conjunctival allergen challenge. A clinical approach to studying allergic conjunctivitis," Archives of Ophthalmology, vol. 108, No. 1, Jan. 1990 (pp. 84-88).
Abelson et al., "Combined analysis of two studies using the conjunctival allergen challenge model to evaluate olopatadine hydrochloride, a new ophthalmic antiallergic agent with dual activity," American Journal of Ophthalmology, vol. 125, No. 6, Jun. 1998 (pp. 797-804).
Abelson et al., "Conjunctival allergen challenge: models in the investigation of ocular allergy," Current Allergy and Asthma Reports, vol. 3, No. 4, Jul. 2003 (pp. 363-368).
Berge et al., "Pharmaceutical salts," The Journal of Pharmaceuticals Sciences, vol. 66. No. 1, Jan. 1977 (pp. 1-19).
Bousquet et al., "How to Design and Evaluate Randomized Controlled Trials in Immunotherapy for Allergic Rhinitis: An ARIA-GA2 LEN Statement," Allergy, vol. 66, No. 6, Apr. 2011 (pp. 765-774).

(Continued)

*Primary Examiner* — Layla D Berry
(74) *Attorney, Agent, or Firm* — Andrea L. C. Reid; Dechert LLP

(57) ABSTRACT

The present disclosure provides methods of treating eye allergies and allergic conjunctivitis with cyclodextrin. Ophthalmic compositions of cyclodextrin for topical administration are also provided.

30 Claims, 10 Drawing Sheets

(56) References Cited

FOREIGN PATENT DOCUMENTS

| | | |
|---|---|---|
| JP | 4748289 B2 | 8/2011 |
| JP | 5194218 B2 | 5/2013 |
| WO | WO 2017035077 A1 | 3/1920 |
| WO | WO 2017035082 A1 | 3/1920 |
| WO | WO 2004082622 A2 | 9/2004 |
| WO | WO 2004091630 A1 | 10/2004 |
| WO | WO 2005105067 A2 | 11/2005 |
| WO | WO2006127945 | 11/2006 |
| WO | WO2011072141 | 6/2011 |
| WO | WO2014100425 | 6/2014 |
| WO | WO2014116593 | 7/2014 |
| WO | WO2014116836 | 7/2014 |
| WO | WO 2017196881 A1 | 11/2017 |
| WO | WO 2018039192 A1 | 3/2018 |
| WO | WO 2018039197 A1 | 3/2018 |
| WO | WO 2018170476 A1 | 9/2018 |

OTHER PUBLICATIONS

Bozkir et al., "Effect of hydroxypropyl-beta-cyclodextrin on the solubility, stability and in-vitro release of ciprofloxacin for ocular drug delivery," Acta Poloniae Pharmaceutica, vol. 69, No. 4, Jul. 2012 (pp. 719-724).

Bragagni et al., "Cyclodextrin complexation highly enhances efficacy of arylsulfonylureido benzenesulfonamide carbonic anhydrase inhibitors as a topical antiglaucoma agents," Bioorganic & Medicinal Chemistry, vol. 23, No. 18, Sep. 2015 (pp. 6223-6227).

Brozek et al., "Grading quality of evidence and strength of recommendations in clinical practice guidelines: Part 2 of 3. The GRADE approach to grading quality of evidence about diagonstic tests and strategies," Allergy, vol. 64, No. 8, Aug. 2009 (pp. 1109-1116)

Canonica et al., "Recommendations for standardization of clinical trials with Allergen Specific Immunotherapy for respiratory allergy. A statement of a World Allergy Organization (WAO) taskforce," Allergy, vol. 62, vol. 3, Mar. 2007 (pp. 317-324)

Canonica et al., "Sub-lingual immunotherapy: World Allergy Organization Position Paper 2009," Allergy, vol. 64, Suppl 91, Dec. 2009 (pp. 1-59).

ClinicalTrials.gov identifier NCT02578914, *A Safety and Activity Study of NS2 in Subjects with Allergic Conjunctivitis*, first received date Oct. 8, 2015; https://clinicaltrials.gov/ct2/show/NCT02578914. Clinical Trials Results for Outcome Measures of Ocular Itching and Ocular Tearing (2016).

Everest-Todd, "Topical Application of Cyclodextrin Ethers in the Control of Pain," Proceedings of the Eighth International Symposium on Cyclodextrins, No Month Listed 1998 (pp. 495-498).

International Search Report and Written Opinion issued by the United States Patent and Trademark Office as International Searching Authority for International Patent Application No. PCT/US2017/020020 dated May 24, 2017 (12 pages).

Jóhannsdóttir et al., "Development of a Cyclodextrin-Based Aqueous Cyclosporin a Eye Drop Formulations," International Journal of Pharmaceutics, vol. 493, No. 1-2, Sep. 2015 (pp. 86-95).

Johnson et al., "2-Hydroxypropyl-β-Cyclodextrin Removes All-Trans Retinol from Frog Rod Photoreceptors in a Concentration-Dependent Manner," Journal of Ocular Pharmacology and Therapeutics, vol. 26, No. 3, Sep. 2010 (pp. 245-248).

Kam et al., "Topical Cyclodextrin Reduces Amyloid Beta and Inflammation Improving Retinal Function in Ageing Mice," Experimental Eye Research, vol. 135, Jun. 2015 (pp. 59-66).

Leonardi et al., "Correlation Between Conjunctival Provocation Test (CPT) and Systemic Allergometric Tests in Allergic Conjunctivitis," Eye, vol. 4, 1990 (pp. 760-764).

Loftsson et al., "Cyclodextrins in Eye Drop Formulations: Enhances Topical Delivery of Corticosteroids to the Eye," Acta Ophthalmologica Scandinavica, vol. 80, No. 2, Apr. 2002 (pp. 144-150).

Loftsson et al., "Cyclodextrin Microparticles for Drug Delivery to the Posterior Segment of the Eye: Aqueous Dexamethasone Eye Drops," Journal of Pharmacy and Pharmacology, vol. 59, No. 5, May 2007 (pp. 629-635).

McLaurin et al., "Phase 3 Randomized Double-Masked Study of Efficacy and Safety of Once-Daily 0.77% Olopatadine Hydrochloride Ophthalmic Solution in Subjects with Allergic Conjunctivitis Using the Conjunctival Allergen Challenge Model," clinical Science.

No Author, Highlights of Prescribing Information, Bridion® (sugammadex) Injection, for intravenous use Initial U.S. Approval: 2015, Last Revised Dec. 2015 (19 pages).

Nociari et al., "Beta cyclodextrins bind, stabilize, and remove lipofuscin bisretinoids from retinal pigment epithelium," Proceedings of the National Academy of Science of the United States of America, E1402-E1408, Mar. 2014 (7 pages).

Pontikis et al., "Cyclodextrin alleviates neuronal storage of cholesterol in Niemann-Pick C disease without evidence of detectable blood-brain barrier permeability," Journal of Inherited Metabolic Disease, vol. 36, No. 3, May 2013 (pp. 491-498).

Torkildsen et al., "Efficacy and safety of olopatadine hydrochloride 0.77% in patients with allergic conjunctivitis using a conjunctival allergen-challenge model," Clinical Ophthalmology, vol. 9, Sep. 2015 (pp. 1703-1713).

Knapp et al., "Intraocular Availability of Topically Applied Mycophenolate Mofetil in Rabbits," J. Ocul. Pharmacol. Ther. 19(2), pp. 181-192 (2003).

Aldeyra Press Release Phase II Allergic Conjunctivitis, Feb. 29, 2016 (3 pages).

Aldeyra Press Release—Positive Results From Phase II Clinical Trial in Subjects With Noninfectious Anterior Uveitis, May 9, 2016 (4 pages).

Ao et al., "Methyl-β-Cyclodextrin Impairs the Monocyte-Adhering Ability of Endothelial Cells by Down-Regulating Adhesion Molecules and Caveolae and Reorganizing the Actin Cytoskeleton," Biol Pharm Bull, 39(6):1029-1034 (2016).

Ashton et al., "Location of penetration and metabolic barriers to levobunolol in the corneal epithelium of the pigmented rabbit," The Journal of Pharmacology and Experimental Therapeutics, 259(2):719-724 (1991).

Augustin et al., "Oxidative reactions in the tear fluid of patients suffering from dry eyes," Graefe's Archive for Clinical and Experimental Ophthalmology, 233(11):694698 (1995).

Balci et al., "Effects of computer monitor-emitted radiation on oxidant/antioxidant balance in cornea and lens from rats," Molec Vis, 15:2521-2525 (2009).

Balci et al., "Investigation of oxidative stress in pterygium tissue," Molecular Vision, 17:443-447 (Feb. 2011).

Baltatzis et al., "Mycophenolate mofetil as an immunomodulatory agent in the treatment of chronic ocular inflammatory disorders," Ophthalmology, 110(5):1061-5. (May 2003).

Baz et al., "Plasma reactive oxygen species activity and antioxidant potential levels in rosacea patients: correlation with seropositivity to Helicobacter pylori," International Journal of Dermatology, 43(7):494-497 (2004).

Bermudez et al., "Thermosensitive poloxamer-based injectables as controlled drug release platforms for veterinary use: Development and in-vitro evaluation," Intl Res J Pharmacy Pharmacol, 1(6):109-118 (Sep. 2011).

Boyer et al., "Lipofuscin and N-Retinylidene-N-Retinylethanolamine (A2E) Accumulate in Retinal Pigment Epithelium in Absence of Light Exposure," J Biol Chem, 287(26):22276-22286 (Jun. 2012).

Brewitt et al., "Dry Eye Disease—The Scale of the Problem," Survey of Ophthalmol, 45(Suppl 2): S199-S2 (Mar. 2001).

Buddi et al., "Evidence of oxidative stress in human corneal diseases," The Journal of Histochemistry Society, Histochemistry and Cytochemistry: official journal of the 50(3):341-351 (2002).

Burstein, "Preservative cytotoxic threshold for benzalkonium chlorhexidine digluconate in cat and rabbit corneas," Investigative Visual Science, 19(3):308-313 (1980) chloride and Ophthalmology and Visual Science, 19(3):308-313 (1980).

Burstein, "The effects of topical drugs and preservatives epithelium in dry eye," Transactions of the Ophthalmological on the tears and corneal Societies of the United Kingdom, 104:402-409 (1985).

Cejkova et al., "The role of conjunctival epithelial cell oxidoreductase/xanthine oxidase in oxidative reactions on xanthine the ocular

(56) References Cited

OTHER PUBLICATIONS surface of dry eye (Sep. patients with Sjögren's syndrome," Histol Histopathol 22(9):997-1003 (Sep. 2007).
Chapple et al., "Unfolding Retinal Dystrophies: a Role for Molecular Chaperones?" Trends Mol Med, 7(9):414-421 (2001).
Chen et al., "Methazolamide Calcium Phosphate Nanoparticles in an Ocular Delivery System," Pharm Soc Japan, 130(3):419-24 (2010).
Chiarpotto et al., "Role of 4-hydroxy-2,3-nonenal in the pathogenesis of fibrosis," Biofactors, 24(1-4):229-36 (2005).
Choi et al., "Expression of Lipid Peroxidation Markers in the Tear Film and Ocular Surface of Patients with Non-Sjogren Syndrome: Potential Biomarkers for Dry Eye Disease," Curr Eye Res, 41(9):1143-11 (2016).
ClinicalTrials.gov identifier NCT02406209, "A Safety and Efficacy Study of NS2 in Patients with Anterior Uveitis," https://clinicaltrials.gov/ct2/show/NCT02406209 (4 pages) (2015).
Clinical Trials Results of Treatment with Aldehyde Trapping Compound NS2 (1 page) (2015).
Clinical Trials Results of Treatment with NS2 Topical Formulation (1 page) (2015).
Cullen et al, "The small molecule aldehyde trap NS2 exhibits potent anti-inflammatory activity in three murine models of inflammation," AAAAI Annual Meeting Abstract, 1 page (Feb. 2015).
Del Valle, "Cyclodextrins and their uses: a review," Process Biochemistry, 39(9):1033-1046 (2004).
Demir et al., "The protective effect of alpha-lipoic acid against oxidative damage in rabbit conjunctiva and cornea exposed to ultraviolet radiation," Ophthalmologica, 219(1):49-53 (Jan.-Feb. 2005).
Demir et al., "Oxidative stress of intracameral lidocaine and levobupivacaine on ocular tissues," Br J Ophthalmol, 94(8):1083-7 (Aug. 2010).
Esterbauer et al., "Chemistry and Biochemistry of 4-Hydroxynonenal, Malonaldehyde and Related Aldehydes," Free Radic Biol Med, 11:81-128 (1991).
European Supplementary Partial Search Report issued by the European Patent Office for European Patent Application No. 14743711.5 dated Jul. 20, 2016 (14 pages).
Full 1H NMR assignment for Ral-NS2 in CDCIJ, submitted to Japanese Patent Office Mar. 1, 2012.
Gasper et al., "2-Hydroxypropyl-beta-cyclodextrin (HPDCD) reduces age-related lipofuscin accumulation through a cholesterol-associated pathway," Scientific Reports, 7(2197):1-7 (2017).
Gibson et al., "The Aldehyde Trap NS2 Mitigates Dense Haze in a Rabbit Model of Photorefractive Keratectomy" Arvo Annual Meeting Abstract, 1 page (Jun. 2015).
Green et al., "Influence of Various Agents on Corneal Permeability," American Journal of Ophthalmology, 72(5):897-905 (1971).
Grotto et al., "Importance of the lipid peroxidation biomarkers and methodological aspects for malondialdehyde quantification," Quim Nova, 32(1):169-174 (2009).
Halilovic et al., "ADX-103, a Novel Small Molecule Aldehyde Sequestering Agent, Decreases Retinal Edema and Inflammation in a Rat Model of Diabetic Macular Edema," ARVO Annual Meeting Abstract, 2 pages (Jul. 2018).
Herbort et al., "Endotoxin-induced uveitis in the rat," Graefe's Arch Clin Exp Ophthalmol, 226:553-8 (1988).
International Preliminary Report on Patentability issued by the United States Patent and Trademark Office as International Searching Authority for International Application No. PCT/US2014/012762 dated Jul. 28, 2015 (8 pages).
International Search Report and Written Opinion issued by the United States Patent and Trademark Office as International Searching Authority for International Application No. PCT/US2010/059719 dated Feb. 8, 2011 (7 pages).
International Search Report and Written Opinion issued by the United States Patent and Trademark Office as International Searching Authority for International Application No. PCT/US2014/012762 dated Jul. 18, 2014 (11 pages).

Kenney et al., "The Cascade Hypothesis of Keratoconus," Contact Lens & Ant Eye, 26:139-146 (2003).
Keri, "Rosacea," Merck Manual, Professional Version, https://www.merckmanuals.com/professional/dermatologic-disorders/acne-and-related-disorders/rosacea, 7 pages (2017).
Macdonald et al., "ADX-102, a novel aldehyde trap, reduces nociceptive behavior in mouse models of carrageenan and CFA induced pain," Int'l Conference on Pain Research & Management Abstract, J Pain Relief, 5 (5 Suppl):50 (Oct. 2016).
Macdonald et al., "Inhibition of fibroblast activation to the myofibroblast phenotype in neonatal rat cardiac fibroblasts using a small molecule aldehyde trap," ASCB Annual Meeting Abstract, p. 2 (Dec. 2016).
Macdonald et al., "The novel aldehyde trap, ADX-102, reduces inflammation-mediated lung infiltrate in a mouse model of LPS-induced acute lung injury," 13th World Congress on Inflammation Abstract, p. 192 (Jul. 2017).
Macdonald et al., "Novel Small Molecule Aldehyde Sequestering Agents Demonstrate Broad Therapeutic Potential for Ocular Inflammation," ARVO Annual Meeting Abstract, 2 pages (Jul. 2018).
Maeda et al., "Involvement of All-trans-retinal in Acute Light-induced Retinopathy of Mice," J Biol Chem, 284(22):15173-83 (May 2009).
Maeda et al., "Primary amines protect against retinal degeneration in mouse models of retinopathies," Nat Chem Biol, 8(2):170-178 (Dec. 2011).
Martin et al., "Molecular cloning and functional characterization of murine cysteinyl-leukotriene 1 (CysLT(1)) receptors.," Biochem. Pharmacol., 62:1193-1200 (2001).
Negre-Salvayre et al., "Advanced Lipid Peroxidation End Products in Oxidative Damage to Proteins. Potential Role in Diseases and Therapeutic Prospects for the Inhibitors," Br J Pharmacol, 153(1):6-20 (2008).
Nema et al., "Excipients and Their Use in injectable Products," PDA J Pharm Sci Technol, 51(4):166-171 (1997).
O'Brien et al., "Aldehyde Sources, Metabolism, Molecular Toxicity Mechanisms, and Possible Effects on Human Health," Crit Rev Toxicol, 35:609-662 (2005).
Pred Forte Prescribing Information, Allergan, 5 pages (2017).
Rauli et al., "Validation of Malondialdehyde and 4-Hydroxy-2-trans-Nonenal Measurement in Plasma by NICI-GC-MS1," J Biochem, 123:918-923 (1998).
Rizzo, "The role of fatty aldehyde dehydrogenase in epidermal structure and function" Dermato-Endocrinol, 3(2):91-99 (2011).
Roat, "Keratoconjunctivitis Sicca," Merck Manual Professional Version, 5 pages (2016), Available at: https://www.merckmanuals.com/professional/eye-disorders/corneal-disorders/keratoconjunctivitis-sicca.
Roat, "Allergic Conjunctivitis," Merck Manual Professional Version, 3 pages (2016), Available at: https://www.merckmanuals.com/professional/eye-disorders/conjunctival-and-scleral-disorders/allergic-conjunctivitis.
Roat, "Ocular Mucous Membrane Pemphigoid," Merck Manual Professional Version, 3 pages (2016), Available at: https://www.merckmanuals.com/professional/eye-disorders/conjunctival-and-scleral-disorders/ocular-mucous-membrane-pemphigoid.
Roat, "Scleritis," Merck Manual Professional Version, 3 pages (2016), Available at: https://www.merckmanuals.com/professional/eye-disorders/conjunctival-and-scleral-disorders/scleritis.
Sandikci et al., "Lipid Peroxidation and Antioxidant Defence System in Patients with Active or Inactive Behcet's Disease," Acta Derm Venereol, 83:342-346 (2003).
Sasaki et al., "Retinal drug delivery using eyedrop preparations of poly-L-lysine-modified liposomes," Eur J Pharm Biopharm, 83(3):364-9 (2013).
Schaumberg et al., "Prevalence of Dry Eye Syndrome Among US Women," Am J Ophthalmol, 136(2):318-326 (Aug. 2003).
Schaumberg et al., "Prevalence of Dry Eye Disease among US Men: Estimates from the Physicians' Health Studies," Arch Ophthalmol, 127(6):763-768 (Jun. 2009).
Serbecic et al., "Anti-oxidative vitamins prevent lipid-peroxidation and apoptosis in corneal endothelial cells," Cell Tissue Res, 320(3):465-75 (Jun. 2005).

(56) References Cited

OTHER PUBLICATIONS

Schramm et al., "The Cross-linked Biopolymer Hyaluronic Acid as an Artificial Vitreous Substitute," Invest Ophthalmol Vis Sci, 53(2):613-621 (Feb. 2012).
Smith et al., "Basic pathogenic mechanisms operating in experimental models of acute anterior uveitis," Immunol Cell Biol, 76:497-512 (1998).
Sparrow et al. "Phospholipid meets all-trans-retinal: the making of RPE bisretmoids," Journal of Lipid Research, 51: 247-261 (2010).
Tang et al., "Effects of four penetration enhancers on corneal permeability of drugs in vitro," Journal of Pharmaceutical Sciences, 83(1):85-90 (1994).
Turk et al., "Serum anti-carbonic anhydrase antibodies and oxidant-antioxidant balance in patients with acute anterior uveitis," Ocul Immunol Inflamm, 22(2):127-32 (Apr. 2014).
Ueda et al., "Evaluation of a Sulfobutyl Ether 13-Cyclodextrin as a Solubilizing/Stabilizing Agent for Several Drugs," Drug Dev Ind Pharm, 24(9):863-867(1998).
Wood et al., "The concept of "aldehyde load" in neurodegenerative mechanisms: cytotoxicity of the polyamine degradation products hydrogen peroxide, acrolein, 3-ammopropanal, 3-acetamidiorioanal and 4-aminobutanal in a retinal ganglion cell line," Brain Research, 1145:150-156 (2007).
Yadav et al., "Regulation of Nf-κb-Induced Inflammatory Signaling by Lipid Peroxidation-Derived Aldehydes," Oxidative Med & Cell Longev, 2013, Art ID 690545, 11 pages (2013).
Yarnell, "Light Flips the Lipid Switch: Palmitoylation—the reversible attachment of palmitate to proteins—gets a new role in vision," C&EN, 82(29):22-23 (2004).
Yu et al., "Injectable Chemically Crosslinked Hydrogel for the Controlled Release of Bevacizumab in Vitreous: A 6-Month in Vivo Study," Transl Vis Sci Technol, 4(2,5):1-11 (2015).
Zagol-Ikapitte et al., "Characterization of scavengers of γ-ketoaldehydes that do not inhibit prostaglandin biosynthesis," Chem Res Toxicol, 23(1):240-250 (2010).
Zhou et al., "Mechanisms for the induction of HNE-MDA-and AGE-adducts, RAGE and VEGF in retinal pigment epithelial cells," Exp Eye Res., 80(4):567-80 (2005).
U.S. Appl. No. 16/157,069 of Macdonald et al., filed Oct. 10, 2018.
U.S. Appl. No. 16/168,309 of Chabala et al., filed Oct. 23, 2018.
U.S. Appl. No. 16/300,020 of Brady et al., filed Nov. 8, 2018.
U.S. Appl. No. 16/241,851 of Jordan et al., filed Jan. 7, 2019.
U.S. Appl. No. 16/262,364 of Brady et al., filed Jan. 30, 2019.
U.S. Appl. No. 16/277,865 of Brady et al., filed Feb. 15, 2019.

* cited by examiner

SCHEDULE OF PROCEDURES

| Procedure | Medical Screening Visit 1 | Titrating CAPT Visit 2 | Confirm CAPT Visit 3 | Re-Confirm CAPT Visit 3B (if necessary) | CAPT OOA Visit 4 | CAPT Visit 5 | CAPT Visit 6 | CAPT Visit 7 |
|---|---|---|---|---|---|---|---|---|
| Informed consent | ✓ | | | | | | | |
| Demographics | ✓ | | | | | | | |
| Medical, Ocular & Medications History | ✓ | | | | | | | |
| Skin Prick Test | ✓ | | | | | | | |
| Pregnancy Test | ✓ | | | | | | | |
| Vital Signs | ✓ | | | | | | | ✓ |
| Inclusion/Exclusion Criteria | ✓ | ✓ | ✓ | ✓ | ✓ | ✓ | ✓ | ✓ |
| VA | ✓ | ✓ | ✓ | ✓ | ✓ | ✓ | ✓ | ✓¹ |
| Slitlamp Exam | ✓ | ✓ | ✓ | ✓ | ✓ | ✓ | ✓ | ✓¹ |
| NCT & Fundus Exam | ✓ | | | | | | | ✓ |
| Change in Health & Medications | | ✓ | ✓ | ✓ | ✓ | ✓ | ✓ | ✓ |
| Randomization | | | | | ✓ | | | |
| Dispense at home diary card & drug | | | ✓ | | ✓ | | ✓ | |
| Collect at home diary card & drug | | | | | | ✓ | | ✓ |
| ePDAT Subjective symptom Collection (Ocular itching, tearing) (Table 2) | | ✓ | ✓ | ✓ | ✓ | ✓ | ✓ | ✓ |
| On Site Drop Administration | | | | | ✓ | ✓ | ✓ | ✓ |
| Conjunctival Allergen Provocation Test (CAPT) | | ✓ | ✓ | ✓ | ✓ | ✓ | ✓ | ✓ |
| Ocular Signs (Redness, lid swelling) (Table 2) | | ✓ | ✓ | ✓ | ✓ | ✓ | ✓ | ✓ |
| Tear Collection | | | ✓² | ✓ | | ✓² | | |
| Adverse Events | ✓ | ✓ | ✓ | ✓ | ✓ | ✓ | ✓ | ✓ |
| Study Exit | | | | | | | | ✓ |

FIG. 2

SCHEDULE OF SUBJECT SYMPTOM AND STAFF ASSESSED SIGN RECORDING

| | Timepoints in minutes | | | | | | | | | | |
|---|---|---|---|---|---|---|---|---|---|---|---|
| | 0 | 2.5 (+1min) | 5 (+2min window) | 10 (+2min window) | 15 | 30 | 60 | 90 (+5min window) | 120 | 150 | 180 |
| Visit 2 (Titrating CAPT) | √ | √[1,2] | √[2] | √[2] | | | | | | | |
| Visit 3 and 3B (Confirm CAPT) | √ | √[1] | √ | √ | √ | √ | √ | √ | √ | √ | √ |
| Visit 4 OOA | √ | √[1] | √ | √ | √ | √ | √ | √ | √ | √ | √ |
| Visit 5, 6 & 7 | √ | √[1] | √ | √ | √ | √ | √ | √ | √ | √ | √ |

√[1] Only for subject assessment of itching
√[2] For titrating CAPT the 2.5, 5, and 10 min diary cards are repeated until a positive allergen response

*FIG. 3*

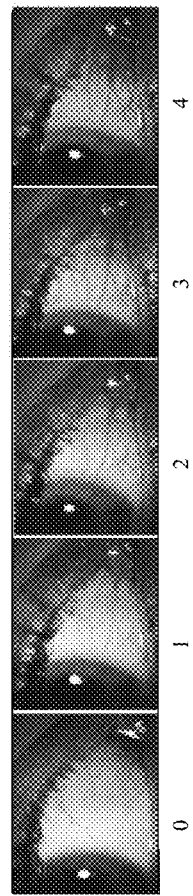

TREATMENT OF ALLERGIC EYE CONDITIONS WITH CYCLODEXTRINS

1. CROSS REFERENCE TO RELATED APPLICATIONS

This application claims the benefit under 35 U.S.C. § 119(e) of U.S. Provisional Application No. 62/315,488, filed Mar. 30, 2016, and U.S. Provisional Application No. 62/300,907, filed Feb. 28, 2016, the contents of all of which are incorporated herein in their entireties by reference thereto.

2. BACKGROUND

Acute allergic conjunctivitis is an inflammation of the conjunctiva, typically resulting from hypersensitivity reactions to various types of allergens. These hypersensitivity reactions involve allergen induced, immunoglobulin E (IgE)-mediated release of histamine and other mediators from mast cells and basophils. Mast cell degranulation leads to release of inflammatory mediators, such as cytokines and prostaglandins, and activation of enzymatic cascades generating pro-inflammatory mediators. In the eye, these biological events lead to inflammation of the conjunctival mucosa that also affects the cornea and eyelids, with symptoms that include itching and burning, tearing, chemosis (conjunctival edema), conjunctival injection, hyperemia, eyelid edema, and mucus discharge.

Allergic conjunctivitis disorders can be grouped into seasonal allergic conjunctivitis (SAC) and perennial allergic conjunctivitis (PAC). In SAC, recurrent allergic conjunctivitis is caused by environmental exposure to seasonal allergens, such as ragweed and pollen, whereas with PAC, afflicted subjects have year-round symptoms that are most commonly triggered by indoor allergens, such as mold, animal dander, dust mites, and feathers. Both acute conditions usually have bilateral involvement, but the symptoms of SAC are generally more severe than those related to PAC.

Various treatments have been developed for treating allergic conjunctivitis, including topical antihistamines, non-steroidal anti-inflammatory drugs, corticosteroids, and immune response modulators. For example, an exemplary course of treatment have used antihistamines, such as pheniramine, antazoline, levocabastine and emadastine, but these compounds have limited anti-inflammatory effects and duration of efficacy. Current therapies for the management of allergic conjunctivitis are drugs having both anti-histaminic and mast cell stabilizing properties such as olopatadine, ketotifen and azelastine. However, these compounds often fail to provide relief of more than one ocular allergy symptom and some of the known treatments with pharmaceutically active compounds can result in undesirable side effects, such as pain, swelling and vision changes.

3. SUMMARY

The present disclosure provides a method of treating eye allergy, manifested as allergic conjunctivitis, by administration of a therapeutically effective amount of a cyclodextrin or a composition comprising a cyclodextrin. In some embodiments, a method of treating eye allergy or allergic conjunctivitis comprises administering to an eye of a subject in need of treatment a therapeutically effective amount of a cyclodextrin or an ophthalmic composition comprising a cyclodextrin. In some embodiments, the allergic conjunctivitis treated is seasonal or perennial allergic conjunctivitis. In some embodiments, the allergic conjunctivitis treated is vernal or atopic keratoconjunctivitis.

In some embodiments, cyclodextrin is used as prophylactic treatment to prevent or ameliorate the onset of symptoms of eye allergy or allergic conjunctivitis. In some embodiments, a method of preventing or ameliorating the onset of symptoms of eye allergy or allergic conjunctivitis comprises administering to an eye of a subject in need of treatment a therapeutically effective amount of a cyclodextrin of a composition comprising a cyclodextrin. In some embodiments, the subject selected for prophylactic treatment has been previously diagnosed with eye allergies, manifested as allergic conjunctivitis, or previously identified as being susceptible or sensitive to an eye allergen.

In some embodiments, the cyclodextrin is used to inhibit, bind or sequester an eye allergen. In some embodiments, a method of inhibiting, binding or sequestering an eye allergen comprises administering to an eye of a subject in need of treatment an effective amount of a cyclodextrin. In some embodiments, the subject selected for treatment has been previously diagnosed with an eye allergy or allergic conjunctivitis, or previously identified as being susceptible or sensitive to an eye allergen.

In some embodiments, the cyclodextrin or composition comprising a cyclodextrin can be used to bind, sequester, deactivate, or inhibit a toxic aldehyde associated with allergic conjunctivitis. In some embodiments, a method of binding, sequestering, deactivating, or inhibiting a toxic aldehyde compound in the eye comprises topically administering to the eye of a subject in need of treatment an effective amount of a cyclodextrin or a composition comprising a cyclodextrin. In some embodiments, the subject is determined to have an eye allergy or allergic conjunctivitis.

In some embodiments, the cyclodextrin or composition comprising a cyclodextrin can be used to reduce or treat inflammation in the eye associated with eye allergy or allergic conjunctivitis. In some embodiments, a method of treating inflammation comprises administering to an eye of a subject in need of treatment a therapeutically effective amount of a cyclodextrin or a composition comprising a cyclodextrin.

In some embodiments of the foregoing methods, the cyclodextrin is administered as the sole or only pharmaceutically active agent. In some embodiments, the cyclodextrin used in the methods is substantially free of inclusion complexes formed with a pharmaceutically active agent. In some embodiments, the ophthalmic composition comprising the cyclodextrin is substantially free of a pharmaceutically active agent which is capable of forming an inclusion complex with the cyclodextrin. In particular, the cyclodextrin or the ophthalmic composition thereof is substantially free of an ophthalmic pharmaceutically active agent capable of forming an inclusion complex with the cyclodextrin.

In some embodiments, the cyclodextrin is selected from α-cyclodextrin, β-cyclodextrin, γ-cyclodextrin, derivatives thereof, and combinations thereof. In some embodiments, the cyclodextrin or derivative thereof is selected from carboxyalkyl cyclodextrin, hydroxyalkyl cyclodextrin, sulfoalkylether cyclodextrin, alkyl cyclodextrin, and combinations thereof. In some embodiments, the cyclodextrin or derivatives thereof is sulfoalkylether-β-cyclodextrin or hydroxyalkyl-β-cyclodextrin, particularly sulfobutylether-β-cyclodextrin or hydroxypropyl-β-cyclodextrin In a further aspect, the present disclosure also provides cyclodextrin formulations, particularly compositions of cyclodextrin, more particularly ophthalmic compositions of cyclodextrin for use in the methods. In some embodiments, cyclodextrin is the sole or only pharmaceutically active agent in the cyclodextrin formulation. In some embodiments, the composition comprising the cyclodextrin is substantially free of inclusion complexes formed with a pharmaceutically active agent. In some embodiments, the composition is an ophthalmic composition comprising the cyclodextrin, where the ophthalmic composition is substantially free of a pharmaceutically active agent which is capable of forming an inclusion complex with the cyclodextrin. In particular, the cyclodextrin or the ophthalmic composition thereof is substantially free of an ophthalmic pharmaceutically active agent capable of forming an inclusion complex with the cyclodextrin. In some embodiments, the ophthalmic compositions comprising a cyclodextrin includes one or more an ophthalmic pharmaceutically acceptable excipient, such as one or more of a tonicity agent, preservative, buffering agent, pH adjusting agent, solubilizing agent, surfactant, chelating agent, emulsifying agent, suspending agent, stabilizing agent, and antioxidant.

While in some embodiments the ophthalmic composition for use in the methods has cyclodextrin as the sole or only pharmaceutically active agent, in other embodiments the ophthalmic composition can also comprise a cyclodextrin and a pharmaceutically active agent. In some embodiments, the ophthalmic composition comprises a cyclodextrin, a pharmaceutically active agent, and one or more of an ophthalmic pharmaceutically acceptable excipient. In some embodiments, the pharmaceutically active agent is an ophthalmic pharmaceutically active agent, particularly a pharmaceutically active agent for treating eye allergy or allergic conjunctivitis. In some embodiments, the pharmaceutically active agent is capable of forming inclusion complexes with the cyclodextrin. In some embodiments, the cyclodextrin or derivative thereof is present in an amount sufficient to contain an effective amount (e.g., concentration) of free, uncomplexed cyclodextrin to provide a therapeutic benefit in addition to the therapeutic benefit provided by the pharmaceutically active agent. In particular, the cyclodextrin or derivative thereof is present in an amount sufficient to provide an effective amount of free, uncomplexed cyclodextrin to provide a therapeutic benefit in treating eye allergy or allergic conjunctivitis, in addition to the amount needed to enhance solubility and/or bioavailability of the pharmaceutically active agent. In some embodiments, a pharmaceutically active agent formulated with cyclodextrin useful for treating allergic conjunctivitis, includes, among others, mast cell stabilizers, steroids, antihistamines, non-steroidal anti-inflammatory drugs (NSAIDs), and aldehyde trapping compounds. In some embodiments, the pharmaceutically active agent for treating eye allergy or allergic conjunctivitis is the compound of structural formula (I), as provided in the detailed description.

In a further aspect, the present disclosure provides a kit comprising the cyclodextrin or composition thereof for use in the methods, such as for the treatment of eye allergy or allergic conjunctivitis. In some embodiments of the kit, the composition can have cyclodextrin as the sole or only pharmaceutically active agent. In some embodiments, the composition can have cyclodextrin and a pharmaceutically active agent, including a pharmaceutically active agent capable of forming inclusion complexes with the cyclodextrin. In some embodiments, the composition in the kit can be an ophthalmic solution comprising a cyclodextrin, where the solution is provided in a single use vial, such as a disposable plastic squeeze vial, particularly a vial with a non-resealable snap-off or tear-off cap. In some embodiments, one or more of the single use vials are provided in the kit.

4. BRIEF DESCRIPTION OF THE FIGURES

FIG. 1 provides a flow chart of the clinical trials protocol for accessing the safety and efficacy of aldehyde trapping compound NS2.

FIG. 2 provides a table showing the scheduled procedures for conducting the patient visits during the clinical trial.

FIG. 3 provides the schedule of the patient symptom and staff assessed recordings in the clinical trial.

FIG. 4 illustrates the scoring of ocular redness based on examination of the eye.

FIG. 12 illustrates the competitive binding of allergens to sulfobutylether-β-cyclodextrin/NS2 complexes, where the ratio of sulfobutylether-β-cyclodextrin:NS2 is 19:1 and the ratio of allergen protein:NS2 is 2:1.

FIG. 13 illustrates the competitive binding of allergens to hydroxypropyl-γ-cyclodextrin/NS2 complexes, where the ratio of hydroxypropyl-γ-cyclodextrin:NS2 is 30:1 and the ratio of allergen protein:NS2 is 2:1.

5. DETAILED DESCRIPTION

Figure 1:
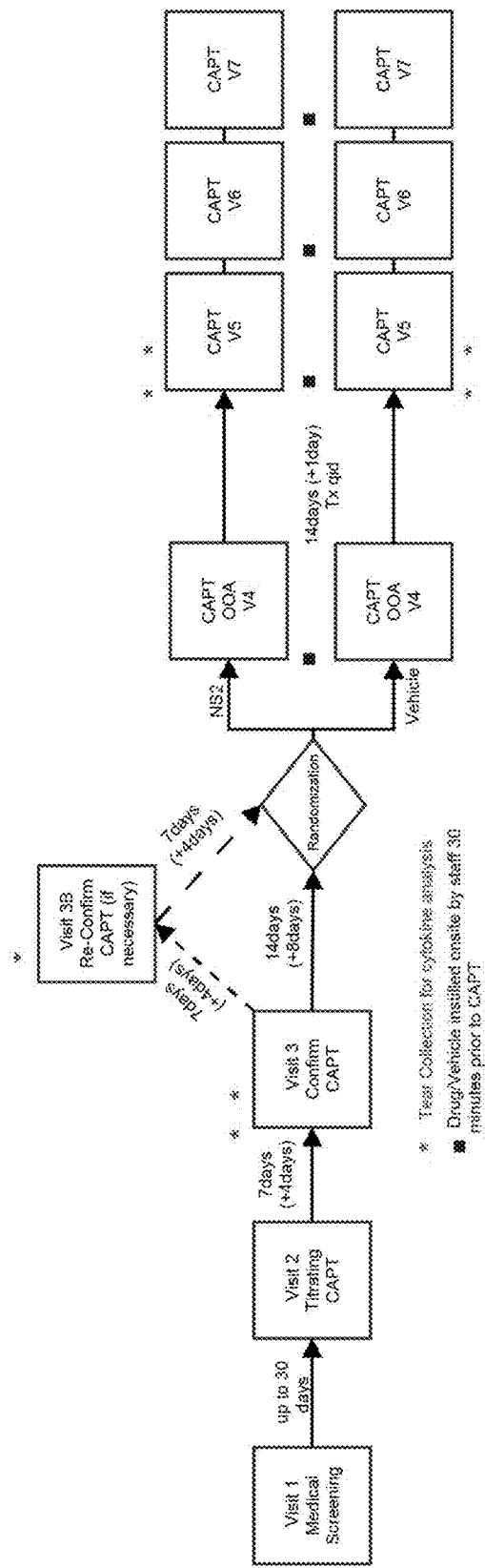

The present disclosure relates to use of cyclodextrin and compositions thereof for the treatment of eye allergies, particularly manifesting as allergic conjunctivitis; inhibiting eye allergic responses; and/or inhibiting or reducing the levels of toxic aldehyde compounds associated with allergic responses in the eye. In view of the ability of cyclodextrin to act as a pharmacologically active agent in treating eye allergies and allergic conjunctivitis, the cyclodextrin can be used alone, as the sole or only pharmaceutically active agent, for example, substantially free of a pharmaceutically active agent that can form inclusion complexes with the cyclodextrin.

As used in this specification and the appended claims, the singular forms "a", "an" and "the" include plural referents unless the context clearly indicates otherwise. Thus, for example, reference to "a compound" refers to more than one compound.

Also, the use of "or" means "and/or" unless stated otherwise. Similarly, "comprise," "comprises," "comprising," "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The foregoing general description, including the drawings, and the following detailed description are exemplary and explanatory only and are not restrictive of this disclosure.

The section headings used herein are for organizational purposes only and not to be construed as limiting the subject matter described.

5.1. Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings:

"Allergic conjunctivitis" refers to a collection of hypersensitivity disorders that affect the eye lid, conjunctiva and/or cornea. Diagnosis is primarily clinical, but tests such as cytology, conjunctival provocation and tear mediator analysis can be performed. See, e.g., Merck Manual of Diagnosis and Therapy, 19th Ed., Wiley (2011)). Symptoms typically include itching, lacrimation, discharge, and conjunctival hyperemia.

"Seasonal allergic conjunctivitis" or "SAC" refers to allergic conjunctivitis arising from seasonal allergen. In some embodiments, suspected allergens in SAC correspond to the seasonal life cycle of one or more causative plant or other vegetation that produces the suspected allergen.

"Perennial allergic conjunctivitis" or "PAC" refers to a form of allergic conjunctivitis occurring throughout the year. Suspected common perennial allergens include, by way of example and not limitation, animal dander (e.g., hair, skin particles), feathers, dust mites, chemicals, tobacco smoke, and the like.

"Vernal keratoconjunctivitis" or "VKC" refers to a chronic form of allergic conjunctivitis, typically characterized by bilateral chronic inflammation of the conjunctiva. Severe forms of VKC display square, hard, flattened, closely packed, pale pink to grayish cobblestone papillae (palpebral form) and/or dusky red triangular congestion of bulbar conjunctiva in palpebral area (bulbar form). See, e.g., Merck Manual of Diagnosis and Therapy, 19th Ed., Wiley (2011).

"Atopic keratoconjunctivitis" or "AKC" refers to a chronic form of allergic conjunctivitis typically characterized by bilateral chronic inflammation of the conjunctiva and often occurs concomitant with eczema, atopic dermatitis and asthma. The condition is more prevalent in men and in ages 30 to 50. It may also involve the cornea, and may lead to blindness. See, e.g., Merck Manual of Diagnosis and Therapy, 19th Ed., Wiley (2011).

"Allergen" refers to a substance that can induce an allergic response in a susceptible subject.

"Eye allergy" or "ocular allergy" refers to an allergic reaction or disorder of the eye, such as on the ocular surface, caused by one or more allergens.

"Cyclodextrin" refers to compounds composed of sugar molecules bound together in a ring (i.e., cyclic oligosaccharides). In some embodiments, the sugar molecules of the cyclodextrin are composed of α-D-glucopyranosyl units connected via α(1,4) linkages. The number of sugar units can range from 5 to 32 or more. Naturally occurring cyclodextrins include, among others, α-cyclodextrin (6 glucopyranosyl units), β-cyclodextrin (7 glucopyranosyl units) and γ-cyclodextrin (8 glucopyranosyl units). Unless specifically described otherwise, the term "cyclodextrin" includes derivatives of cyclodextrin compounds.

"Substantially free" of a pharmaceutically active agent or component or equivalents thereof refers to at least a level of a pharmaceutically active agent or component which is below the therapeutically effective level (e.g., concentration) of the pharmaceutically active agent or component. In some embodiments, less than 5%, less than 4%, less than 5%, less than 1%, or less than 0.5% of the cyclodextrin is present as an inclusion complex with a pharmaceutically active agent or component. In some embodiments, the pharmaceutically active agent or component is absent from the composition.

"Substantially free" of an undesirable component in a pharmaceutical composition, such as the level of bacterial contamination, level of pyrogen, or level of endotoxin, is the maximal level allowable by a governmental agency, such as the United States Food and Drug Administration (FDA), for marketing approval of the pharmaceutical composition. In some embodiments, the undesirable component is absent from the pharmaceutical composition.

"Pharmaceutically active component" or "pharmaceutically active agent" refers to a pharmacophore, such as a drug or other therapeutic compound. In some embodiments, the "pharmaceutically active component" or "pharmaceutically active agent" is capable of forming inclusion complexes with a cyclodextrin.

"Treating" or "treatment" of a disease, disorder, or syndrome, as used herein, includes (i) preventing the disease, disorder, or syndrome from occurring in a subject, i.e., causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and is ascertainable by one of ordinary skill in the art.

"Prophylactic treatment" is a treatment administered to a subject who does not display signs or symptoms of a disease, pathology, or medical disorder, or displays only early signs or symptoms of a disease, pathology, or disorder, for the purpose of diminishing, preventing, or decreasing the risk of developing the disease, pathology, or medical disorder. A prophylactic treatment functions as a preventative treatment against a disease or disorder.

"Therapeutically effective amount" means any amount which, as compared to a corresponding subject who has not received such amount, results in improved treatment, healing, prevention, or amelioration of a disease or disorder, or a decrease in the rate of advancement of a disease or disorder, and also includes amounts effective to enhance normal physiological function.

"Effective amount" refers to that amount of a drug or pharmaceutical agent that will result in the desired biological or medical response that is being sought of a tissue, system, animal or human.

"Alkyl" refers to a noncyclic straight chain or branched, unsaturated or saturated hydrocarbon such as those containing from 1 to 10 carbon atoms, particularly 1 to 8 carbon atoms, more particularly 1 to 6 carbon atoms. Exemplary alkyls include, among others, methyl, ethyl, propyl, butyl, pentyl and hexyl.

"Pharmaceutically acceptable" as used herein refers to materials or substances that are generally not toxic or injurious to a subject.

"Additive" in the context of a pharmaceutical composition is intended to include any pharmaceutically acceptable carrier, diluent or excipient, particularly a carrier, diluent, or excipient suitable for ophthalmic use.

"Excipient" refers to an ingredient or component that provides one or more of bulk, imparts satisfactory processing characteristics, helps control the dissolution rate or otherwise gives additional desirable characteristics to the compositions. Included within this term, inter alia, are compounds well known to those of ordinary skill in the art, as described, for example, in the Handbook of Pharmaceutical Excipients, 4th Ed., American Pharmaceutical Association, Washington, D.C. and Pharmaceutical Press, London, England, 2003), incorporated herein by reference in its entirety. In particular, the excipients are selected such that the composition, particularly an ophthalmic composition, does not trigger pain and/or a secretion of tears.

"About" or "approximately" refers to an acceptable error range for the particular value as determined by one of ordinary skill in the art, which will depend in part on how the value is measured or determined, i.e., the limitations of the measurement system. For example, "about" can mean a range of up to 20%, preferably up to 10%, more preferably up to 5%, and more preferably still up to 1% of a given value.

5.2. Detailed Description of Methods and Compositions

Cyclodextrins typically comprise compounds composed of α-D-glucopyranosyl units linked together to form a toroid or cone shaped structure in which the interior is generally more hydrophobic than the hydrophilic exterior. Because of this unique structure, cyclodextrins can form inclusion complexes with other hydrophobic compounds that fit in the interior cavity of the cyclodextrin while remaining water soluble due to the hydrophilic exterior. In many instances, cyclodextrin can enhance the aqueous solubility characteristics of a poorly water soluble drug if the drug forms inclusion complexes with the cyclodextrin.

Cyclodextrins have been used in various ophthalmic formulations, particularly to enhance the solubility of poorly water soluble ophthalmic drugs and to enhance their bioavailability. Exemplary formulations employing cyclodextrins for ophthalmic applications have been described for, among others, anti-glaucoma agent arylsulfonylureido benzenesulfonamide (Bragagni et al., 2015, *Bioorg Med Chem.* 23(18):6223-7), cyclosporine (Jóhannsdóttir et al., 2015, *Intl J Pharm.* 493(1-2):86-95), corticosteroids (e.g., Loftsson et al., 2002, *Acta Ophthalmol Scand.* 80: 144-150), dexamethasone (e.g., Loftsson et al., 2007, *J Pharm Pharmacol* 59: 629-635), ciprofloxacin (Bozkir et al., 2012, *Acta Pol Pharm.* 69(4):719-24), and olopatadine (U.S. Pat. No. 8,791, 154; Torkildson et al., 2015, *Clin Ophthalmol.* 9:1703-1723). Cyclodextrin by itself, without a pharmaceutically active agent, have also been used to bind and clear cholesterol, for example as a potential treatment for Nieman-Pick disease (Pontikis et al., 2013, *J Inherit Metab Dis.* 36(3):491-8). In other studies, hydroxypropyl-β-cyclodextrin have been suggested a potential treatment for retinal aging correlated with accumulation of amyloid protein (Aβ) and related inflammatory responses based on studies using complement factor H (Cfh$^{-/-}$) knockout animal models of retinal aging, which are characterized by accumulation of amyloid protein (Aβ) in the eye. β-cyclodextrin has also been shown to bind all trans-retinol and lipofuscin A2E, the latter of which has been implicated in age-related macular degeneration and Stargardt's disease (Kam et al., 2015, *Exp Eye Res.* 135:59-66; Johnson et al., 2010, *J Ocul Pharmacol Therap.* 26(3):245-248).

The present invention is based on the surprising observation from clinical trials of an aldehyde trapping compound NS2, having the structure of formula (I)

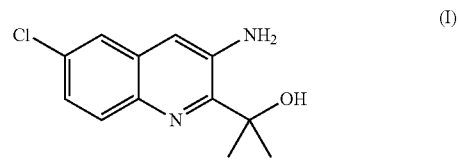 [SMILES: CC(C)(O)c1nc2ccc(Cl)cc2cc1N]

formulated with sulfobutylether-β-cyclodextrin for the treatment of allergic conjunctivitis in which the control group administered sulfobutylether-β-cyclodextrin with no aldehyde trapping compound (i.e., vehicle only group) showed high response rates and significant efficacy in treating allergic conjunctivitis. A single drop of cyclodextrin administered four times daily over a period of two weeks was effective in ameliorating the symptoms of allergen induced allergic conjunctivitis. The clinical trials protocol implemented to examine the effectiveness of the compound of structural formula (I) formulated with sulfobutylether-β-cyclodextrin for treating allergic conjunctivitis is described in the Examples.

Without being bound by theory, the topically administered β-cyclodextrin may bind to allergens that come in contact with the eye, thereby reducing or inhibiting the allergen-induced hypersensitivity reaction. Alternatively, the β-cyclodextrin may be forming inclusion complexes with toxic aldehyde compounds and/or the aldehyde reaction products that play a role in allergic conjunctivitis. It is to be understood that the indicated mechanisms are not mutually exclusive and that the cyclodextrin may have a therapeutic effect through a combination of mechanisms, including binding to allergens and binding to toxic aldehyde compounds. These results from the clinical trials show that cyclodextrin by itself is pharmacologically active and is effective in treating eye allergies manifesting as allergic conjunctivitis.

Accordingly, in one aspect, a method of treating an eye allergy comprises administering to a subject in need thereof a therapeutically effective amount of a cyclodextrin, or a composition comprising a cyclodextrin. In some embodiments, a method of treating allergic conjunctivitis comprises administering to a subject in need thereof a therapeutically effective amount of a cyclodextrin, or a composition comprising a cyclodextrin.

In some embodiments, the method of treating eye allergy or allergic conjunctivitis comprises topically administering to an eye of a subject in need thereof a therapeutically effective amount of a cyclodextrin, or an ophthalmic composition comprising a cyclodextrin. In some embodiments, the cyclodextrin, or an ophthalmic composition is topically administered to ameliorate or mitigate one or more symptoms of eye allergy or allergic conjunctivitis, such as ocular itching, redness, chemosis, and lid swelling, In some embodiments, the cyclodextrin is administered as the sole or only pharmaceutically active agent for treating the eye allergy, as manifested as allergic conjunctivitis. In some embodiments, the cyclodextrin is substantially free of inclusion complexes with a pharmaceutically active agent. In some embodiments, the ophthalmic composition comprising the cyclodextrin is substantially free of a pharmaceutically active agent which is capable of forming an inclusion complex with the cyclodextrin. In particular, the cyclodextrin or the ophthalmic composition thereof is substantially free of an ophthalmic pharmaceutically active agent capable of forming an inclusion complex with the cyclodextrin. In some embodiments, the ophthalmic composition has cyclodextrin as the sole or only pharmaceutically active agent.

In some embodiments, a method of treating eye allergy or allergic conjunctivitis comprises topically administering to the eye of a subject in need thereof a therapeutically effective amount of an ophthalmic composition consisting essentially of a cyclodextrin. In some embodiments, a method of treating eye allergy or allergic conjunctivitis comprises topically administering to an eye of a subject in need thereof a therapeutically effective amount of an ophthalmic composition consisting essentially of a cyclodextrin and one or more of ophthalmic pharmaceutically acceptable excipients.

In some embodiments, the allergic conjunctivitis treated is seasonal allergic conjunctivitis.

In some embodiments, the allergic conjunctivitis treated is perennial allergic conjunctivitis.

In some embodiments, the allergic conjunctivitis treated is vernal keratoconjunctivitis.

In some embodiments, the allergic conjunctivitis treated is atopic keratoconjunctivitis.

In some embodiments, the eye allergy or allergic conjunctivitis selected for treatment with the cyclodextrin or ophthalmic composition thereof is mediated by or suspected of being mediated by an eye allergen associated with, by way of example and not limitation, pollen, e.g., pollen originating from trees, grass, ragweed; perfumes, in particular organic compounds in perfume; cosmetics, in particular organic compounds in cosmetics; air pollution, including volatile organic compounds, particularly aromatic volatile organic compounds; eye allergens associated with dust mites; and eye allergens associated with insects, e.g., cockroaches.

In some embodiments, the eye allergy or allergic conjunctivitis selected for treatment with the cyclodextrin or ophthalmic composition thereof is mediated by or suspected of being mediated by a perennial allergen, such as animal dander, e.g., dog dander, cat dander, rodent dander; insect allergen, e.g., cockroach; and dust mite allergen. In some embodiments, the eye allergy or allergic conjunctivitis selected for treatment with the cyclodextrin or ophthalmic composition thereof is mediated by or suspected of being mediated by a grass allergen, such as allergens associated with grasses such as, among others, Bahia, Bermuda, Johnson, Orchard, Reed Canary, Meadow Fescue, Ryegrass, Kentucky Bluegrass, Velvet and Timothy grass. In some embodiments, the eye allergy or allergic conjunctivitis selected for treatment with the cyclodextrin or ophthalmic composition thereof is mediated by or suspected of being mediated by a tree allergen, such as allergens associated with, among others, Acacia, Alder (White, Taq, Smooth), Ash (Arizona, Green, Red), Birch (White, Red, River, Black, Sweet), Juniper (Oneseed, Pinchot, Utah, Western), Oak (White, Black, Bur, Scrub), and Maple (Sugar, Hard, Soft, Silver, Red).

In another aspect, cyclodextrin is used as prophylactic treatment to prevent or ameliorate the onset of physiologic responses to an eye allergen. In some embodiments, a method of prophylactic treatment to prevent or ameliorate onset of eye allergy or allergic conjunctivitis comprises administering to a subject in need thereof a therapeutically effective amount of a cyclodextrin, or a composition comprising a cyclodextrin.

In some embodiments, the method of prophylactic treatment to prevent or ameliorate onset of eye allergy or allergic conjunctivitis comprises topically administering to an eye of a subject in need thereof a therapeutically effective amount of a cyclodextrin, or an ophthalmic composition comprising a cyclodextrin. In some embodiments, the cyclodextrin, or an ophthalmic composition thereof, is topically administered to the eye prior to the occurrence of any symptoms of eye allergy or allergic conjunctivitis. In some embodiments, the cyclodextrin, or an ophthalmic composition thereof is topically administered to prevent one or more symptoms of eye allergy or allergic conjunctivitis, such as preventing one or more of ocular itching, redness, chemosis, and lid swelling, In some embodiments, the cyclodextrin is administered prophylactically as the sole or only pharmaceutically active agent for preventing or ameliorating the onset of eye allergy, as manifested as allergic conjunctivitis. In some embodiments, the cyclodextrin is substantially free of inclusion complexes with a pharmaceutically active agent. In some embodiments, the ophthalmic composition comprising the cyclodextrin for use in prophylactic treatment is substantially free of a pharmaceutically active agent which is capable of forming an inclusion complex with the cyclodextrin. In particular, the cyclodextrin or the ophthalmic composition thereof is substantially free of an ophthalmic pharmaceutically active agent capable of forming an inclusion complex with the cyclodextrin. In some embodiments, the ophthalmic composition for prophylactic treatment has cyclodextrin as the sole or only pharmaceutically active agent.

In some embodiments, a method of prophylactic treatment to prevent or ameliorate the onset of eye allergy or allergic conjunctivitis comprises topically administering to the eye of a subject in need thereof a therapeutically effective amount of an ophthalmic composition consisting essentially of a cyclodextrin. In some embodiments, a method of prophylactic treatment to prevent or ameliorate the onset of eye allergy or allergic conjunctivitis comprises topically administering to the eye of a subject in need thereof a therapeutically effective amount of an ophthalmic composition consisting essentially of a cyclodextrin and one or more of ophthalmic pharmaceutically acceptable excipients.

In some embodiments, the subject for prophylactic treatment with the cyclodextrin has been previously determined to have (i.e., previously diagnosed) or be susceptible or sensitive to an eye allergen. In some embodiments, the subject for prophylactic treatment with the cyclodextrin has been previously determined to have (i.e., previously diagnosed) or be susceptible or sensitive to an eye allergen associated with, by way of example and not limitation, pollen, e.g., pollen originating from trees, grass, ragweed; perfumes, in particular organic compounds in perfume; cosmetics, in particular organic compounds in cosmetics; air pollution, including volatile organic compounds, particularly aromatic volatile organic compounds; eye allergens associated with dust mites; and eye allergens associated with insects, e.g., cockroaches.

In some embodiments, the subject for prophylactic treatment with the cyclodextrin has been previously determined to have (i.e., previously diagnosed) or be susceptible or sensitive to a perennial allergen, such as animal dander, e.g., dog dander, cat dander, rodent dander; insect allergen, e.g., cockroach; and dust mite allergen. In some embodiments, the subject for prophylactic treatment with the cyclodextrin has been previously determined to have (i.e., previously diagnosed) or be susceptible to an allergic reaction to a grass allergen, such as allergens associated with grasses such as Bahia, Bermuda, Johnson, Orchard, Reed Canary, Meadow Fescue, Ryegrass, Kentucky Bluegrass, Velvet and Timothy grass. In some embodiments, the subject for prophylactic treatment with the cyclodextrin has been previously determined to have (i.e., previously diagnosed) or be susceptible or sensitive to a tree allergen, such as allergens associated with, among others, Acacia, Alder (White, Taq, Smooth), Ash (Arizona, Green, Red), Birch (White, Red, River, Black, Sweet), Juniper (Oneseed, Pinchot, Utah, Western), Oak (White, Black, Bur, Scrub), and Maple (Sugar, Hard, Soft, Silver, Red).

In another aspect, cyclodextrin can be used to bind or sequester allergens in the eye, and in some embodiments, inhibit or ameliorate the physiologic responses to an eye allergen. Accordingly, in some embodiments, a method of inhibiting or sequestering an eye allergen comprises topically administering to the eye of a subject an effective amount of a cyclodextrin, or an ophthalmic composition comprising a cyclodextrin. In some embodiments, the subject has been previously determined to have (i.e., previously diagnosed) or be susceptible or sensitive to an eye allergen.

In some embodiments, the cyclodextrin is administered as the sole or only pharmaceutically active agent to bind or sequester allergens in the eye. In some embodiments, the cycodextrin for inhibiting or sequestering an eye allergen is substantially free of inclusion complexes with a pharmaceutically active agent. In some embodiments, the ophthalmic composition comprising the cyclodextrin for inhibiting or sequestering an eye allergen is substantially free of a pharmaceutically active agent which is capable of forming inclusion complexes with the cyclodextrin. In particular, the cyclodextrin or the ophthalmic composition thereof for inhibiting or sequestering an eye allergen is substantially free of an ophthalmic pharmaceutically active agent capable of forming inclusion complexes with the cyclodextrin. That is, in some embodiments, the ophthalmic composition for inhibiting or sequestering an eye allergen has cyclodextrin as the sole or only active agent.

In some embodiments, a method of inhibiting or sequestering an eye allergen comprises topically administering to an eye of a subject an effective amount of a composition consisting essentially of cyclodextrin. In some embodiments, a method of inhibiting or sequestering an eye allergen comprises topically administering to an eye of a subject an effective amount of a composition consisting essentially of cyclodextrin, and one or more of an ophthalmic pharmaceutically acceptable excipient.

In some embodiments, the cyclodextrin or a composition thereof is used in an effective amount to inhibit and/or sequester an eye allergen associated with, by way of example and not limitation, pollen, e.g., pollen originating from trees, grass, ragweed; perfumes, in particular organic compounds in perfume; cosmetics, in particular organic compounds in cosmetics; air pollution, including volatile organic compounds, particularly aromatic volatile organic compounds; eye allergens associated with dust mites, and eye allergens associated with insects, e.g., cockroaches. In some embodiments, the cyclodextrin or a composition thereof is used in an effective amount to inhibit and/or sequester a lipid-associated or lipophilic eye allergen.

In some embodiments, the cyclodextrin or a composition thereof is used in an effective amount to inhibit and/or sequester a perennial allergen, such as animal dander, e.g., dog dander, cat dander, rodent dander; insect allergen, e.g., cockroach; and dust mite allergen. In some embodiments, the cyclodextrin or a composition thereof is used in an effective amount to inhibit and/or sequester a grass allergen, such as allergens associated with grasses such as Bahia, Bermuda, Johnson, Orchard, Reed Canary, Meadow Fescue, Ryegrass, Kentucky Bluegrass, Velvet and Timothy grass. In some embodiments, the cyclodextrin or a composition thereof is used in an effective amount to inhibit and/or sequester a tree allergen, such as allergens associated with, among others, Acacia, Alder (White, Taq, Smooth), Ash (Arizona, Green, Red), Birch (White, Red, River, Black, Sweet), Juniper (Oneseed, Pinchot, Utah, Western), Oak (White, Black, Bur, Scrub), and Maple (Sugar, Hard, Soft, Silver, Red).

In another aspect, the cyclodextrin or composition thereof can be used to bind, sequester, or inhibit toxic aldehydes formed in the eye, and/or reaction products of the toxic aldehydes, in particular, a toxic aldehyde in the eye other than lipofuscin or A2E. Accordingly, in some embodiments, a method of binding, sequestering, deactivating, or inhibiting a toxic aldehyde compound in the eye comprises topically administering to the eye of a subject an effective amount of a cyclodextrin, or a composition comprising a cyclodextrin. In some embodiments, the toxic aldehyde compound is a free aldehyde compound or a reaction product thereof. In particular, the toxic aldehyde or a reaction product thereof is associated with allergic conjunctivitis or an allergic reaction in the eye.

In some embodiments, the method of binding, sequestering, deactivating, or inhibiting a toxic aldehyde compound in the eye comprises topically administering to the eye of a subject an effective amount of a cyclodextrin, or a composition comprising a cyclodextrin, wherein the subject has been previously determined to have (i.e., previously diagnosed) or be susceptible or sensitive to an eye allergen.

In some embodiments, the cyclodextrin is administered as the sole or only pharmaceutically active agent for binding, sequestering, deactivating, or inhibiting a toxic aldehyde. In some embodiments, the cyclodextrin is substantially free of inclusions complexes with a pharmaceutically active agent. In some embodiments, the composition comprising the cyclodextrin for use in binding, sequestering, deactivating, or inhibiting a toxic aldehyde is substantially free of a pharmaceutically active agent capable of forming inclusion complexes with the cyclodextrin. In particular, the cyclodextrin or composition thereof is substantially free of an ophthalmic pharmaceutically active agent capable of forming inclusion complexes with the cyclodextrin. In some embodiments, the ophthalmic composition for binding, sequestering, deactivating, or inhibiting a toxic aldehyde has cyclodextrin as the sole or only active agent.

In some embodiments, the cyclodextrin or composition comprising a cyclodextrin can be used to reduce or treat inflammation in the eye associated with allergic conjunctivitis and/or an eye allergy. Thus, in some embodiments, a method of reducing or treating inflammation in the eye comprises topically administering to the eye of a subject in need thereof a therapeutically effective amount of a cyclodextrin, or an ophthalmic composition comprising a cyclodextrin, wherein the inflammation is associated with an eye allergy or allergic conjunctivitis. Treatment of eye inflammation associated with eye allergies is supported by the clinical trials data herein. In addition, cyclodextrins have been suggested to form inclusion complexes with a mediator of inflammatory response, i.e., arachidonic acid (Everest-Todd, M. 1998, Proceedings of the Eighth International Symposium on Cyclodextrins, pp. 495-498).

In some embodiments, the cyclodextrin is administered as the sole or only pharmaceutically active agent for reducing or treating inflammation in the eye. In some embodiments, the cyclodextrin is substantially free of inclusion complexes with a pharmaceutically active agent. In some embodiments, the composition comprising the cyclodextrin for reducing or treating inflammation in the eye is substantially free of a pharmaceutically active agent capable of forming inclusion complexes with the cyclodextrin. In particular, the cyclodextrin or composition thereof is substantially free of an ophthalmic pharmaceutically active agent capable of forming inclusion complexes with the cyclodextrin. In some embodiments, the ophthalmic composition for reducing or treating eye inflammation associated with allergic conjunctivitis or eye allergies has cyclodextrin as the sole or only pharmaceutically active agent.

In some embodiments, the method of reducing or treating inflammation in the eye comprises topically administering to the eye of a subject a therapeutically effective amount of a cyclodextrin, or a composition comprising a cyclodextrin, wherein the subject has been previously determined to have (i.e., previously diagnosed) or be susceptible or sensitive to an eye allergen.

Determining whether a subject has been previously identified or determined to have or be susceptible to an allergic reaction upon exposure to an eye allergen can use standard procedures available to a person of skill in the art. Generally, this includes a review of the medical history, past effectiveness of anti-histamines or mast cell stabilizers in reducing or ameliorating allergic symptoms in the eye, medical examination of the eyes, and/or testing for indicators of an allergic reaction. For example, eyes can be examined for symptoms of an allergic reaction, such as itchy eyes, swollen blood vessels, watery secretions, swollen eye lids, and/or testing a sample of the conjunctiva for presence of eosinophils. In some embodiments, a "skin scratch" test is used to determine a subject's reaction to a sample of a suspected eye allergen or a panel of suspected eye allergens (e.g., Allergy Matrix Test).

In some embodiments, the cyclodextrin for use in the methods and compositions herein are cyclic oligosaccharides, particularly cyclic oligosaccharides in which glucopyranose units are linked by α-(1,4) bonds to form a torus like structure, where the size of the internal cavity is determined, in part, by the number of glucopyranose units. The number of glucopyranose units in the cyclodextrin can vary, for example from 6 to 12 or higher. Structural studies of such cyclodextrins indicate that the secondary hydroxyl groups (e.g., C2 and C3) of the glucopyranose units are located on the wider edge of the toroidal structure, while the primary hydroxyl groups (e.g., C6) are on the other edge. The apolar C3 and C5 hydrogens and also the ether like oxygen atoms face the inside of the torus structure. The spatial distribution of the polar and apolar groups result in a molecule having a relatively hydrophilic exterior, which allows the cyclodextrin to be soluble in water, and an internal hydrophobic matrix, which can accommodate and form inclusion complexes with various hydrophobic guest molecules. The number of guest molecules accommodated within the internal hydrophobic cavity can vary, for example from 1 to 3 guest molecules. In some instances, multiple number of cyclodextrins can combine to form inclusion complexes with a single guest molecule. Common types of cyclodextrins include α-cyclodextrin, β-cyclodextrin, and γ-cyclodextrin. α-, and γ-cyclodextrin have 6, 7 and 8α-(1,4) linked glycosyl units, respectively. The α-, β-, and γ-cyclodextrins are naturally occurring cyclodextrins. Other useful cyclodextrins include, among others, maltosyl, glucosyl, and maltotriosyl derivatives of β- and γ-cyclodextrins (see, e.g., U.S. Pat. No. 5,024,998). Other useful cyclodextrin derivatives have been synthesized by modification of the hydroxyl groups on the glycosyl units, for example by amination, esterification or etherification. These modifications to the cyclodextrin can result in changes to the cavity volume, solubility, and differential reactivity with guest molecules. In some embodiments, a composition comprising a cyclodextrin is a cyclodextrin other than $6^A,6^B,6^C,6^D,6^E,6^F,6^G,6^H$-Octakis-S-(2-carboxyethyl)-$6^A,6^B,6^C,6^D,6^E,6^F,6^G,6^H$-octathio-γ-cyclodextrin (i.e., S-2-carboxyethyl-octathio-γ-cyclodextrin, also referred to as sugammadex) and/or $6^A,6^B,6^C,6^D,6^E,6^F,6^G$-Heptakis-S-(2-carboxyethyl)-$6^A,6^B,6^C,6^D,6^E,6^F,6^G$-heptathio-γ-cyclodextrin (i.e., S-2-carboxyethyl-heptathio-γ-cyclodextrin). In some embodiments, a composition where the cyclodextrin is the sole or only pharmaceutically active agent, the cyclodextrin is not 2-carboxyethyl-octathio-γ-cyclodextrin. In some embodiments, a composition where the cyclodextrin is the sole or only pharmaceutically active agent, the cyclodextrin is not 2-carboxyethyl-heptathio-γ-cyclodextrin.

In some embodiments, the cyclodextrin for use in the methods and compositions is selected from α-cyclodextrin, β-cyclodextrin, γ-cyclodextrin, derivatives thereof, and combinations thereof. In particular, the cyclodextrin for use in the methods is selected from β-cyclodextrin, γ-cyclodextrin, derivatives thereof, and combinations thereof.

In some embodiments, the cyclodextrin or derivative thereof is selected from carboxyalkyl cyclodextrin, hydroxyalkyl cyclodextrin, sulfoalkylether cyclodextrin, and alkyl cyclodextrin. In various embodiments, the alkyl group in the cyclodextrin is methyl, ethyl, propyl, butyl, pentyl, or hexyl.

In some embodiments, the cyclodextrin is α-cyclodextrin or a derivative thereof. In some embodiments, the α-cyclodextrin or a derivative thereof is selected from carboxyalkyl-α-cyclodextrin, hydroxyalkyl-α-cyclodextrin, sulfoalkylether-α-cyclodextrin, alkyl-α-cyclodextrin, and combinations thereof. In some embodiments, the alkyl group in the α-cyclodextrin derivative is methyl, ethyl, propyl, butyl, pentyl or hexyl.

In some embodiments, the cyclodextrin is β-cyclodextrin or a derivative thereof. In some embodiments, the β-cyclodextrin or derivative thereof is selected from carboxyalkyl-β-cyclodextrin, hydroxyalkyl-β-cyclodextrin, sulfoalkylether-β-cyclodextrin, alkyl-β-cyclodextrin, and combinations thereof. In some embodiments, the alkyl group in the β-cyclodextrin derivative is methyl, ethyl, propyl, butyl, pentyl or hexyl.

In some embodiments, the β-cyclodextrin or a derivative thereof is hydroxyalkyl-β-cyclodextrin or sulfoalkylether-β-cyclodextrin. In some embodiments, the hydroxyalkyl-β-cyclodextrin is hydroxypropyl-β-cyclodextrin. In some embodiments, the sulfoalkylether-β-cyclodextrin is sulfobutylether-β-cyclodextrin. In some embodiments, β-cyclodextrin or a derivative thereof is alkyl-β-cyclodextrin, in particular methyl-β-cyclodextrin. In some embodiments using methyl-β-cyclodextrin, the β-cyclodextrin is randomly methylated β-cyclodextrin.

In some embodiments, the cyclodextrin is γ-cyclodextrin or a derivative thereof. In some embodiments, the γ-cyclodextrin or derivative thereof is selected from carboxyalkyl-γ-cyclodextrin, hydroxyalkyl-γ-cyclodextrin, sulfoalkylether-γ-cyclodextrin, and alkyl-γ-cyclodextrin. In some embodiments, the alkyl group in the γ-cyclodextrin derivative is methyl, ethyl, propyl, butyl, pentyl, or hexyl. In some embodiments, the γ-cyclodextrin or derivative thereof is hydroxyalkyl-γ-cyclodextrin or sulfoalkylether-γ-cyclodextrin. In some embodiments, the hydroxyalkyl-γ-cyclodextrin is hydroxypropyl-γ-cyclodextrin, such as 2-hydroxypropyl-γ-cyclodextrin. In some embodiments, the γ-cyclodextrin or derivative thereof is S-2-carboxyalkyl-thio-γ-cyclodextrin, such as S-2-carboxyethyl-thio-γ-cyclodextrin.

In some embodiments, various salts of the cyclodextrin or salts of the cyclodextrin derivative can be used in the methods herein. In some embodiments, the salts are pharmaceutically acceptable salt(s), which refers to those salts of compounds, i.e., cyclodextrin, that are safe and effective for use in mammals and that possess the desired biological activity. Pharmaceutically acceptable salts include salts of acidic or basic groups present in the cyclodextrins. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, and p-toluenesulfonate salts. Suitable base salts include, but are not limited to, aluminum, calcium, lithium, magnesium, potassium, sodium, zinc, and diethanolamine salts. In some embodiments, the cyclodextrin is in the form of a sodium or potassium salt. Guidance on suitable pharmaceutically acceptable salts and their application to drug formulations can be found in various references, such as Remington's Pharmaceutical Sciences, 17th Ed., Mack Publishing Company, Easton, Pa., 1985, and Berge, et al., 1977, "Pharmaceutical Salts," *J Pharm Sci.* 66:1-19, both of which are incorporated herein by reference.

In some embodiments, the cyclodextrin is a mixture of cyclodextrins. Such mixtures can be a combination of: α-cyclodextrin and β-cyclodextrin, including combinations of α-cyclodextrin and β-cyclodextrin derivatives; α-cyclodextrin and γ-cyclodextrin, including combinations of α-cyclodextrin and γ-cyclodextrin derivatives; β-cyclodextrin and γ-cyclodextrin, including combinations of β-cyclodextrin and γ-cyclodextrin derivatives; or α-cyclodextrin, β-cyclodextrin, and γ-cyclodextrin, including combinations of α-cyclodextrin, β-cyclodextrin, and γ-cyclodextrin derivatives.

In the methods and compositions herein, the cyclodextrin or derivative thereof is prepared to provide a therapeutically effective amount for, among others, (a) treating eye allergy or allergic conjunctivitis; (b) ameliorating or mitigating one or more symptoms of eye allergy or allergic conjunctivitis; (c) treating inflammation associated with eye allergy or allergic conjunctivitis; or (d) prophylactic treatment for preventing or ameliorating the onset of eye allergy or allergic conjunctivitis. In some embodiments, the cyclodextrin or derivative thereof is prepared to provide an effective amount for sequestering, binding, and/or inhibiting an eye allergen. In some embodiments, the cyclodextrin or derivative thereof is prepared to provide an effective amount for sequestering, binding, and/or inhibiting a toxic aldehyde or a reaction product thereof in the eye, particularly a free aldehyde associated with an allergic response in the eye.

In some embodiments, the cyclodextrin (e.g., α-, β-, or γ-cyclodextrin), such as in a composition, in particular an ophthalmic solution, for use in the methods described herein is present at about 0.1% to about 30% w/v, about 0.1% to about 25% w/v, about 0.1% to about 20% w/v, about 0.2% to about 15% w/v, about 0.5% to about 10% w/v, about 0.5% to about 7.5% w/v, or about 1% to about 5% w/v. For example, an exemplary cyclodextrin is sulfobutylether-β-cyclodextrin, which can be present at about 0.1% to about 30% w/v, about 0.1% to about 25% w/v, about 0.1% to about 20% w/v, about 0.2% to about 15% w/v, about 0.5% to about 10% w/v, about 0.5% to about 7.5% w/v, or about 1% to about 5% w/v. In some embodiments, an exemplary cyclodextrin is hydroxypropyl-β-cyclodextrin, which can be present at about 0.1% to about 30% w/v, about 0.1% to about 25% w/v, about 0.1% to about 20% w/v, about 0.2% to about 15% w/v, about 0.5% to about 10% w/v, about 0.5% to about 7.5% w/v, or about 1% to about 5% w/v. In some embodiments, an exemplary cyclodextrin is hydroxypropyl-γ-cyclodextrin, which can be present at about 0.1% to about 30% w/v, about 0.1% to about 25% w/v, about 0.1% to about 20% w/v, about 0.2% to about 15% w/v, about 0.5% to about 10% w/v, about 0.5% to about 7.5% w/v, or about 1% to about 5% w/v.

In embodiments where mixtures of cyclodextrins are used, for example mixtures of sulfobutylether-β-cyclodextrin and hydroxypropyl-β-cyclodextrin, the total amount of cyclodextrin can be present at about 0.1% to about 30% w/v, about 0.1% to about 25% w/v, about 0.1% to about 20% w/v, about 0.2% to about 15% w/v, about 0.5% to about 10% w/v, about 0.5% to about 7.5% w/v, or about 1% to about 5% w/v.

In some embodiments, the cyclodextrin, such as in a composition thereof, in particular an ophthalmic solution, for use in the methods herein is present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 12% w/v, about 14% w/v, about 16% w/v, about 18% w/v, about 20% w/v, about 25% w/v, or about 30% w/v. For example, a β-cyclodextrin, e.g., sulfobutylether-β-cyclodextrin, can be present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 12% w/v, about 14% w/v, about 16% w/v, about 18% w/v, about 20% w/v, about 25% w/v, or about 30% w/v. In some embodiments, a β-cyclodextrin, e.g., hydroxypropyl-β-cyclodextrin, can be present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 12% w/v, about 14% w/v, about 16% w/v, about 18% w/v, about 20% w/v, about 25% w/v, or about 30% w/v. In some embodiments, a γ-cyclodextrin, e.g., hydroxypropyl-γ-cyclodextrin, can be present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 12% w/v, about 14% w/v, about 16% w/v, about 18% w/v, about 20% w/v, about 25% w/v, or about 30% w/v.

In some embodiments where mixtures of cyclodextrins are used, for example mixtures of sulfobutylether-β-cyclodextrin and hydroxypropyl-β-cyclodextrin, the total amount of cyclodextrin can be present at about 0.1%, about 0.2%, about 0.5%, about 1%, about 2%, about 3%, about 4%, about 5%, about 6%, about 7%, about 8%, about 9%, about 10%, about 12%, about 14%, about 16%, about 18%, about 20% w/v, about 25% w/v, or about 30% w/v.

It is to be understood that while the cyclodextrin levels (e.g., concentration) for administration are given for exemplary cyclodextrins sulfobutylether-β-cyclodextrin, hydroxypropyl-β-cyclodextrin, and hydroxypropyl-γ-cyclodextrin, equivalent concentrations of the other specific cyclodextrins can be readily determined by the person of skill in the art.

As discussed herein, in some embodiments of the methods, cyclodextrin is administered as the sole or only active agent. In some embodiments, the cyclodextrin or composition thereof, particularly an ophthalmic solution, for use in the methods is substantially free of a pharmaceutically active agent that is capable of forming an inclusion complex with the cyclodextrin. In some embodiments and as discussed herein, the pharmaceutically active agent is present at a concentration below that which is required to provide a therapeutic benefit. In some embodiments, the cyclodextrin or composition comprising a cyclodextrin, particularly an ophthalmic solution, is absent a pharmaceutically active agent which forms inclusion complexes with the cyclodextrin. In some embodiments, the cyclodextrin composition, particularly an ophthalmic solution, has cyclodextrin as the sole or only pharmaceutically active agent.

However, it is to be understood that in some embodiments, the cyclodextrin, or compositions thereof, such as an ophthalmic solution, for use in the methods can have a pharmaceutically active agent in addition to the cyclodextrin, particularly wherein the pharmaceutically active agent is effective in treating an eye allergy, such as eye allergy manifested as allergic conjunctivitis. In some embodiments, the pharmaceutically active agent present with the cyclodextrin does not form a substantial level of inclusion complexes with the cyclodextrin. For example, the solubility or therapeutic efficacy of the pharmaceutical agent is not affected by presence of cyclodextrin. In some embodiments, the pharmaceutically active agent does not form inclusion complexes with the cyclodextrin.

In some embodiments, the cyclodextrin, or composition thereof, such as an ophthalmic solution, for use in the methods can have a pharmaceutically active agent, including a pharmaceutically active agent which is capable of forming inclusion complexes with the cyclodextrin. In particular, the cyclodextrin or compositions thereof can have an ophthalmic pharmaceutically active agent for treating an eye allergy or allergic conjunctivitis, where the ophthalmic pharmaceutically active agent forms inclusion complexes with the cyclodextrin. In some embodiments, the cyclodextrin or derivative thereof is present in an amount sufficient to provide an effective amount (e.g., concentration) of free, uncomplexed cyclodextrin to provide a therapeutic benefit in addition to the therapeutic benefit provided by the pharmaceutically active agent. For example, the cyclodextrin or derivative thereof is present in an amount (e.g., concentration) sufficient to provide an effective amount (or concentration) of free, uncomplexed cyclodextrin to sequester, bind, and/or inhibit an eye allergen and/or a toxic aldehyde associated with an allergic response in the eye, in addition to the amount (or concentration) needed to enhance solubility and/or bioavailability of the pharmaceutically active agent. Pharmaceutically active agents formulated with cyclodextrin include compounds useful for treating allergic conjunctivitis, for example mast cell stabilizers, steroids, antihistamines, non-steroidal anti-inflammatory drugs (NSAIDs), and aldehyde trapping compounds. Exemplary steroids include prednisolone, dexamethasone, and fluorometholone. Exemplary antihistamines include, among others, levocabastine, olopatadine, and ketotifen fumarate. Aldehyde trapping compounds for use with cyclodextrins are disclosed in WO2014116836; WO2006127945; WO2011072141; WO2014100425; and WO2014116593, all of which are incorporated by reference herein. In some embodiments, the exemplary aldehyde trapping compound is the compound of structure (I) above, which as shown in the clinical trials, had a greater effect in treating and/or reducing symptoms of allergic conjunctivitis in a formulation with cyclodextrin than cyclodextrin alone (i.e., vehicle only). Thus, for each and every embodiment of the cyclodextrin compositions described herein, it is also intended to include embodiments of compositions in which the compound of structural formula (I) is present as a pharmaceutically active agent, particularly in a therapeutically effective amount for treating allergic conjunctivitis, eye allergies, and/or eye allergy associated inflammation of the eye. In some embodiments, the amount of the compound of structural formula (I) in a topical ophthalmic formulation with a cyclodextrin is present at least about 0.05% w/v, 0.1% w/v, about 0.2% w/v, about 0.3%, w/v, about 0.4% w/v, about 0.5% w/v, about 0.6% w/v, about 0.7% w/v, about 0.8% w/v, about 0.9% w/v, about 1% w/v, about 1.5% w/v, about 2% w/v, about 3% w/v, about 4% w/v, or about 5% w/v. In some embodiments, the amount of the compound of structural formula (I) for a topical formulation is present at about 0.05% w/v to about 5% w/v, about 0.1% w/v to about 5% w/v, about 0.2% w/v to about 4% w/v, about 0.3% to about 3% w/v, about 0.4% w/v to about 2% w/v, or about 0.5% w/v to about 1.5% w/v. In some embodiments, the cyclodextrin is a β-cyclodextrin, γ-cyclodextrin, derivatives thereof, and combinations thereof. In some embodiments, the β-cyclodextrin or derivative thereof is hydroxyalkyl-β-cyclodextrin or sulfoalkylether-β-cyclodextrin, particularly hydroxypropyl-β-cyclodextrin or sulfobutylether-β-cyclodextrin. In some embodiments, the γ-cyclodextrin or derivative thereof is hydroxyalkyl-γ-cyclodextrin or sulfoalkylether-γ-cyclodextrin, particularly hydroxypropyl-γ-cyclodextrin or sulfobutylether-γ-cyclodextrin. The amounts of the cyclodextrin which can be used with compound of formula (I) are the amounts described above. In some embodiments, the cyclodextrin is present at about 0.1% to about 30% w/v, about 0.1% to about 25% w/v, about 0.1% to about 20% w/v, about 0.2% to about 15% w/v, about 0.5% to about 10% w/v, about 0.5% to about 7.5% w/v, or about 1% to about 5% w/v, for example, for any of the concentration of the compound of structural formula (I) described above. In some embodiments, the cyclodextrin is present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 12% w/v, about 14% w/v, about 16% w/v, about 18% w/v, about 20% w/v, about 25% w/v, or about 30% w/v, for example, for any of the concentration of the compound of structural formula (I) described above.

In some embodiments, the cyclodextrin or derivative thereof is present at least in 1 mole (molar) excess of the amount of the pharmaceutically activity agent which forms inclusion complexes with the cyclodextrin. In some embodiments, the cyclodextrin or derivative thereof relative to the amount of the pharmaceutically activity agent is present at least about 1 mole (molar) excess to about 500 mole (molar) excess, about 1.5 mole (molar) excess to about 100 mole (molar) excess; about 2 mole (molar) excess to about 75 mole (molar) excess; about 5 mole (molar) excess to about 50 mole (molar) excess; about 8 mole (molar) excess to about 40 mole (molar) excess; or about 10 mole (molar) excess to about 30 mole (molar) excess.

In some embodiments, the cyclodextrin or derivative thereof relative to the amount of the pharmaceutically activity agent which forms inclusion complexes with cyclodextrin is present at least in about 1.5 mole (molar) excess, 2 mole (molar) excess, 3 mole (molar) excess, 4 mole (molar) excess, 5 mole (molar) excess, 6 mole (molar) excess, 7 mole (molar) excess, 8 mole (molar) excess, 9 mole (molar) excess, 10 mole (molar) excess, 15 mole (molar) excess, 20 mole (molar) excess, 30 mole (molar) excess, 40 mole (molar) excess, 50 mole (molar) excess, 75 mole (molar) excess, 100 mole (molar) excess, 200 mole (molar) excess, 300 mole (molar) excess, 400 mole (molar) excess, or 500 mole (molar) excess.

In some embodiments, the mole (or molar) ratio of the amount of cyclodextrin or derivative thereof to the amount of the pharmaceutically active agent which forms inclusion complexes with the cyclodextrin is at least about 2:1 to about 500:1; about 2:1 to about 400:1; about 2:1 to about 300:1; about 2:1 to about 200:1; about 5:1 to about 150:1; about 10:1 to about 100:1; about 15:1 to about 50:1; or about 20:1 to about 40:1.

In some embodiments, the mole (or molar) ratio of the amount of cyclodextrin or derivative thereof to the amount of the pharmaceutically active agent which forms inclusion complexes with cyclodextrin is at least about 2:1, about 3:1, about 4:1, about 5:1, about 6:1, about 7:1, about 8:1, about 9:1, about 10:1, about 15:1, about 20:1, about 30:1, about 40:1, about 50:1, about 100:1, about 150:1, about 200:1, about 300:1, about 400:1, or about 500:1.

In some embodiments where a pharmaceutically active agent capable of forming an inclusion complex is present with the cyclodextrin, a first cyclodextrin can be used to enhance the solubility of the pharmaceutically active agent, and a second cyclodextrin different from the first cyclodextrin can be used to effect an additional therapeutic effect, for example by binding, sequestering, and/or inhibiting an eye allergen and/or a toxic aldehyde associated with eye allergy. For example, olopatadine, used for treating allergic conjunctivitis, is formulated with hydroxypropyl-γ-cyclodextrin) to improve solubility (see, e.g., Torklidsen et al., 2015, *Clin Ophthalmol*. 9:1703-1713). In such instances, a second cyclodextrin, different from the hydroxypropyl-γ-cyclodextrin, such as methyl-β-cyclodextrin or sulfobutylether-β-cyclodextrin can be present in addition to the hydroxypropyl-γ-cyclodextrin and olopatadine, for treating allergic conjunctivitis. In some embodiments, a method for treating allergic conjunctivitis comprises administering to a subject in need thereof a therapeutically effective amount of a composition comprising: a first cyclodextrin, an ophthalmic pharmaceutically active compound for treating allergic conjunctivitis, wherein the first cyclodextrin enhances the solubility of the ophthalmic pharmaceutically active compound, and a second cyclodextrin different from the first cyclodextrin, wherein the second cyclodextrin provides an additional therapeutic benefit. In some embodiments, the additional therapeutic benefit in the eye allergy context is sequestering, binding, and/or inhibiting an eye allergen and/or a toxic aldehyde associated with an allergic response in the eye.

In various embodiments, the cyclodextrin compositions can be prepared as solutions, suspensions, ointments, gels and other dosage forms administration, particularly for topical administration. For ophthalmic topical administration, the dosage form includes solutions, ointments, gels (e.g., viscous or semi-viscous), emulsions, suspensions and solid eye drops and the like. In particular, aqueous solutions are generally preferred, based on ease of formulation and administration by a patient or medical professional. In some embodiment, the cyclodextrin compositions are lyophilized formulations.

In some embodiments, the cyclodextrin or composition thereof for use in the methods is formulated with one or more ophthalmic pharmaceutically acceptable additive or excipient. Accordingly, in some embodiments, an ophthalmic composition containing the cyclodextrin or derivative thereof further comprises one or more of an ophthalmic pharmaceutically acceptable additive or excipient.

In some embodiments, the one or more ophthalmic pharmaceutically acceptable additive or excipient is selected from a tonicity agent, preservative, buffering agent, wetting agent, viscosity enhancing agent, lubricating agent, chelating agent, and antioxidant. In some embodiments, the additive or excipient selected does not form substantial levels of inclusion complexes with cyclodextrin or derivatives thereof.

In some embodiments, the cyclodextrin compositions can have one or more tonicity agents, which can be used to adjust the tonicity of the composition, for example, to the tonicity of natural tears. Suitable tonicity agents include, by way of example and not limitation, dextrans (e.g., dextran 40 or 70), dextrose, glycerin, potassium chloride, propylene glycol, and sodium chloride. Equivalent amounts of one or more salts made up of cations, for example, such as potassium, ammonium and anions such as chloride, citrate, ascorbate, borate, phosphate, bicarbonate, sulfate, thiosulfate, bisulfate, the salts sodium bisulfate and ammonium sulfate, can also be used. The amount of tonicity agent will vary, depending on the particular agent to be added. In general, however, the compositions can have a tonicity agent in an amount sufficient to cause the final composition to have an ophthalmically acceptable osmolarity. In some embodiments, the cyclodextrin compositions have an osmolality of about 200 to about 1000 mOsm/L or about 200 to about 500 mOsm/L, or any specific value within said ranges (e.g., 200 mOsm/L, 210 mOsm/L, 220 mOsm/L, 230 mOsm/L, 240 mOsm/L, 250 mOsm/L, 260 mOsm/L, 270 mOsm/L, 280 mOsm/L, 290 mOsm/L, 300 mOsm/L, 310 mOsm/L, 320 mOsm/L, 330 mOsm/L, 340 mOsm/L, 350 mOsm/L, 360 mOsm/L, 370 mOsm/L, 380 mOsm/L, 390 mOsm/L or 400 mOsm/L). In a particular embodiment, the ophthalmic formulations are adjusted with a tonicity agent to an osmolality of ranging from about 250 to about 450 mOsm/L, or about 250 to about 350 mOsm/L.

In some embodiments, the cyclodextrin composition can have one or more preservatives, for example, to extend shelf life or limit bacterial growth in the solutions during storage as well as when administered therapeutically onto the eye. Preservatives that can be used, include, among others, benzalkonium chloride, benzethonium chloride, benzododecinium bromide, cetylpyridinium chloride, chlorobutanol, ethylenediamine tetracetic acid (EDTA), thimerosol, phenylmercuric nitrate, phenylmercuric acetate, methyl/propylparabens, phenylethyl alcohol, sodium benzoate, sodium propionate, sorbic acid, and sodium perborate. The amount of preservative in the solution can be a level that enhances the shelf life, limits bacterial growth, or otherwise preserves the ocular solution, with minimal toxicity to the eye tissues (see, e.g., The United States Pharmacopeia, 22nd rev., and The National Formulary, 17th Ed. Rockville, Md.). Levels of preservative suitable for use in the ocular formulations can be determined by the person skilled in the art. In some embodiments, the preservatives can be used at an amount of from about 0.001% to about 1.0% w/v. For example, the preservative is present from about 0.005% to about 0.05% w/v, 0.005% to about 0.04% w/v, 0.01% to about 0.03% w/v, 0.01% to about 0.02% w/v, or from about 0.01% to about 0.015% w/v. In some embodiments, the amount of preservative can be about 0.005% w/v, about 0.01% w/v, about 0.012% w/v, about 0.014% w/v, about 0.016% w/v, about 0.018% w/v, about 0.02% w/v, about 0.03% w/v, about 0.04% w/v, or about 0.05% w/v. In some embodiments, no preservatives are used in the compositions.

In some embodiments, the cyclodextrin composition can have one or more buffering agents for adjusting and/or maintaining the pH of the ocular solution at a specified pH range. Generally, buffer capacity should be large enough to maintain the product pH for a reasonably long shelf-life but also low enough to allow rapid readjustment of the product to physiologic pH upon administration. Generally, buffer capacities of from about 0.01 to 0.1 can be used for ophthalmic solutions, particularly at concentrations that provide sufficient buffering capacity and minimizes adverse effects, e.g., irritation, to the eye. Exemplary buffering agents include, by way of example and not limitation, various salts (e.g., sodium, potassium, etc.), acids or bases, where appropriate, of the following agents, including, among others, acetate, borate, phosphate, bicarbonate, carbonate, citrate, tetraborate, biphosphate, tromethamine, hydroxyethyl morpholine, and THAM (trishydroxymethyl-amino-methane). In some embodiments, the buffering agent can be present from about 0.01 mM to about 100 mM, about 0.05 mM to about 100 mM, about 0.5 mM to about 100 mM, from about 1 mM to about 50 mM, from about 1 mM to about 40 mM, from about 1 mM to about 30 mM, from about 1 mM to about 20 mM, or from about 1 mM to about 10 mM. In some embodiments, the buffering agent can be present at about 0.01 mM, about 0.05 mM, about 0.1 mM, about 0.2 mM, about 0.5 mM, about 1 mM, about 5 mM, about 10 mM, about 20 mM, about 30 mM, about 40 mM, about 50 mM, or about 100 mM.

In some embodiments, an exemplary buffering agent is phosphate, particularly sodium phosphate, which can be prepared by standard procedures, for example by mixing appropriate amounts of one or more monobasic phosphates, dibasic phosphates, and the like. In particular, useful phosphate buffers are prepared from phosphate salts of alkali and/or alkaline earth metals, such as sodium or potassium phosphate, including sodium monobasic phosphate, sodium dibasic phosphate, potassium monobasic phosphate, and potassium dibasic phosphate. In some embodiments, the phosphate buffer can be present from about 0.5 mM to about 100 mM, from about 1 mM to about 50 mM, from about 1 mM to about 40 mM, from about 1 mM to about 30 mM, from about 1 mM to about 20 mM, or from about 1 mM to about 10 mM. In some embodiments, the phosphate buffer can be present at about 0.5 mM, about 1 mM, about 5 mM, about 10 mM, about 20 mM, about 30 mM, about 40 mM, about 50 mM, or about 100 mM.

In some embodiments, the cyclodextrin compositions can have one or more wetting agents. Generally, wetting agents can hydrate and limit drying of the eye. Wetting agents generally are hydrophilic polymers, including, by way of example and not limitation, polysorbate 20 and 80, poloxamer 282, and tyloxapol. In some embodiments, wetting agents also include, among others, cellulose based polymers, such as hydroxypropylmethylcellulose (HPMC) and carboxymethylcellulose (CMC); polyvinylpyrrolidone; and polyvinyl alcohol. In some embodiments, the concentration of wetting agent, such as HPMC, ranges from about 0.1% to about 2% w/v, about 0.5% to about 1% w/v, or any specific value within the ranges. In some embodiments, the concentration of wetting agent, such as HPMC, ranges from about 0.1% to about 1.0% w/v, or any specific value within said range (e.g., 0.1-0.2%, 0.2-0.3%, 0.3-0.4%, 0.4-0.5%, 0.5-0.6%, 0.6-0.7%, 0.7-0.8%, 0.8-0.9%, 0.9-1.0%; about 0.2%, about 0.21%, about 0.22%, about 0.23%, about 0.24%, about 0.25%, about 0.26%, about 0.27%, about 0.28%, about 0.29%, about 0.30%, about 0.70%, about 0.71%, about 0.72%, about 0.73%, about 0.74%, about 0.75%, about 0.76%, about 0.77%, about 0.78%, about 0.79%, about 0.80%, about 0.81%, about 0.82%, about 0.83%, about 0.84%, about 0.85%, about 0.86%, about 0.87%, about 0.88%, about 0.89%, or about 0.90%).

In some embodiments, the cyclodextrin compositions can have one or more viscosity enhancing agents. The viscosity enhancing agent typically enhances the viscosity of the ocular solution to increase retention time of the solution on the eye, and in some instances, to provide a protective layer on the eye surface. Viscosity enhancing agents include, among others, carbopol gels, dextran 40 (molecular weight of 40,000 Daltons), dextran 70 (molecular weight of 70,000 Daltons), gelatin, glycerin, CMC, hydroxyethyl cellulose, HPMC, methylcellulose, ethylcellulose, polyethylene glycol, poloxamer 407, polysorbate 80, propylene glycol, polyvinyl alcohol, and polyvinylpyrrolidone (povidone), in various molecular weights and in various compatible combinations. In some embodiments, the ophthalmic compositions containing the cyclodextrin has a viscosity that ranges from about 10 to about 150 centipoise (cpi), about 15 to about 120 cpi, about 20 to about 90 cpi (or any specific value within said ranges). In some embodiments, the ophthalmic compositions containing the cyclodextrin has a viscosity that ranges from about 15 cpi to about 30 cpi, or any specific value within the range (i.e., about 15 cpi, about 16 cpi, about 17 cpi, about 18 cpi, about 19 cpi, about 20 cpi, about 20 cpi, about 22 cpi, about 23 cpi, about 24 cpi, about 25 cpi, about 26 cpi, about 27 cpi, about 28 cpi, about 29 cpi, about 30 cpi). In some embodiments, the ophthalmic compositions containing the cyclodextrin has a viscosity that ranges from about 70 cpi to about 90 cpi, or any specific value within said range (i.e., about 70 cpi, about 71 cpi, about 72 cpi, about 73 cpi, about 74 cpi, about 75 cpi, about 76 cpi, about 77 cpi, about 78 cpi, about 79 cpi, about 80 cpi, about 81 cpi, about 82 cpi, about 83 cpi, about 84 cpi, about 85 cpi, about 86 cpi, about 87 cpi, about 88 cpi, about 89 cpi or about 90 cpi). In particular, a viscosity of from about 25 to about 50 cps are suitable for ophthalmic solutions.

In some embodiments, the cyclodextrin compositions can have one or more lubricating agents. Ocular lubricants can approximate the consistency of endogenous tears and aid in natural tear build-up. Lubricating agents can include non-phospholipid and phospholipid-based agents. Ocular lubricants that are non-phospholipid based include, but are not limited to, propylene glycol; ethylene glycol; polyethylene glycol; hydroxypropylmethylcellulose; carboxymethylcellulose; hydroxypropylcellulose; dextrans, such as, dextran 70; water soluble proteins, such as gelatin; vinyl polymers, such as polyvinyl alcohol, polyvinylpyrrolidone, povidone; petrolatum; mineral oil; and carbomers, such as, carbomer 934P, carbomer 941, carbomer 940, and carbomer 974P. Non-phospholipid lubricants can also include compatible mixtures of any of the foregoing agents.

In some embodiments, the cyclodextrin compositions can include one or more antioxidants. Suitable antioxidants include, by way of example and not limitation, EDTA (e.g., disodium EDTA), sodium bisulphite, sodium metabisulphite, sodium thiosulfate, thiourea, and alpha-tocopherol.

In various embodiments, the pH of the cyclodextrin composition can be within 1.0 to 1.5 pH units from physiological pH, particularly the physiological pH in the external environment of the eye. The pH of human tears is approximately pH 7.4. Hence, the pH of the ophthalmic solution can be about 1.0 to 1.5 pH units above or below pH 7.4. In some embodiments, the pH of the ophthalmic solution is from about pH 6.0 to about pH 8.5. In some embodiments, the pH of the ophthalmic solution is from about pH 6.0 to about pH 8.0. In some embodiments, the pH of the ophthalmic solution is from about 6.5 to about 8.0. In some embodiments, the pH of the ophthalmic solution is from about 7.0 to about 8.0. In some embodiments, the pH of the ophthalmic solution is from about 7.0 to about 7.5. In some embodiments, the pH of the ophthalmic solution is about 6.5, about 7, about 7.5, about 8, or about 8.5. A person of skill in the art can select a pH that balances the stability of the cyclodextrin composition and the tolerability of the eye to differences in pH from the natural condition. As is well known in the art, the pH of the solution can be adjusted by use of appropriate buffering agents and/or with an appropriate base (e.g., sodium hydroxide) or acid (e.g., hydrochloric acid).

In the various embodiments of the methods, the subject to be treated is a mammal, for example a dog, a cat, a horse, or a rabbit. In some embodiments, the subject is a non-human primate, for example a monkey, chimpanzee, or gorilla. In some embodiments, the subject is a human, sometimes referred to herein as a patient.

In various embodiments, the cyclodextrin or compositions thereof are administered in an amount which is effective for the intended use, e.g., treating allergic conjunctivitis; to mitigate the signs and symptoms of allergic conjunctivitis; sequestering, binding and/or inhibiting eye allergens; sequestering, binding and/or inhibiting toxic aldehydes associated with allergic reactions in the eye; and/or treatment of inflammatory condition associated with eye allergy or allergic conjunctivitis. The particular dosages are also selected based on a number of factors including the age, sex, species and condition of the subject. Effective amounts can also be extrapolated from dose-response curves derived from in vitro test systems or from animal models, or clinical trials, such as disclosed herein.

The therapeutically effective amount or an effective amount refers to an amount of cyclodextrin which is sufficient to eliminate or reduce a symptom of eye allergy, such as manifested as allergic conjunctivitis; sequester, bind, reduce and/or inhibit an eye allergen; sequester, bind, reduce and/or inhibit toxic aldehydes or reaction products thereof associated with eye allergic reactions; and/or treat an inflammatory condition associated with eye allergy or allergic conjunctivitis. In some embodiments, the effective amount is a therapeutically effective amount sufficient for the treatment or prevention of eye allergy or allergic conjunctivitis. "Treatment" in this context refers to reducing, ameliorating or mitigating one or more symptom of eye allergy or allergic conjunctivitis. "Prevention" or "prophylactic treatment" in this context refers to a reduction in the frequency of, or a delay in the onset of, symptoms associated with eye allergy or allergic conjunctivitis, relative to a subject who does not receive the composition. The effective amount of cyclodextrin or derivatives thereof, and optionally other active agents in the composition, will depend on absorption, inactivation, and retention/excretion rates of the cyclodextrin as well as the delivery rate of the cyclodextrin into the target tissue or organ (e.g., eye).

Particular dosages may also vary with the severity of the condition to be alleviated. It is to be further understood that for any particular subject, specific dosage regimens can be adjusted over time according to the subject's need and the professional judgment of the person administering or supervising the administration of the cyclodextrin compositions. Generally, a dosing regimen is determined using techniques known to one skilled in the art.

In some embodiments, the cyclodextrin composition is administered as needed, for example based on guidance from a medical professional skilled in the art and/or as assessed by the patient. In some embodiments, the cyclodextrin composition is administered at least once per week. In some embodiments, the cyclodextrin composition is administered at least once every two days. In some embodiments, the cyclodextrin composition is administered at least once per day. In some embodiments, the cyclodextrin composition is administered at least twice per day, at least three times per day, at least four times per day, at least five times per day, or at least six times per day.

For topical ophthalmic administration, each administration comprises one or more aliquots of the composition (e.g., ophthalmic solution). Each aliquot can be a defined volume, for example about 10 µL to about 100 µL about 20 µL to about 80 µL, or about 30 µL to about 60 µL. In some embodiments, each aliquot is about 10 µL, about 20 µL, about 30 µL, about 40 µL, about 50 µL, about 60 µL, about 70 µL, about 80 µL, about 90 µL, or about 100 µL. In some embodiments, the aliquot administered in an estimated volume, for example an applied drop using a dropper or a squeeze vial. In some embodiments, one or more drops, at least two drops, at least three drops, at least 4 drops, at least 5 drops, or at least 6 drops are topically applied to an eye or to each of both eyes at each administration. In some embodiments, each administration comprises sequential administration, for example, a first administration of one or more aliquots (e.g., one or more drops), a first time period for allowing absorption of the composition, followed by a second administration of one or more aliquots (e.g., one or more drops).

Generally, for topical administration the cyclodextrin solution is allowed to remain in contact with the eye for a therapeutically effective time period. In some embodiments, the composition is allowed to remain in contact with the eye for at least about 0.1 min, 0.2 min 0.25 min, 0.3 min, 0.5 min, 1 min, 1.5 min, 2 min or longer, 5 min or longer, 10 min or longer for example, as determined by the medical professional skilled in the art.

In some embodiments, the treatment duration is for a time resulting in reducing, ameliorating, or mitigating one or more symptoms of eye allergy or allergic conjunctivitis. In some embodiments, the symptoms to be assessed include one or more of: redness in the white of the eye or inner eyelid, the amount of tears, level of itchiness, improvements in vision, and swelling of the eyelid. In some embodiments, the duration of treatment is at least 2 days, at least 3 days, at least 5 days, at least 7 days (i.e., one week), at least 10 days, at least 14 days (i.e., two weeks), at least 17 days, at least 21 days (i.e., three weeks), or at least 28 days (i.e., four weeks) or more. In some embodiments, the treatment duration is one month or more, two months or more, three months or more, or four months or more.

In some embodiments, the duration of treatment is about 2 days to about 4 months, about 7 days (i.e., one week) to about 3 months, about 14 days (i.e., two weeks) to about 2 months, or about 21 days (i.e., three weeks) to about 6 weeks (i.e., 1.5 months).

In some embodiments, as discussed above, the cyclodextrin compositions can be administered prophylactically to a subject previously diagnosed but showing no symptoms of allergic conjunctivitis. In some embodiments, the cyclodextrin compositions can be administered prophylactically to a subject identified or determined to have eye allergies, or suspected of having eye allergies. The prophylactic treatment can follow the dosages and administration schedules used for treating allergic conjunctivitis above. In some embodiments, the cyclodextrin compositions can be administered prophylactically to a subject identified or determined to have seasonal allergic conjunctivitis based on expected pollen count in the environment. In some embodiments, the cyclodextrin compositions can be administered prophylactically to a subject identified or determined to have perennial allergic conjunctivitis based on the nature of environment and types of allergens to be encountered by the subject.

In another aspect, provided herein are compositions of cyclodextrin compounds. Accordingly, the compositions encompass each and every one of the compositions described for use in the methods herein. In some embodiments, the compositions are directed to ophthalmic solutions comprising a cyclodextrin. In some embodiments, the ophthalmic solution comprises a cyclodextrin and one or more of ophthalmic pharmaceutically acceptable additive or excipients, wherein the solution is substantially free of a pharmaceutically active agent capable of forming a complex with the cyclodextrin. In some embodiments, the ophthalmic solution consists essentially of a cyclodextrin and one or more of an ophthalmic pharmaceutically acceptable additive or excipient. In some embodiments, the ophthalmic composition (e.g., solution) has cyclodextrin as the sole or only pharmaceutically active agent.

In some embodiments, the ophthalmic solution comprises a cyclodextrin, a pharmaceutically active agent, and one or more of an ophthalmic pharmaceutically acceptable excipients. In particular, the pharmaceutically active agent is an agent suitable for treatment of eye allergy, such as manifested as allergic conjunctivitis. In some embodiments, the pharmaceutically active agent is selected from a mast cell stabilizer, steroid, antihistamine, non-steroidal anti-inflammatory drug (NSAIDs), and an aldehyde trap compound. In some embodiments, the pharmaceutically active agent is a compound of structural formula (I). As discussed above, the compound of structural formula (I) in an ophthalmic solution is present at least about 0.05% w/v, 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 1.5% w/v, about 2% w/v, about 3% w/v, about 4% w/v, or about 5% w/v. In some embodiments, a therapeutic amount of the compound of structural formula (I) in an ophthalmic solution is present at about 0.05% w/v to about 5% w/v, about 0.1% w/v to about 5% w/v, about 0.2% w/v to about 4% w/v, about 0.3% to about 3% w/v, about 0.4% w/v to about 2% w/v, or about 0.5% w/v to about 1.5% w/v.

In some embodiments of the ophthalmic solution comprising a cyclodextrin and a pharmaceutically active agent, the cyclodextrin is present in excess of the pharmaceutically active agent. As described herein, in some embodiments, the cyclodextrin or derivative thereof is present at least in 1 mole (molar) excess of the amount of the pharmaceutically activity agent which forms inclusion complexes with the cyclodextrin. In some embodiments, the amount of cyclodextrin or derivative thereof relative to the amount of the pharmaceutically activity agent is present at least about 1 mole (molar) excess to about 500 mole (molar) excess, about 1.5 mole (molar) excess to about 100 mole (molar) excess; about 2 mole (molar) excess to about 75 mole (molar) excess; about 5 mole (molar) excess to about 50 mole (molar) excess; about 8 mole (molar) excess to about 40 mole (molar) excess; or about 10 mole (molar) excess to about 30 mole (molar) excess.

In some embodiments, the cyclodextrin or derivative thereof relative to the therapeutic amount of the pharmaceutically activity agent which forms inclusion complexes with cyclodextrin is present at least about 1.5 mole (molar) excess, 2 mole (molar) excess, 3 mole (molar) excess, 4 mole (molar) excess, 5 mole (molar) excess, 6 mole (molar) excess, 7 mole (molar) excess, 8 mole (molar) excess, 9 mole (molar) excess, 10 mole (molar) excess, 15 mole (molar) excess, 20 mole (molar) excess, 30 mole (molar) excess, 40 mole (molar) excess, 50 mole (molar) excess, 75 mole (molar) excess, 100 mole (molar) excess, or 500 mole (molar) excess of the amount of the pharmaceutically activity agent present in the composition.

In some embodiments of the ophthalmic solution, the mole (or molar) ratio of the amount of cyclodextrin or derivative thereof to the amount of the pharmaceutically active agent which forms inclusion complexes with the cyclodextrin is at least about 2:1 to about 500:1, about 2:1 to about 200:1; about 5:1 to about 150:1; about 10:1 to about 100:1; about 15:1 to about 50:1; or about 20:1 to about 40:1.

In some embodiments, the mole (or molar) ratio of the cyclodextrin or derivative thereof to the amount of the pharmaceutically active agent which forms inclusion complexes with the cyclodextrin is at least about 2:1, about 3:1, about 4:1, about 5:1, about 6:1, about 7:1, about 8:1, about 9:1, about 10:1, about 15:1, about 20:1, about 30:1, about 40:1, about 50:1, about 100:1, about 150:1, about 200:1, or about 500:1.

In some embodiments of the ophthalmic solution, each and every one of the embodiments of cyclodextrins described above can be used. In some embodiments, the cyclodextrin is selected from α-cyclodextrin, β-cyclodextrin, γ-cyclodextrin, derivatives thereof, and combinations thereof. In some embodiments, the cyclodextrin or derivative thereof is selected from carboxyalkyl cyclodextrin, hydroxyalkyl cyclodextrin, sulfoalkylether cyclodextrin, alkyl cyclodextrin, and combinations thereof. In some embodiments, the alkyl group in the α-cyclodextrin derivative is methyl, ethyl, propyl, butyl, pentyl, or hexyl.

In some embodiments, the cyclodextrin comprises α-cyclodextrin or a derivative thereof. In some embodiments, the cyclodextrin or derivative thereof is selected from carboxyalkyl-α-cyclodextrin, hydroxyalkyl-α-cyclodextrin, sulfoalkylether-α-cyclodextrin and alkyl-α-cyclodextrin.

In some embodiments, the cyclodextrin comprises β-cyclodextrin or a derivative thereof. In some embodiments, the β-cyclodextrin or derivative thereof is selected from carboxyalkyl-β-cyclodextrin, hydroxyalkyl-β-cyclodextrin, sulfoalkylether-β-cyclodextrin and alkyl-β-cyclodextrin. In some embodiments, the β-cyclodextrin is sulfoalkylether-β-cyclodextrin or hydroxyalkyl-β-cyclodextrin. In some embodiments, the sulfoalkylether-β-cyclodextrin is sulfobutylether-β-cyclodextrin. In some embodiments, the hydroxyalkyl-β-cyclodextrin is hydroxypropyl-β-cyclodextrin.

In some embodiments, the cyclodextrin comprises γ-cyclodextrin or a derivative thereof. In some embodiments, the γ-cyclodextrin or derivative thereof is selected from carboxyalkyl-γ-cyclodextrin, hydroxyalkyl-γ-cyclodextrin, sulfoalkylether-γ-cyclodextrin and alkyl-γ-cyclodextrin. In some embodiments, the γ-cyclodextrin is sulfoalkylether-γ-cyclodextrin or hydroxyalkyl-γ-cyclodextrin. In some embodiments, the sulfoalkylether-γ-cyclodextrin is sulfobutylether-γ-cyclodextrin. In some embodiments, the hydroxyalkyl-γ-cyclodextrin is hydroxypropyl-γ-cyclodextrin.

In some embodiments of the ophthalmic solution, the cyclodextrin is present at about 0.1% to about 30% w/v, about 0.1% to about 25% w/v, about 0.1% to about 20% w/v, about 0.2% to about 15% w/v, about 0.5% to about 10% w/v, about 0.5% to about 7.5% w/v, or about 1% to about 5% w/v. For example, an exemplary cyclodextrin, sulfobutylether-β-cyclodextrin, can be present at about 0.1% to about 30% w/v, about 0.1% to about 25% w/v, about 0.1% to about 20% w/v, about 0.2% to about 15% w/v, about 0.5% to about 10% w/v, about 0.5% to about 7.5% w/v, or about 1% to about 5% w/v. Another exemplary cyclodextrin, hydroxypropyl-β-cyclodextrin, can be present at about 0.1% to about 30% w/v, about 0.1% to about 25% w/v, about 0.1% to about 20% w/v, about 0.2% to about 15% w/v, about 0.5% to about 10% w/v, about 0.5% to about 7.5% w/v, or about 1% to about 5% w/v. In instances where mixtures of cyclodextrins are used, for example mixtures of sulfobutylether-β-cyclodextrin and hydroxypropyl-β-cyclodextrin, the total amount of cyclodextrin can be present at about 0.1% to about 30% w/v, about 0.1% to about 25% w/v, about 0.1% to about 20% w/v, about 0.2% to about 15% w/v, about 0.5% to about 10% w/v, about 0.5% to about 7.5% w/v, or about 1% to about 5% w/v.

In some embodiments of the ophthalmic solution, the cyclodextrin is present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 12% w/v, about 14% w/v, about 16% w/v, about 18% w/v, about 20% w/v, about 25% w/v, or about 30% w/v. For example, an exemplary cyclodextrin, sulfobutylether-β-cyclodextrin, can be present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 12% w/v, about 14% w/v, about 16% w/v, about 18% w/v, about 20% w/v, about 25% w/v, or about 30% w/v. Another exemplary cyclodextrin, hydroxypropyl-β-cyclodextrin, can be present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 12% w/v, about 14% w/v, about 16% w/v, about 18% w/v, about 20% w/v, about 25% w/v, or about 30% w/v. In instances where mixtures of cyclodextrins are used, for example mixtures of sulfobutylether-β-cyclodextrin and hydroxypropyl-β-cyclodextrin, the total amount of cyclodextrin can be present at about 0.1% w/v, about 0.2% w/v, about 0.5% w/v, about 1% w/v, about 2% w/v, about 3% w/v, about 4% w/v, about 5% w/v, about 6% w/v, about 7% w/v, about 8% w/v, about 9% w/v, about 10% w/v, about 12% w/v, about 14% w/v, about 16% w/v, about 18% w/v, about 20% w/v, about 25% w/v, or about 30% w/v.

In some embodiments, the ophthalmic solution comprises one or more ophthalmic pharmaceutically acceptable additive or excipient, as described above. In some embodiments, the one or more ophthalmic pharmaceutically acceptable additive or excipient is selected from a tonicity agent, preservative, buffering agent, wetting agent, viscosity enhancing agent, lubricating agent, chelating agent, and antioxidant. Accordingly, each and every embodiment of the additive or excipient as described above is intended to be within the scope of the ophthalmic solution herein.

In some embodiments, the ophthalmic solution is prepared as a sterile solution. In some embodiments, the ophthalmic solution is substantially free of pyrogen and/or endotoxin.

5.3. Kits

In another aspect, any of the cyclodextrin composition described herein, particularly an ophthalmic solution, can be provided in a kit, for example packaged as either a single dose product, such as a single use vial, or a multi-dose product, such as a multi-use vial. In some embodiments, the single dose product is sterile and all of the composition in the package is intended to be consumed in a single application to one or both eyes of a patient.

In some embodiments, the cyclodextrin composition is a multi-dose product, which is also sterile when packaged. For the multi-dose product, the composition can contain a preservative and/or antimicrobial agent to ensure that the composition will not become contaminated from repeated opening and handling of the container. The standards for the level of antimicrobial activity is specified in reference publications, such as the United States Pharmacopoeia ("USP") and corresponding publications in other countries.

Packaging of the cyclodextrin compositions as single dose product can reduce or eliminate the need for an antimicrobial preservative in the composition, which preservative may cause ocular irritation, particularly in patients suffering from pre-existing ocular irritation. The single dose products can be provided as small volume plastic vials, particularly disposable single use plastic squeeze vials, where the single use vials have a non-resealable snap cap or tear-off cap.

While the cyclodextrin compositions are preferably formulated as ready to use aqueous solutions, i.e., solution which does not require any dilution or preparation before use, alternative formulations are can be used. For example, the cyclodextrin or derivative thereof, optionally prepared with one or more of an ophthalmic pharmaceutically acceptable additives and/or excipients, can be lyophilized or otherwise provided as a dried powder or solid form ready for reconstitution with a solvent, such as sterile water (e.g., deionized or distilled). In some embodiments, the cyclodextrin compositions are pyrogen and/or endotoxin free, as required for marketing approval by the appropriate governmental agency. In various embodiments, the sterile cyclodextrin compositions can be prepared by appropriate sterilization procedures known in the art. In some embodiments, the cyclodextrin or derivative thereof is produced under sterile conditions, and the mixing and packaging is conducted under sterile conditions. In some embodiments, the compositions of may be filter sterilized and filled in vials, including unit dose vials providing sterile unit dose formulations. In some embodiments, the composition and/or agents of the compositions is sterilized by steam, γ-radiation, or by appropriate chemical sterilization procedures.

The present disclosure further provides a pharmaceutical pack or kit comprising one or more containers filled with a liquid or lyophilized cyclodextrin formulation (e.g., a formulation comprising cyclodextrin alone, or in combination with a pharmaceutically active agent as described herein). In some embodiments, the formulation is an aqueous formulation of cyclodextrin. In some embodiments, the cyclodextrin formulation is lyophilized.

In some embodiments, the kit further comprises instructions for use in the treatment of allergic conjunctivitis, as well as side effects and dosage information for one or more routes of administration, in particular as required by an appropriate government agency. While the instructional materials typically comprise written or printed materials, any medium capable of storing such instructions and communicating them to an end user is contemplated. Such media include, but are not limited to electronic storage media (e.g., magnetic discs, tapes, cartridges, chips), optical media (e.g., CD ROM), and the like. Such media may include addresses to internet sites that provide such instructional materials.

5.4. Examples

Example 1: Randomized, Parallel, Single-Center, Double-Masked, Vehicle-Controlled Phase II Study to Evaluate the Activity of NS2 Ophthalmic Solution in Subjects with Allergic Conjunctivitis Using the Conjunctival Allergen Provocation Test (CAPT)

Study Objective.

The primary objective of the study is to evaluate the safety and activity of NS2, i.e., compound of structural formula (I), compared to vehicle in the treatment of moderate to severe allergic conjunctivitis in subjects allergic to grass, ragweed or tree allergens following approximately 2 weeks of treatment using the Conjunctival Allergen Provocation Test (CAPT) model.

Study Rationale.

Direct-instillation ocular models are well established for eliciting allergic responses in experimental and clinical ophthalmology testing (Abelson et al., 1990, *Arch Ophthalmol.* 108(1):84-88; Abelson et al., 2003, *Curr Allergy Asthma Rep.* 3(4):363-368). The conjunctival allergen provocation testing (CAPT) is used for evaluating the activity of ophthalmic anti-allergy medications (Abelson et al., 1998, *Am J Ophthalmol.* 125(6):797-804). It requires a direct instillation of concentrated allergen in a liquid format into the conjunctival sac (Leonardi et al., 1990, *Eye (Lond).* 4(Pt 5):760-764). CAPT has been the preferred method of evaluating ocular allergic response and requires subject specific amounts of allergen to induce ocular allergic response.

In order to determine the concentration of allergen which elicits a moderately severe ocular allergic response, subjects go through both an allergen concentration dose finding visit (titrating CAPT), where progressively more concentrated allergen solutions are instilled into the conjunctival sac until a positive allergic response occurs, and an allergen concentration confirmatory visit (confirmatory CAPT), where the concentration which elicited the positive response in the titrating CAPT is instilled again to verify it is correct. The clinical study endpoints are as follows.

Clinical Study Endpoints—Safety Endpoints: (1) number and severity of local and systemic reactions, and other adverse reactions; (2) vital signs; (3) slit lamp examination; (4) visual acuity; (5) non-contact tonometry; and (6) fundus examination.

Clinical Study Endpoints—Activity Endpoints: (1) between-treatment MCFB difference in ocular itching scores; (2) between-treatment MCFB difference in conjunctival redness scores; (3) between-treatment MCFB difference in lid swelling scores; and (4) between-treatment MCFB difference in ocular tearing.

Clinical Study Endpoints—Exploratory Endpoints: between-treatment MCFB difference in cytokine expression.

Study Design.

This double-blind, vehicle-controlled, randomized, parallel group study allows for testing NS2 versus vehicle in subjects with grass, tree or ragweed-induced allergic conjunctivitis in CAPT model. This study consists of 7 or 8 visits to the clinic (a medical screening visit, a titrating CAPT visit, 1 or 2 confirmatory CAPT visits, a CAPT Onset of Action Visit, and three post-2 week dosing CAPT visits) over approximately 9 weeks.

At the screening visit (Visit 1), subjects will undergo informed consent and provide medical/ocular/concomitant medication histories. A urine pregnancy test is performed on women of childbearing potential. Subjects will participate in ophthalmic examinations (Snellen visual acuity (VA), slit lamp examination (SLE), non-contact IOP tonometry (NCT), and an undilated fundus examination) to ensure they meet initial eligibility criteria. Vital signs and a skin prick test for a panel of test allergens are conducted; results must be positive (a wheal that is 3 mm greater than the negative control) for at least one test allergen to proceed to Visit 2. The investigator will consider the allergic responses during the skin prick test, the medical history, and any interfering environmental allergens in order to assess the allergen that is to be used for all subsequent provocation tests and the subject's ability to continue in the study.

At Visit 2, VA and SLE are performed to ensure the anterior segment of the eye is healthy. Ophthalmic evaluations are conducted, including subject rating of subjective ocular symptoms using the electronic Patient Data Acquisition Tablet (ePDAT™) and staff-assessed grading of conjunctival redness and lid swelling prior to any titrating CAPT procedures. Subjects must have ocular itching scores of 0 and conjunctival redness scores of ≤1 in each eye in order to participate. If they do not, they may be rescheduled to another day. Titrating CAPT involves instilling standardized target allergen extracts into the eye in increasing concentrations over time until a positive reaction is elicited or the maximum dose is reached. Administration of allergen at the lowest concentration into the conjunctival sac of both eyes is deemed as time zero with assessment of the allergic response at 2.5 min (+1 min—itching only), 5 min (+2 min) and 10 min (+2 min) for subject assessed symptoms and staff assessed signs. Inclusion into the study will require CAPT to elicit the following response: ocular itching scores of ≥2 and conjunctival redness scores of >2 in each eye in at least one region (nasal or temporal) at any one time point, not necessarily at the same time point. If the initial CAPT does not elicit a positive response, CAPT is repeated with a higher concentration of allergen every 15 min (+2 min) from the last instillation, until a positive reaction is elicited or the maximum dose is reached. If a positive reaction is not reached even with the highest concentration of allergen, the subject is excluded from the study.

At Visit 3, site staff will update concomitant medications and collect AEs as applicable. Ophthalmic evaluations are conducted (VA, SLE, subject rating of ocular symptoms, and staff grading of conjunctival redness and lid swelling). Subjects must have ocular itching scores of 0 in each eye and conjunctival redness scores of ≤1 in each eye in each region (nasal and temporal) of each eye in order to participate. If they do not, they may be rescheduled to another day. Approximately 10 jut of basal tears is collected from both eyes prior to CAPT for cytokine analysis. CAPT is performed using the same allergen titration that elicited a positive response at Visit 2. A positive reaction for confirmatory CAPT is defined as a symptom score of ≥2 for ocular itching and a score of ≥2 for conjunctival redness in each eye in at least one region (nasal or temporal) of each eye at any one time point, not necessarily at the same time point, and establishes continuing eligibility for the study. If a positive reaction is not achieved at the first 3-4 time points of 2.5 min (+1 min—itching only), 5 min, 10 min, 15 min (+2 min), the subject is asked to return to the site for the next higher concentration at visit 3B in 1 week. If the subject did reach a positive response, then the subject's symptoms and signs are recorded at 30, 60, 90, 120, 150 and 180 min (all +5 min) and basal tear collection is begun at 35 min (+15 min) following CAPT instillation. Once again approximately 10 µL of basal tears is collected from both eyes. Subjects are then asked to return in 2 weeks for Visit 4.

At Visit 3B (if applicable), site staff will update concomitant medications and collect AEs as applicable. Ophthalmic evaluations are conducted (VA, SLE, subject rating of ocular symptoms, and staff grading of conjunctival redness and lid swelling). Subjects must have ocular itching scores of 0 in each eye and conjunctival redness scores of ≤1 in each eye in each region (nasal and temporal) of each eye in order to participate. If they do not, they may be rescheduled to another day. CAPT is performed using the next higher concentration titration than what was used at Visit 3. A positive reaction for confirmatory CAPT is defined as a symptom score of ≥2 for ocular itching and a score of ≥2 for conjunctival redness in each eye in at least one region (nasal or temporal) of each eye at any one time point, not necessarily at the same time point, and establishes continuing eligibility for the study. If a positive reaction is not achieved at the first 3-4 time points of 2.5 min (+1 min—itching only), 5 min, 10 min, 15 min (+2 min) the subject is excluded. If the subject did reach a positive response, then the subject's symptoms and signs are recorded at 30, 60, 90, 120, 150 and 180 min (all +5 min) and basal tear collection is begun at 35 min (+15 min) following CAPT instillation. Once again approximately 10 µL of basal tears is collected from both eyes. Subjects are then asked to return in 1 week for Visit 4.

At Visit 4, site staff will update concomitant medications and collect AEs as applicable. Ophthalmic evaluations are conducted (VA, SLE, subject rating of ocular symptoms, and staff grading of conjunctival redness and lid swelling). Subjects must have ocular itching scores of 0 in each eye and conjunctival redness scores of ≤1 in each eye in each region (nasal and temporal) of each eye in order to participate. If they do not, they may be rescheduled to another day. 30 min prior to the CAPT procedure, clinic staff instills one drop of the randomized treatment into each eye. CAPT is then performed using the concentration titration than what reached the positive response at Visit 3 or 3B. Once the CAPT allergen is instilled, subject assessed symptoms and staff assessed signs are collected at 2.5 (+1 min—itching only), 5, 10, 15 min (+2 min), 30, 60, 90, 120, 150, 180 (+5 min). At the end of the visit, subjects are instructed and dispensed their randomized treatment for 2 weeks of at-home qid dosing and their diary card for recording their dosing, AEs, and concomitant medications. Subjects are scheduled to return for Visit 5 in 2 weeks.

At Visit 5, site staff will update concomitant medications and collect AEs as applicable. Ophthalmic evaluations are conducted (VA, SLE, subject rating of ocular symptoms, and staff grading of conjunctival redness and lid swelling). Approximately 10 µL of basal tears is collected from both eyes for cytokine analysis prior to drug instillation and CAPT. 30 min prior to the CAPT procedure, clinic staff instills one drop of the randomized treatment into each eye. CAPT is then performed using the concentration titration than what reached the positive response at Visit 3 or 3B. Once the CAPT allergen is instilled, subject assessed symptoms and staff assessed signs are collected at 2.5 (+1 min—itching only), 5, 10, 15 min (+2 min), 30, 60, 90, 120, 150, 180 min (+5 min). Following CAPT instillation, tear collection is begun at the 35 min (+15 min) mark, and approximately 10 µL of basal tears is collected from both eyes.

At Visit 6, site staff will update concomitant medications and collect AEs as applicable. Ophthalmic evaluations are conducted (VA, SLE, subject rating of ocular symptoms, and staff grading of conjunctival redness and lid swelling). 30 min prior to the CAPT procedure, clinic staff instills one drop of the randomized treatment into each eye. CAPT is then performed using the concentration titration than what reached the positive response at Visit 3 or 3B. Once the CAPT allergen is instilled, subject assessed symptoms and staff assessed signs are collected at 2.5 (+1 min—itching only), 5, 10, 15 min (+2 min), 30, 60, 90, 120, 150, 180 min (+5 min).

At Visit 7, site staff will update concomitant medications and collect AEs as applicable. Ophthalmic evaluations are conducted (VA, SLE, subject rating of ocular symptoms, and staff grading of conjunctival redness and lid swelling). 30 min prior to the CAPT procedure, clinic staff instills one drop of the randomized treatment into each eye. CAPT is then performed using the concentration titration than what reached the positive response at Visit 3 or 3B. Once the CAPT allergen is instilled, subject assessed symptoms and staff assessed signs are collected at 2.5 (+1 min—itching only), 5, 10, 15 min (+2 min), 30, 60, 90, 120, 150, 180 min (+5 min). A urine pregnancy test is performed on women of childbearing potential. Snellen VA, SLE, NCT, undilated fundus examination, and vital signs are performed to ensure safety prior to exit of study.

Trial Design and Choice of Control Group.

This study is performed as a double-masked, vehicle-controlled, randomized trial, with 2 parallel groups (i.e., NS2 vs NS2 vehicle) in a single center. Both randomization and double-blinding of trial medication are accepted methods to minimize imbalances between treatment groups and/or reducing confounding bias in clinical trials (ICH-E8 Jul. 1997). As allergy studies generally show significant vehicle effects, the inclusion of a vehicle group as reference group is incorporated in the study design to allow for an unbiased estimation of treatment effects of active doses of the study drug. Moreover, because of the variability in the individual clinical responses and the subjective nature of symptom assessments, a randomized-vehicle controlled and double-blind study has been adopted as gold standard in clinical trial practice guidelines to determine the activity of allergy medications, especially for immunotherapy. See Canonica et al., 2009. *Allergy.* 64(Suppl 91):1-59; Bousquet et al., 2011, *Allergy* 66(6):765-774; Brozek et al., 2009, *Allergy* 64(8): 1109-1116; and Canonica et al., 2007, *Allergy* 62(3):317-324).

CAPT is considered a validated, reproducible, consistent model to elicit an allergic response and to test ophthalmic formulations to treat allergic conjunctivitis. In a CAPT study, each subject has to go through the following standard visits: medical screening, a titrating CAPT visit, 1-2 confirmatory CAPT visits, and CAPT treatment visits which could include onset of action, duration of action and prophylactic effect visits. CAPT studies are known for their short, simple and efficient design.

The medical screening visit is designed to ensure the ocular and physical health of the subjects and to ensure all inclusion/exclusion criteria are met. The titrating CAPT visit includes instilling increasing concentrations of allergens into the eye until a moderately severe allergic response is obtained. This is the allergen dose finding phase, as the allergen concentration that will elicit the desired response is subject-specific. The confirmatory CAPT visits are designed to re-test the allergen concentration that elicited the positive response in the titrating CAPT visit to ensure that the positive response previously detected was not due to the cumulative effect of the various doses administered. If the single confirmatory CAPT allergen instillation does not elicit the positive response then subjects can return for another confirmatory CAPT visit and go to the next allergen concentration. If this concentration does not elicit a positive response, then the subject is excluded. CAPT visits are typically separated by at least one week. The confirmatory CAPT visit in this study is also designed to act as a baseline visit so that post treatment comparisons can be made.

Once the optimum allergen concentration is known for each subject, the treatment phase of the study can begin. Onset of action, duration of action, and prophylactic action of the investigational product(s) can be examined through various CAPT study visit designs.

This study is designed to examine onset of action (OOA) at Visit 4 by dosing the subject with the randomized treatment 30 min before CAPT allergen instillation. Subject symptom and sign information is then captured at set time points following allergen instillation to measure the length of time required for the drug to take effect.

This study is also designed to examine the randomized treatment's prophylactic action at Visit 5, 6 and 7 as subjects are self-administering the treatment for approximately 2 weeks, 4-times a day (qid) before returning to the clinic for the final CAPT visits.

All measurements used in this study are standard indices of activity and safety, and are typically used for activity and safety evaluations and are reliable, accurate and relevant.

Subject Population.

Up to 120 subjects are randomized in this study with an equal allocation ratio of 1:1 (i.e., up to 60 subjects for each treatment group).

Inclusion Criteria. Subjects satisfying all the following criteria can be included in the trial: (a) provide written informed consent prior to any study-related procedures; (b) 18 years of age or older and are able to provide written consent; (c) willing and able to follow instructions and can be present for the required study visits for the duration of the study; (d) have staff-graded conjunctival redness in at least one region (nasal or temporal) in each eye at any one time point (not necessarily the same time point) post-CAPT of >2 at Visit 2 and ≥2 at Visit 3 and 3B (if required); for Visit 3 and 3B, this score must be reached by the 15 min time point post-CAPT; (e) have a score for subject-graded ocular itching at any one time point post-CAPT ≥2 at Visits 2, 3 and 3B (if required); for Visit 3 and 3B, this score must be reached by the 15 min time point post-CAPT; (f) have a Snellen BCVA, using corrective lenses if necessary, of at least 20/50 in each eye, with investigator discretion if one eye is amblyopic; (g) confirmed absence of pregnancy according to a negative urine pregnancy test at screening for WOCBP, (h) have at least 2 year history of moderate to severe allergic conjunctivitis; (i) have a positive skin prick test to ragweed, grass and/or tree pollen within one year of Screening Visit (Visit 1); (j) ability to self-administer ophthalmic drops; and (k) ability to avoid any topical or systemic ocular medications during the entire study period.

Exclusion Criteria. Any subject who meets one or more of the following criteria are not included in the trial: (a) subjects must not have an ocular itching score >0 or a conjunctival redness score >1 prior to CAPT in either eye in any region (nasal or temporal) at Visits 2-4; if they do, they may be rescheduled to a subsequent date to continue with the study; however, if they return on the rescheduled date with an ocular itching score >0 in either eye or conjunctival redness score >1 in either eye in any region (nasal or temporal), they are excluded; (b) enrollment in any study of an investigational topical or systemic new drug or device within 30 days or have used an investigational drug or device within 30 days prior to study start/randomization; (c) have history of glaucoma, or IOP over 25 mmHg, at the screening visit or a history of elevated IOP within the past 1 year; (d) have had ocular surgery, including laser procedures, within the past 12 months of Visit 1; (e) have contact lens wear within 14 days prior to Visit 1 or unwilling to discontinue wear during study period; (f) have a known history of alcohol and/or drug abuse; (g) WOCBP who are not using an effective means of contraception or who are pregnant or nursing; (h) use of the following topical ophthalmic medications within 1 month of the screening visit: glaucoma medications, antibiotics, antivirals, or topical cyclosporine; (i) have a history of dry eye syndrome or blepharitis; (j) history of herpes simplex keratitis or herpes zoster keratitis; (k) have a history of uveitis in the past 3 years; (l) have presence of any ocular infection (bacterial, viral or fungal) or active ocular inflammation (e.g. follicular conjunctivitis, allergic conjunctivitis) within 14 days prior to start of study (Visit 1), (m) presence of any chronic ocular degenerative condition or ocular inflammation that, in the opinion of the investigator, is likely to get worse over the course of the study; (n) have a systemic disease or uncontrolled medical condition, which in the opinion of the investigator could interfere with study measurements or subject compliance; this would include, but is not limited to, cancer, alcoholism, drug dependency or abuse, or psychiatric disease; (o) have systemic signs of infection (e.g., fever or current treatment with antibiotics); (p) have history of moderate to severe asthma (a score of greater than GINA 1) or allergy induced asthma to the allergen that are used in CAPT, (q) be an employee of the site that is directly involved in the management, administration, or support of this study or be an immediate family member of the same; (r) required use of any prescription or over-the-counter topical ocular medications during the study (other than randomized study medication); (s) anti IgE (Xolair) treatment within 6 months prior to screening and throughout the study period; (t) use of oral corticosteroids within 30 days of screening (Visit 1) and throughout the study period; use of intranasal or inhaled corticosteroids within 14 days of screening (Visit 1) and throughout the study period; (u) use of tricyclic antidepressants, leukotriene receptor antagonists/synthase inhibitors, MAO inhibitors, or cromones (oral or nasal) with 14 days prior to screening (Visit 1) and throughout the study period; (v) use of antihistamines (ocular, nasal, topical or oral) within 7 days prior to screening (Visit 1) and throughout the study period. Non-medicated artificial tears are allowed up to 72 hours before screening (Visit 1) and throughout the study period; (w) use of anticholinergics or beta blockers within 7 days prior to screening (Visit 1) and throughout the study period; (x) use of any medication not previously specified that impair allergy skin testing or conjunctival allergy provocation testing at the discretion of the investigator; (y) use of any other medications listed in the prohibited/concomitant medication section of this protocol; (z) any known contraindication or hypersensitivities to any agents of the study drug formulation; (aa) chronic systemic medications in place for less than one month or a change in the dosage of this medication within the month prior to Visit 1; subjects receiving anti-allergy injections may be enrolled if their dosage has been stable for 3 months prior to Screening and no changes are planned during the study period; and (bb) have a diagnosis of moderate to severe Pinguecula or Pterygia (particularly if it results in chronic erythema), Stevens-Johnson syndrome, ocular cicatricial pemphigoid, mucous membrane pemphigoid, significant conjunctival scarring, chemical burn, herpetic or neurotrophic keratitis, CAPS (Cryopyrin associated periodic syndrome), or keratoconus.

Subject Withdrawal. Subjects can leave the study at any time for any reason without any disadvantageous consequences for his/her subsequent medical care. The investigator can decide to withdraw a subject from the study for urgent medical reasons. A subject may prematurely discontinue the study for any of the following reasons: (a) lack of compliance of the subject to the protocol requirements; (b) withdrawal of consent; (c) judgment by the treating physician(s) that further participation in the study is medically undesirable or not justified; and (d) lost to follow-up. Every effort should be made to perform an early termination visit for subjects who discontinue the study prematurely.

Study Products and Randomization. For study purposes, NS2 0.5% and NS2 0.0% are both referred to as study drug. NS2 is formulated in eye drops for topical ocular use. The drug product is supplied as single dose unpreserved eye drops at an NS2 concentration of 0.5% (w/v). The formulation is 9.5% sulfobutylether-β-cyclodextrin (SBE-β-CD) in sterile water for injection buffered with sodium phosphate, dibasic and monobasic, and pH adjusted to 7.3.

NS2 0.0% vehicle is supplied as single dose unpreserved eye drops at an NS2 concentration of 0.0% (w/v). The formulation is 9.5% SBE-β-CD in sterile water for injection buffered with sodium phosphate, dibasic and monobasic, and pH adjusted to 7.3.

A sealed "patient pack" containing either the drug NS2 0.5% or vehicle control NS2 0.0% is provided to each subject based on a randomization procedure. The investigator, study staff and study subject are masked with respect to the contents of the package. The Group 1 packs will contain 16 foil pouches and 2 foil pouches, each containing 1 card of 4 single use NS2 0.5% vials. The Group 2 packs will contain 16 foil pouches and 2 foil pouches, each containing 1 card of 4 single use NS2 0.0% vials. The subject pack is labeled with: (a) protocol number, (b) sponsor's name and address, (c) Investigational New Drug statement; (d) subject's initials and study ID number; and (e) instructions for use and storage.

Randomization and Masking. Subjects who gave written informed consent are assigned a unique screening subject number. Screening subject numbers are assigned sequentially in ascending order. Subjects who have met all inclusion criteria and none of the exclusion criteria is randomly assigned to one of the two study arms: treatment arm or vehicle control arm (1:1). A computer-generated list randomization code list is generated, and all randomization numbers are assigned sequentially. IMP numbers are allocated to the subject on the applicable visit using randomization code. Neither subject, monitor, investigator, clinic staff, sponsor will have knowledge of which study arm a subject has been randomized. The randomization team members will work independently of the masked team members.

Dose Administration. NS2 ophthalmic drops (0.5%) or NS2 ophthalmic drops (0.0%) Vehicle are provided as single use blow fill vials. One drop is instilled into each eye four times daily for approximately 17 days.

Study Product Storage. NS2 Ophthalmic Drops (0.5%) and NS2 Ophthalmic Drops (0.0%) Vehicle should be stored refrigerated, 2-8° C., in an upright position.

Treatment Compliance. During the 2 weeks of at-home dosing after randomization, the subjects IMP use is documented daily by the subject in a paper diary. When subject returns onsite for Visit 5, the individual blow fill vials are counted and staff will review the dosing diary card. IMP is re-distributed on Visit 5 and final reconciliation performed on Visit 7. Any days without IMP intake is recorded in the eCRF. In case treatment compliance is less than 80%, the subject is considered a protocol violator.

Study Product Accountability. The IMP may only be used by subjects participating in this study as described in this protocol. Subjects will receive IMP at Visit 4 as indicated in the table in FIG. 2.

Schedule of Procedures. Subjects are instructed to return all unused and used vials to the site at Visit 5, 6, and 7. Subjects will inform the investigator about any loss of vials and the investigator or designee must document this information in the eCRF and should take appropriate actions for replacement. The investigator is asked to collect all the used and unused vials for accountability. The study site must maintain accurate records demonstrating dates and amount of study treatment received, dispensed and accounts of any study treatment accidentally or deliberately destroyed.

If the study is terminated, suspended, discontinued, or completed, the investigator will return the unused vials or destroy the drug as instructed by the sponsor.

Restrictions and Prohibited and Concomitant Treatments.

Once the study has begun, the subjects are instructed to take only the study treatments(s) described in this protocol and any other concomitant medications specifically allowed by the investigator. Aside from these, if the subject takes any other treatment during the study, the investigator records the necessary information and may notify the sponsor, if judged to have a potential effect on study results.

The following medications should not be administered at any time during the study:

| Prohibited Medication | Exclusion Period (with Investigator discretion) |
| --- | --- |
| Anti-IgE antibody (Xolair ®) | 6 months prior to screening and throughout the study period |
| Anti-allergy injections using immunotherapy to any allergen | Screening and throughout study period |
| Chronic systemic medications | No changes within 30 days of screening and throughout the study period |
| Investigational drugs/products | 30 days before screening and throughout the study period |
| Immunotherapy (to grass, tree or ragweed allergen) | Within the past 3 years and throughout the study period |
| Topical ophthalmic medications including glaucoma medications, antibiotics, antivirals, or cyclosporine | 30 days before screening and throughout the study period |
| Oral and intra-articular steroid | 30 days before screening and throughout the study period |
| Intranasal and inhaled corticosteroids | 14 days before screening and throughout the study period |
| Ocular/topical/nasal antihistamines | 7 days before screening visit and throughout the study period |
| Tricyclic antidepressants | 14 days screening and throughout the study period |
| Leukotriene receptor antagonists/synthase inhibitors | 14 days screening and throughout the study period |
| MAO inhibitors | 14 days screening and throughout the study period |

| Prohibited Medication | Exclusion Period (with Investigator discretion) |
| --- | --- |
| Cromones, oral or nasal | 14 days screening and throughout the study period |
| Contact lens wear | 14 days before screening visit and throughout the study period |
| Short-acting or long-acting antihistamines (ocular, nasal or oral) (i.e. Azelastine ®, diphenhydramine, Zyrtec ® (cetirizine HCl), Allegra ® (fexofenadine), Claritin ® (loratadine), Clarinex ® (desloratadine)) | 7 days before screening visit and throughout the study period |
| Anticholinergics or beta blockers | 7 days before screening and throughout the study period |
| Non-medicated artificial tears | 72 hours before screening visit and throughout the study period |
| Decongestants | 48 hours before screening visit and throughout the study |
| Herbal or natural product remedies for allergy symptoms | Throughout the study period |
| Vaccination | 3 days prior to each visit |
| Prescription or OTC topical ocular medications during the study (other than study related medications) | |
| Any medication not listed that impairs allergy skin testing or conjunctival allergen challenges at the discretion of the investigator. | |

The decision to administer a prohibited medication or therapy by the investigator is to be done with the safety of the subject as the primary consideration. There may be prohibited therapies not mentioned above at the discretion of the investigator.

Therapy that is considered necessary for the subject's welfare and will not interfere with the evaluation of the study treatments may be given at the discretion of the investigator. The list of prohibited concomitant medications is not complete, there may be other medications unacceptable because of interference with symptom scoring. This is to be decided at the discretion of the investigator.

Study Visits.

Visit 1 (Medical Screening). The following informed consent and medical screening procedures are performed at Visit 1 for each subject: (a) written informed consent is obtained prior to the implementation of any study procedures (a copy is given to the subject); (b) subject is evaluated based on the inclusion/exclusion criteria; (c) relevant medical and ocular history including concurrent diseases, concomitant medication use, and drug allergies are obtained and evaluated to determine eligibility; (d) demographic data (including age, gender and race/ethnicity) are obtained; (e) skin prick test is done to test for seasonal and perennial allergies including allergy to ragweed, grass, tree pollen, cat dander and house dust mites (if one was not done and documented within 1 year); wheal measurement is recorded; (f) vital signs; (g) ophthalmic examination, which will include visual acuity (VA), tonometry (non-contact tonometry (NCT) or Goldmann), slit lamp examination (SLE), and non-dilated fundus examination; (h) urine is collected for pregnancy tests for female subjects of childbearing potential; (i) investigator considers the allergic responses during the skin prick test, the medical history, and any interfering environmental allergens in order to assess the allergen that is used for all subsequent provocation tests and the subject's ability to continue in the study; and (j) AE collection. Only eligible subjects may be scheduled for Visit 2.

Visit 2 (Titrating CAPT). Visit 2 is to occur within 30 days of Visit 1. The following are performed at Visit 2 for each subject: (a) changes in health and medications is assessed and checked against inclusion/exclusion criteria; (b) AE collection; (c) ocular assessment including VA and SLE; (d) subject rating of ocular tearing and itching using the electronic Patient Data Acquisition Tablet (ePDAT™); subjects must have ocular itching scores of 0 at the start of the visit, otherwise must be rescheduled for another date; (e) staff grading of ocular redness and lid swelling; ocular redness must be graded ≤1 in each eye in each region (nasal or temporal) at the start of the visit, otherwise must be rescheduled for another date; (g) titrating CAPT involves instilling standardized target allergen extracts into the eyes in increasing concentrations over time until a positive reaction is elicited or the maximum dose is reached; administration of allergen at the lowest concentration into the conjunctival sac of both eyes is deemed as time zero with assessment of the allergic response at 2.5 min (+1 min—itching only), 5 min (+2 min) and 10 min (+2 min) for subject assessed symptoms and staff assessed signs; (h) inclusion into the study requires CAPT to elicit the following response: ocular itching scores of ≥2 and conjunctival redness scores of >2 in each eye in at least one region (nasal or temporal) at any one time point, not necessarily at the same time point; (i) if the initial CAPT does not elicit a positive response, CAPT is repeated with a higher concentration of allergen every 15 min (+2 min) from the last instillation, until a positive reaction is elicited or the maximum dose is reached; (j) if a positive reaction is not reached even with the highest concentration of allergen, the subject is excluded from the study; and (k) after ophthalmic assessments are completed, a saline rinse may be given at the clinical site to relive any immediate discomfort caused by the conjunctival provocation procedure.

Visit 3 (Confirmatory CAPT). Visit 3 is to occur 7 days (+4 days) following Visit 2. The following are performed at Visit 3 for each subject: (a) changes in health and medications is assessed and checked against inclusion/exclusion criteria; (b) AE collection; (c) ocular assessment including VA and SLE; (d) subject rating of ocular tearing and itching using the electronic Patient Data Acquisition Tablet (ePDAT™); subjects must have ocular itching scores of 0 at the start of the visit, otherwise must be rescheduled for another date; (f) staff grading of ocular redness and lid swelling; ocular redness must be graded ≤1 in each eye in each region (nasal or temporal) at the start of the visit, otherwise must be rescheduled for another date; (g) approximately 10 μL of basal tears is collected from both eyes prior to CAPT for cytokine analysis; (h) confirmatory CAPT involves instilling the same allergen concentration titration that elicited a positive response at Visit 2; (i) positive reaction for confirmatory CAPT is defined as: ocular itching scores of ≥2 and conjunctival redness scores of ≥2 in each eye in at least one region (nasal or temporal) at any one time point, not necessarily at the same time point, and establishes continuing eligibility in the study; (j) if a positive reaction is not achieved at the first 3-4 time points of 2.5 min (+1 min—itching only), 5 min, 10 min, 15 min (+2 min) the subject is asked to return to the site for the next higher concentration at Visit 3B in approximately 1 week (+4 days); (k) if the subject did reach a positive response, then the subject's symptoms and signs is recorded at 30, 60, 90, 120, 150 and 180 min (all +5 min) and basal tear begun at 35 min (+15 min) following CAPT instillation; approximately 10 μL of basal tears is collected from both eyes; (l) subjects are then asked to return in approximately 2 weeks (+4 days) for Visit 4; and (m) after ophthalmic assessments are completed, a saline rinse may be given at the clinical site to relive any immediate discomfort mediated by the conjunctival provocation procedure.

Visit 3B (Re-Confirmatory CAPT). Visit 3B is to occur 7 days (+4 days) after Visit 3, if required. The following are performed at Visit 3B for each subject: (a) changes in health and medications is assessed and checked against inclusion/exclusion criteria; (b) AE collection; (c) ocular assessment including VA and SLE; (d) subject rating of ocular tearing and itching using the electronic Patient Data Acquisition Tablet (ePDAT™); subjects must have ocular itching scores of 0 at the start of the visit, otherwise must be rescheduled for another date; (e) staff grading of ocular redness and lid swelling; ocular redness must be graded ≤1 in each eye in each region (nasal or temporal) at the start of the visit, otherwise visit must be rescheduled for another date; (f) re-confirmatory CAPT involves instilling the next higher allergen concentration titration than what was used at Visit 3; a positive reaction for re-confirmatory CAPT is defined as: ocular itching scores of ≥2 and conjunctival redness scores of ≥2 in each eye in at least one region (nasal or temporal) at any one time point, not necessarily at the same time point, and establishes continuing eligibility in the study; (g) if a positive reaction is not achieved at the first 3-4 time points of 2.5 min (+1 min—itching only), 5 min, 10 min, 15 min (+2 min) the subject is excluded; (h) if the subject did reach a positive response, then the subject's symptoms and signs are recorded at 30, 60, 90, 120, 150 and 180 min (all +5 min) and basal tear collection is begun at 35 min (+1 5 min) following CAPT instillation; approximately 10 µL of basal tears is collected from both eyes; (i) subjects are then asked to return in approximately 1 week (+4 days) for Visit 4; and (j) after ophthalmic assessments are completed, a saline rinse may be given at the clinical site to relive any immediate discomfort mediated by the conjunctival provocation procedure.

Visit 4 (Onset of Action). Visit 4 is to occur 14 days (+8 days) after Visit 3 or within 7 days (+4 days) of Visit 3B, if applicable. The following are performed at Visit 4 for each subject: (a) changes in health and medications is assessed and checked against inclusion/exclusion criteria; (b) AE collection; (c) ocular assessment including VA and SLE; (d) subject rating of ocular tearing and itching using the electronic Patient Data Acquisition Tablet (ePDAT™); subjects must have ocular itching scores of 0 at the start of the visit, otherwise must be rescheduled for another date; (e) staff grading of ocular redness and lid swelling; ocular redness must be graded ≤1 in each eye in each region (nasal or temporal) at the start of the visit, otherwise must be rescheduled for another date; (f) randomization; (g) 30 min (+5 min) prior to the CAPT procedure, clinic staff instills one drop of the randomized treatment into each eye; (h) CAPT is then performed using the concentration titration than what reached the positive response at Visit 3 or 3B; (i) once the CAPT allergen is instilled, subject assessed symptoms and staff assessed signs are collected at 2.5 (+1 min—itching only), 5, 10, 15 min (+2 min), 30, 60, 90, 120, 150, 180 min (+5 min); (j) at the end of the visit, subjects are instructed and dispensed their randomized treatment for 2 weeks of at-home qid dosing and their diary card for recording their dosing, AEs, and concomitant medications; and (k) subjects are scheduled to return for Visit 5 in 14 days (+1 day).

Visit 5 (Prophylaxis). Visit 5 is to occur 14 days (+1 day) after Visit 4. The following are performed at Visit 5 for each subject: (a) changes in health and medications is assessed and checked against inclusion/exclusion criteria; (b) AE collection; (c) ocular assessment including VA and SLE; (d) subject rating of ocular tearing and itching using the electronic Patient Data Acquisition Tablet (ePDAT™); (e) staff grading of ocular redness and lid swelling; (f) approximately 10 µL of basal tears are collected from both eyes prior to drug instillation and CAPT for cytokine analysis; (g) 30 min (+5 min) prior to the CAPT procedure, clinic staff will instill one drop of the randomized treatment into each eye; (h) CAPT is then performed using the concentration titration than what reached the positive response at Visit 3 or 3B; (i) once the CAPT allergen is instilled, subject assessed symptoms and staff assessed signs are collected at 2.5 (+1 min—itching only), 5, 10, 15 min (+2 min), 30, 60, 90, 120, 150, 180 min (+5 min); (j) following CAPT instillation, basal tear collection is begun at the 35 min (+15 min) mark, where approximately 10 µL of basal tears are collected from both eyes; and (k) subject is to continue qid dosing at-home.

Visit 6 (Prophylaxis). Visit 6 is to occur the day after Visit 5. The following are performed at Visit 6 for each subject: (a) changes in health and medications are assessed and checked against inclusion/exclusion criteria; (b) AE collection; (c) ocular assessment including VA and SLE; (d) subject rating of ocular tearing and itching using the electronic Patient Data Acquisition Tablet (ePDAT™); (e) staff grading of ocular redness and lid swelling; (f) 30 min (+5 min) prior to the CAPT procedure, clinic staff instills one drop of the randomized treatment into each eye; (g) CAPT is then performed using the concentration titration than what reached the positive response at Visit 3 or 3B; (h) once the CAPT allergen is instilled, subject assessed symptoms and staff assessed signs are collected at 2.5 (+1 min—itching only), 5, 10, 15 min (+2 min), 30, 60, 90, 120, 150, 180 min (+5 min); and (i) subject is to continue qid dosing at-home.

Visit 7 (Prophylaxis). Visit 7 is to occur the day after Visit 6. The following are performed at Visit 7 for each subject: (a) changes in health and medications are assessed; (b) AE collection; (c) ocular assessment including VA and SLE; (d) subject rating of ocular tearing and itching using the electronic Patient Data Acquisition Tablet (ePDAT™); (e) staff grading of ocular redness and lid swelling; (f) 30 min (+5 min) prior to the CAPT procedure, clinic staff instills one drop of the randomized treatment into each eye; this is the last dosing; (g) CAPT is then performed using the concentration titration than what reached the positive response at Visit 3 or 3B; (h) once the CAPT allergen is instilled, subject assessed symptoms and staff assessed signs are collected at 2.5 (+1 min—itching only), 5, 10, 15 min (+2 min), 30, 60, 90, 120, 150, 180 min (+5 min); (i) after the last ocular assessments, a urine pregnancy test is performed on women of childbearing potential; and (j) Snellen VA, SLE, NCT, undilated fundus examination and vital signs are performed to ensure safety prior to exit of study.

Study Termination.

The end of the trial is defined as the date of the last visit of the last subject in the study. The trial may be terminated prematurely for any reason and at any time by the study sponsor, the principal investigator, the Institutional Ethics Committee (IEC)/Institutional Review Board (IRB), or Competent Authorities. A decision to prematurely terminate the trial is binding to all investigators of all trial centers. IECs/IRBs and Competent Authorities are informed within 15 days about the reason and time of premature trial termination according to the applicable laws and regulations. After the end of the trial, subjects are treated according to local standard practices.

Study Assessments.

Prior to entry into the study or initiation of any study-related procedures, the subject must have read, signed, and dated the current Institutional Review Board (IRB)-approved version of the informed consent form.

Demographic/Medical History. A complete medical/surgical history is obtained from each subject during Visit 1 as part of the eligibility assessment. Demographic information including date of birth, gender, race, ethnicity, and date of informed consent is recorded.

Concomitant Medications History. All concomitant medications (prescription and over-the-counter) taken at Visit 1 and for 6 months prior to Visit 1 or throughout the course of the study are recorded in the Concomitant Medications page of the eCRF. Information regarding the dates of first and last dose, site of dosing (e.g., OD, OS, OU, systemic), and the reason the concomitant medication is being taken is recorded in the eCRF, where known. When a concomitant medication has been taken at a stable dose for longer than 6 months, an estimation of the start date is considered adequate.

Ophthalmic History and Ophthalmic Intervention History. Clinically relevant ophthalmic history and ophthalmic intervention history are documented and will include any previously diagnosed ophthalmic abnormalities and ocular surgeries, including laser procedures.

Activity Assessments. Activity is assessed by the subject's rating of ocular itching and the staff's grading of conjunctival redness.

Ocular Itching. Itching is rated by the subject on the ePDAT™ using a 0-4 scale with 0.5 increments as shown below.

| Score | Intensity Rating | Description |
| --- | --- | --- |
| 0 | None | None |
| 1 | Trace | Tickling sensation involving one or more corners of the eye |
| 2 | Mild | All over tickling sensation |
| 3 | Moderate | Continuous itching with desire to rub |
| 4 | Severe | Severe itching with irresistible urge to rub |

Ocular Tearing. Tearing is rated by the subject on the ePDAT™ using a 0-3 scale with 0.5 increments as shown below.

| Score | Intensity Rating | Description |
| --- | --- | --- |
| 0 | None | No discomfort |
| 1 | Mild | Eyes feel slightly watery |
| 2 | Moderate | Feel like wiping eyes due to tear buildup, may need to blow nose occasionally |
| 3 | Severe | Tears rolling down cheeks, constantly blinking to clear tears |

Ocular Redness. Trained staff may assess ocular redness in the nasal and temporal conjunctiva separately in both eyes, based on a modified Validated Bulbar Redness™ (VBR) descriptive and photographic scale from 0-4 with 0.5 steps shown below and in FIG. 4.

| Score | Intensity Rating | Description |
| --- | --- | --- |
| 0 | None | Normal quiet eye |
| 1 | Mild | Slightly dilated blood vessels; vessel color pink; can be quadrantal |
| 2 | Moderate | Apparent dilation of blood vessels; vessel color more intense [redder]; involves most of vessel bed |
| 3 | Severe | Numerous and obvious dilated blood vessels; color deep red in absence of chemosis; may be less red or pink in presence of chemosis; not quadrantic |
| 4 | Extremely Severe | Large, numerous dilated blood vessels characterized by unusually severe deep red color, involves the entire vessel bed |

Lid Swelling. Lid swelling is assessed by trained staff for each eye separately and scored on a scale of 0-4.

| Score | Intensity Rating | Description |
| --- | --- | --- |
| 0 | None | None |
| 1 | Mild | Edema in one quadrant of lids |
| 2 | Moderate | Definite alteration in Lid Folds |
| 3 | Severe | Edema to Lash Margin |
| 4 | Extremely Severe | Lid Closure |

Tear Collection. Subjects sit in a reclining chair and lean their head to one side facing the tear collector to allow for tear sample collection. The subject is asked to blink then look away from the tear collector. A small glass capillary tube is placed at the outer canthus to draw up a small sample of tears (approximately 10 μL). A maximum of 5 min is allowed per eye for tear collection. Collections are performed as carefully to avoid reflex tearing, and avoidance of the lid margin and the corneal surface are ensured. Following collection, the collected volume is transferred to a labeled Polymerase Chain Reaction (PCR) tube. The subjects then lean their head on the opposite side to collect tears from the outer canthus of the opposite eye with the same technique using a separate glass capillary tube. Tear samples from both eyes are pooled in the same PCR tube and placed on dry ice and stored as soon as possible in a freezer at −80° C.±10° C. Time between collection of samples and placement in the freezer should not exceed 90 min.

Tears collected are subject to human pro-inflammatory cytokine analysis. Cytokine analysis may include but are not limited to IFN-γ, IL-1β, IL-4, IL-5, IL-6, IL-8, IL-10, IL-12, IL-13 and TNF-alpha.

Safety Assessments.

Vital Signs (VS). Resting blood pressure (Systolic and diastolic blood) and pulse rate are measured with calibrated electronic devices. If any of the subject's measurements are outside of the normal ranges at Visit 1, the investigator will determine, on the basis of medical history, whether the subject can safely participate in the study.

Pregnancy Test. Urine pregnancy tests are performed at screening in females of childbearing potential. If a subject has a positive or inconclusive pregnancy test, the subject will not be enrolled in the study. If a subject becomes pregnant during the course of the study, the subject is withdrawn from the study and followed until the end of the pregnancy.

Ophthalmic Exam. An ophthalmic examination includes standard tests routinely performed in a general eye examination.

Visual acuity is performed using a Snellen eye-chart. Ensuring that the subject is comfortably set at the appropriate distance from the eye chart, the subject will hold the occluder one eye. The subject is asked to read the smallest letters possible without squinting using the opposite eye. This process is repeated for the other eye. Visual acuity is recorded as the smallest line read with no more than 2 errors. Acuity is measured without glasses as well as with glasses for those who need refractive correction.

Intraocular pressure is measured using a Non-Contact Tonometer (NCT). Ensuring that the subject has removed their eye glasses and is comfortably seated, subjects will rest their forehead on the rest to measure the right eye first. The measures are repeated in order to obtain 3 good quality measurements. This is repeated for the left eye. Goldmann Tonometry may be an alternate manner to measure intraocular pressure. If the average IOP >25 mmHg is confirmed by non-contact tonometry at screening, the subject is excluded and advised to follow-up with an ophthalmologist or optometrist.

Undilated fundus evaluation includes observation of the vitreous, retina, macula, blood vessels and the optic nerve to screen for presence of inflammation, disease and risk of glaucoma or retinal detachment and visual loss. Upon assessment of all agents of the posterior segment, an overall fundoscopy finding is evaluated as either normal or abnormal. Subjects are excluded from the study if any clinically significant findings are discovered at Screening Visit 1.

Slit lamp examination includes observations of the lids, tear film, conjunctiva, sclera, cornea, iris, anterior/posterior chamber and lens to screen for presence of disease.

Ocular symptom grading assessments is performed using an Eschenbach 3.5×, 10D illuminated magnifier to evaluate conjunctival redness and lid swelling.

Safety Monitoring and Adverse Events.

Subject Safety Monitoring. The sponsor will designate a Medical Monitor to maintain a close liaison with the investigator and study staff to ensure the clinical investigation follows the approved protocol and the research intent of Good Clinical Practice (GCP). Internal standard operating procedures (SOPs) for compliance with applicable government regulations are also to be applied. This liaison is documented by personal and/or telephone visits prior to study initiation and during the study to enable periodic reviews as well as clarify any questions which may arise during the study. During on-site visits, sponsor study monitors are provided access to all study source documents to ensure the integrity of the data.

Pregnancy: Any female with a confirmed positive pregnancy result during study participation (from the time of study drug administration until the end of the study) are immediately withdrawn from the study. Because of the possibility that the fetus/embryo could have been exposed to the study drug through the parent and for the subject safety, the subject is followed until the end of the pregnancy (including spontaneous or voluntary termination).

If a subject becomes pregnant or suspects that they became pregnant during the study, or within 30 days after the study is complete, they must notify the sponsor. Attempts to contact the subject to inquire about the status and progression of the pregnancy are made at intervals deemed appropriate (e.g., at least every three months) until an outcome of the pregnancy is known. This contact is to be documented.

Adverse Events. An adverse event (AE) is defined as any untoward medical occurrence associated with the use of a drug in humans, whether or not considered drug related. Disease signs, symptoms, and/or laboratory abnormalities already existing prior to the use of the product are not considered AEs after treatment unless they reoccur after the subject has recovered from the pre-existing condition or, in the opinion of the investigator, they represent a clinically significant exacerbation in intensity or frequency. AEs are collected from the time the subject signs the informed consent form until the completion of study. AEs reported prior to dosing are captured and considered non treatment emergent AEs.

A serious adverse event (SAE) is defined as any AE that, in the view of either the investigator or sponsor, results in any of the following outcomes: (a) death; (b) life-threatening AE; (c) in-patient hospitalization or prolongation of existing hospitalization; (d) persistent or significant incapacity or substantial disruption of the ability to conduct normal life functions; and (e) congenital anomaly/birth defect.

Important medical events that may not result in death, be life-threatening, or require hospitalization may be considered a SAE when, based upon appropriate medical judgment, they may jeopardize the subject and may require medical or surgical intervention to prevent one of the outcomes listed in this definition. "Life threatening" AE is any AE that places the subject, in the view of either the investigator or sponsor, at immediate risk of death. It does not include an AE that, had it occurred in a more severe form, might have caused death. "Unexpected AE" is any AE not listed in the investigator brochure or that is not listed at the specificity or severity that has been observed; or, if an investigator brochure is not required or available, is not consistent with the risk information described in the general investigational plan or elsewhere in the current drug application. "Unexpected" as used in this definition, also refers to AEs that are mentioned in the investigator brochure as occurring with a class of drugs or as anticipated from the pharmacological properties of the drug, but are not specifically mentioned as occurring with the particular drug under investigation.

Recording Adverse Events. Recorded are all AEs observed, queried, prompted or volunteered by the subjects (regardless of seriousness or relationship to study treatment) in the appropriate section of the subject's case report form or source documents. All SAEs and any non-serious adverse events or laboratory abnormalities resulting in premature discontinuation are followed until they have resolved, returned to baseline, or are determined to be chronic or stable by the investigator. Other non-serious adverse events should be followed through the end of study.

The following details are recorded for AEs: (a) description of event/symptom; (b) onset date and time of event; (c) end date and time of event.

Maximum severity/intensity is rated as follows: (a) Mild—awareness of symptoms but easily tolerated; (b) Moderate: —discomfort enough to cause interference with usual activity; (c) Severe—incapacitating with inability to work or do usual activity; and (d) Life Threatening.

Action taken with study treatment noted as follows: (a) Dose not changed; (b) Drug interrupted; (c) Drug withdrawn; (d) Not applicable; and (e) Unknown.

Any other action taken (such as concomitant medication, non-drug therapy, both, or none). Outcome of AE is noted as follows: Fatal; Not recovered/not resolved; Recovered/resolved; Recovered/resolved with sequelae; and Unknown.

Causality is noted as follows: (a) Definitely or possibly related applies to those AEs that, after careful medical consideration at the time they are evaluated, are considered by the investigator (or other qualified physician) to have at least a possible relationship to study drug; and (b) Unlikely or not related applies to those AEs that, after careful medical consideration at the time they are evaluated, are considered by the investigator (or other qualified physician) to have no relationship, or an unlikely possibility of a relationship, to study drug.

Reporting Serious Adverse Events: Any SAEs, regardless of causality, are reported to the sponsor or their designated representative within 24 hours of learning of the occurrence. The sponsor Medical Monitor is contacted to discuss significant safety issues or to discuss potential unmasking of a study subject within 24 hours of discovery. A written summary fully documenting the event, in order to permit the sponsor to file a report which satisfies regulatory guidelines, is to follow within three calendar days. The event is also reported to the IEC/IRB in accordance with IEC/IRB reporting requirements.

Follow-up information are communicated the same way, using a new SAE Report Form stating that it is a follow-up to the previously reported SAE and giving the date of the original report. The follow-up information should describe whether the event has resolved or continues, if and how it was treated, and whether the subject continued or withdrew from study participation.

If the SAE was not previously documented in the investigator's Brochure and is thought to be related to study drug, the sponsor or their designee may urgently require further information from the investigator for regulatory authority reporting. The sponsor may need to issue an Investigator Notification to inform all investigators involved in any study with the same drug that this SAE has been reported.

The investigator and study personnel should institute any supplemental investigations of SAEs based on their clinical judgment of likely causative factors. This may include clinical laboratory tests not specified in the protocol, histopathologic examinations, or consultations with specialists. The sponsor or their designee may also request the investigator to conduct supplemental assessments.

The investigator notifies Pharmacovigilance of any death or SAE occurring after a subject has withdrawn from the study when such a death occurs within 30 days of the last dose of study drug and may reasonably be related to the study drug.

Removal of Subjects from Study Due to Adverse Events. Subjects are advised that they are free to withdraw from the study at any time. Over the course of the study, the investigator and/or the sponsor may discontinue participation of any subject from the study in the case of unnecessary risk, adverse drug events, or noncompliance. When a subject withdraws from the study, all safety data normally required at the end of the study are obtained, if possible.

Termination of Study Due to Adverse Events. If, in the opinion of the investigator, sponsor, the IEC/IRB or the competent authorities the incidence and severity of AE(s) outweighs the benefit of continuing the study, the study may be terminated. In the event this course of action is to be pursued, the investigator will make every attempt to communicate with the sponsor prior to the decision to develop a complete plan of action and to assess outcomes.

Statistical Methodology and Analyses.

Statistical Analysis Plan. A detailed Statistical Analysis Plan (SAP), including dictionaries used for coding and software used, is finalised prior to the unblinding of the randomization code. The SAP provides full details of the analyses, the data displays, and the algorithms to be used for data derivations.

The SAP includes the definition of major and minor protocol deviations and the link of major protocol deviations to the analysis sets.

Major and minor protocol deviations are identified by medically trained staff before the trial closure.

Sample Size Calculation. Assuming a vehicle response rate of approximately 20% and an NS2 response rate of 50%, 50 subjects in the vehicle control arm and 50 subjects in the NS2 arm result in a 85% power to detect a difference between the groups at an alpha of 0.05.

Analysis Sets. The Safety set consists of all randomized subjects who received at least one dose of the study drug. The subjects are analyzed according to the randomization treatment group.

The Intent-to-Treat population (ITT) set consists of all randomized subjects who received at least one dose of the randomized treatment and for whom at least one post-baseline measurement for the primary activity endpoint is available. The subjects are included in the treatment group to which they were randomized.

The Per-Protocol population (PP) set consists of all subjects from ITT population excluding those with protocol violations that may substantially affect the results of the primary activity endpoint(s). Potential violations that may result in the exclusion of a subject from the Per-Protocol population include, but are not limited to: (a) informed consent not obtained/signed; (b) not fulfilling all inclusion and none of the exclusion criteria during randomization; (c) not receiving the treatment to which they were randomized; (d) less than 80% treatment compliance; and (e) taking forbidden concomitant medication, which may affect the primary endpoint Statistical Analysis. Data are summarized with respect to demographic and baseline characteristics, efficacy variables and safety variables. Summary statistics includes the mean, the number of observations (N), standard deviation (SD), median, minimum and maximum values for continuous variables and frequencies and percentages for categorical variables. Missing values will not be replaced or imputed, i.e., no interpolation or extrapolation is applied to missing values. Safety data are listed and summarized by treatment.

If not otherwise specified, statistical significance is defined as $p<0.05$ and is 2-sided. Any deviation(s) from the planned statistical analysis are described and fully justified in the amended SAP and/or the final clinical study report as appropriate.

Demographic and Baseline Characteristics. Baseline characteristics of subjects who participated in this study are summarized by treatment group using descriptive statistics. Distributions of these parameters among treatment groups are compared descriptively only. No statistical inference is performed.

Previous and concomitant medications are coded according to the latest available version of the World Health Organization (WHO) drug code and the anatomic therapeutic chemical (ATC) class code. They are summarized by tabulating the number and percentages of subjects having received each treatment.

Safety Analysis. Safety is evaluated via the following parameters: (a) AEs; (b) Vital signs; (c) Slit lamp examination; (d) Visual acuity; (e) Non-contact tonometry; and (f) Fundus examination.

For safety data, descriptive statistics n, mean, median, standard deviation, minimum and maximum are summarized by treatment group for continuous variables. Frequencies and percentages are summarized for categorical variables.

Treatment-emergent AEs (TEAEs) are summarized for all causality AEs and for treatment-related AEs (those with related relationship to study medication and missing).

TEAEs are summarized by body system and preferred term by treatment group. Based on the MedDRA preferred term, each AE is counted only once for a given subject. If the same AE occurred in a subject on multiple occasions, the highest severity and least complementary relationship are assumed. If two or more AEs are reported as a single event, the individual terms are reported as separate AEs. Treatment-emergent AEs are defined as AEs that first occurred or worsened in severity after the first dose of study medication.

Serious AEs are presented in a similar way to AEs. All AEs are listed, along with SAEs and AEs leading to discontinuation.

Non-contact tonometry (NCT) assessment are performed at Screening (Visit 1) and at (End of Study, Visit 7), to measure the Intraocular Pressure (IOP). The collected data (average of 3 readings for each eye) are listed by treatment group, subject and visit Summary statistics of the average of 3 readings for each eye are tabulated for Study Eye, Right and Left eye. Study eye is defined in the SAP.

VA assessment is performed at each visit. Data are listed by treatment group, subject and visit.

Analysis of the Activity Endpoints: The primary analyses of the activity endpoints are carried out in the ITT set. Supportive analyses will also be provided for all activity endpoints in the PP population. The change from baseline for each activity endpoints is derived for each treatment group.

Descriptive statistics of all activity endpoints as well individual data listings will presented by treatment group and/or visit. A comparison of NS2 to placebo is made using an analysis of covariance model with baseline as a covariate.

If applicable model assumptions are checked and when appropriate a log transformation is applied to achieve the normality of the continuous outcomes; otherwise a non-parametric method (e.g., Hodges-Lehmann) is applied.

Detailed descriptions of all analyses are included in the SAP. Study eye is defined in the SAP.

The mean change from baseline to V5, V6 and V7 is derived for the following endpoints: (a) Ocular Itching; (b) Ocular Redness; (c) Lid Swelling; and (d) Ocular Tearing.

Analysis of the Exploratory Endpoint. The change from baseline for Cytokine expression is derived. Cytokines may include but are not limited to IFN-γ, IL-1β, IL-4, IL-5, IL-6, IL-8, IL-10, IL-12, IL-13 and TNF-alpha.

Results and Additional Descriptions of Study.

Cyclodextrin Response in CAPT Model. Cyclodextrin was utilized as vehicle in a Randomized, Parallel, Single-Center, Double-Masked, Vehicle-Controlled Phase II Study to Evaluate the Activity of Study Drug NS2 (i.e., structural formula (I)) Ophthalmic Solution in Subjects with Allergic Conjunctivitis using the Conjunctival Allergen Provocation Test (CAPT). There were initial screening and titrating CAPT visits, followed by confirmatory CAPT visits where the allergen dose which reproducibly causes an ocular allergic reaction was selected. This allergen dose was utilized for the active dosing study phase. A CAPT Onset of Action Visit after a single dose of study drug to each eye on dosing Day 1, Visit 4 (V4), and three post-2 week dosing CAPT visits on active dosing days 14, 15 and 16, V5-7. NS2 and vehicle were dosed 4× daily for 16 days. 100 healthy men and women with at least a 2 year history of allergic conjunctivitis to grass, tree or ragweed pollen were enrolled, randomized 1:1, 50 on NS2 and 50 on vehicle containing cyclodextrin.

Marked reductions were demonstrated for ocular itching, ocular tearing and ocular redness with vehicle after both single, i.e., V4 Day 1, and multiple days dosing, as shown in Table 1. The reductions with vehicle from the baseline pre-dosing CAPT visit scores on both Day 1 and the later study visits were of the magnitude seen in this CAPT model with existing therapies utilized in the treatment of AC. A reduction of approximately 1 point for ocular itch is considered clinically relevant.

TABLE 1

| Ocular Itch | Ocular Tearing | Ocular Redness |
| --- | --- | --- |
| Baseline Peak Score Vehicle 3.08 Points | Baseline Peak Score Vehicle 1.8 Points | Baseline Peak Score Vehicle 4.14 Points |
| Vehicle response V4-7: | Vehicle response V4-7: | Vehicle response V4-7: |
| V4: 0.57-0.93 point reduction | V4: 0.52-0.70 point reduction | V4: 0.96-1.36 point reduction |
| V5: 0.74-1.15 point reduction | V5: 0.78-0.90 point reduction | V5: 0.73-1.15 point reduction |
| V6: 0.46-1.27 point reduction | V6: 0.42-0.96 point reduction | V6: 0.77-1.1 point reduction |
| V7: 0.55-1.28 point reduction | V7: 0.59-1.00 point reduction | V7: 0.64-1.40 point reduction |

Figure 5:
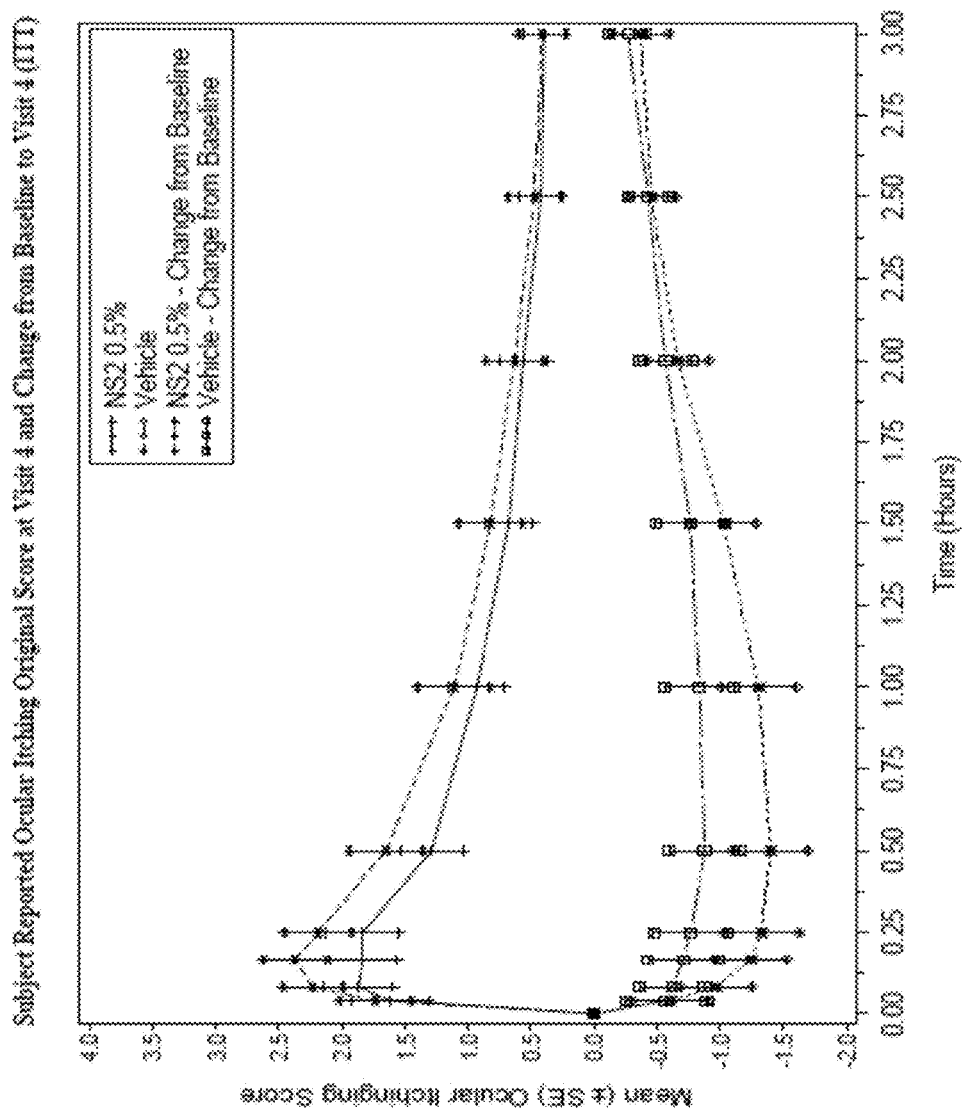
FIG. 5 illustrates the Change from Baseline of Ocular Itching and Ocular Tearing to Visit 4.
Figure 6:
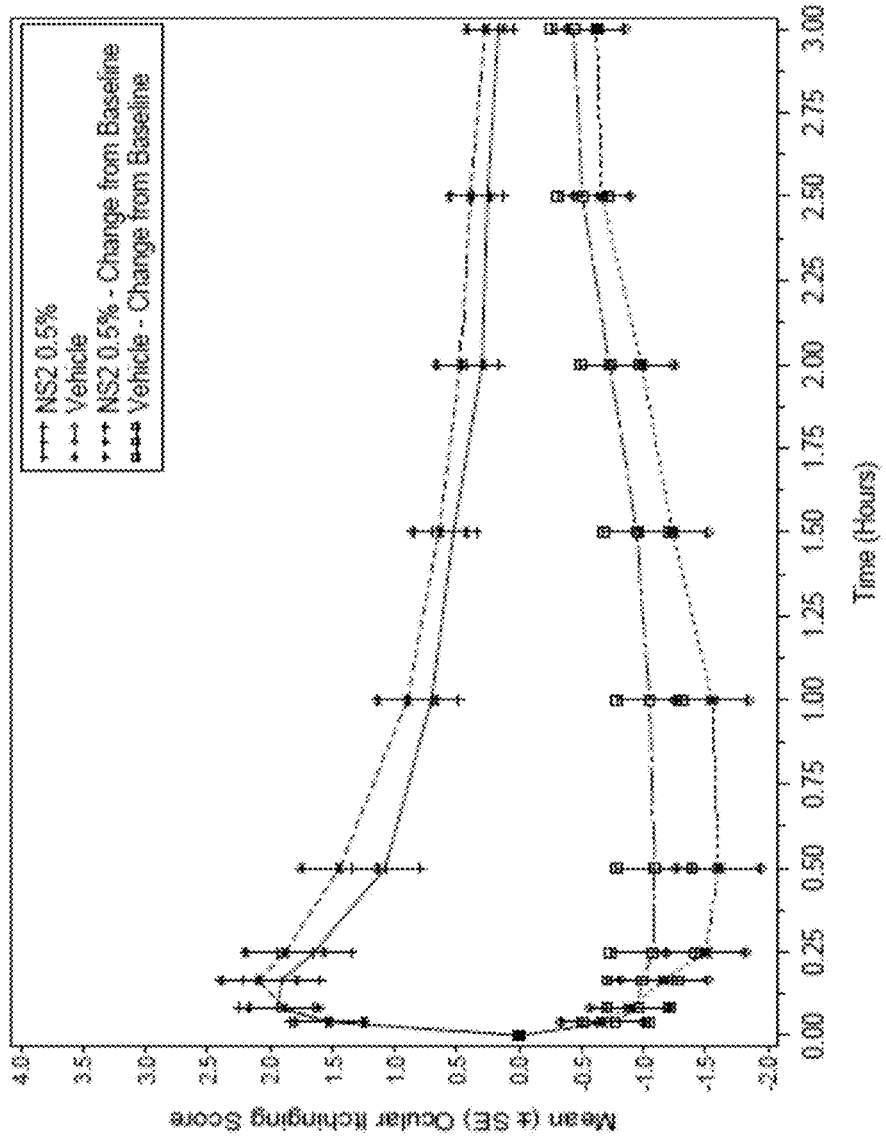
FIG. 6 illustrates the Subject Reported Ocular Itching at Visit 5 and Change From Base Line to Visit 5.
Figure 7:
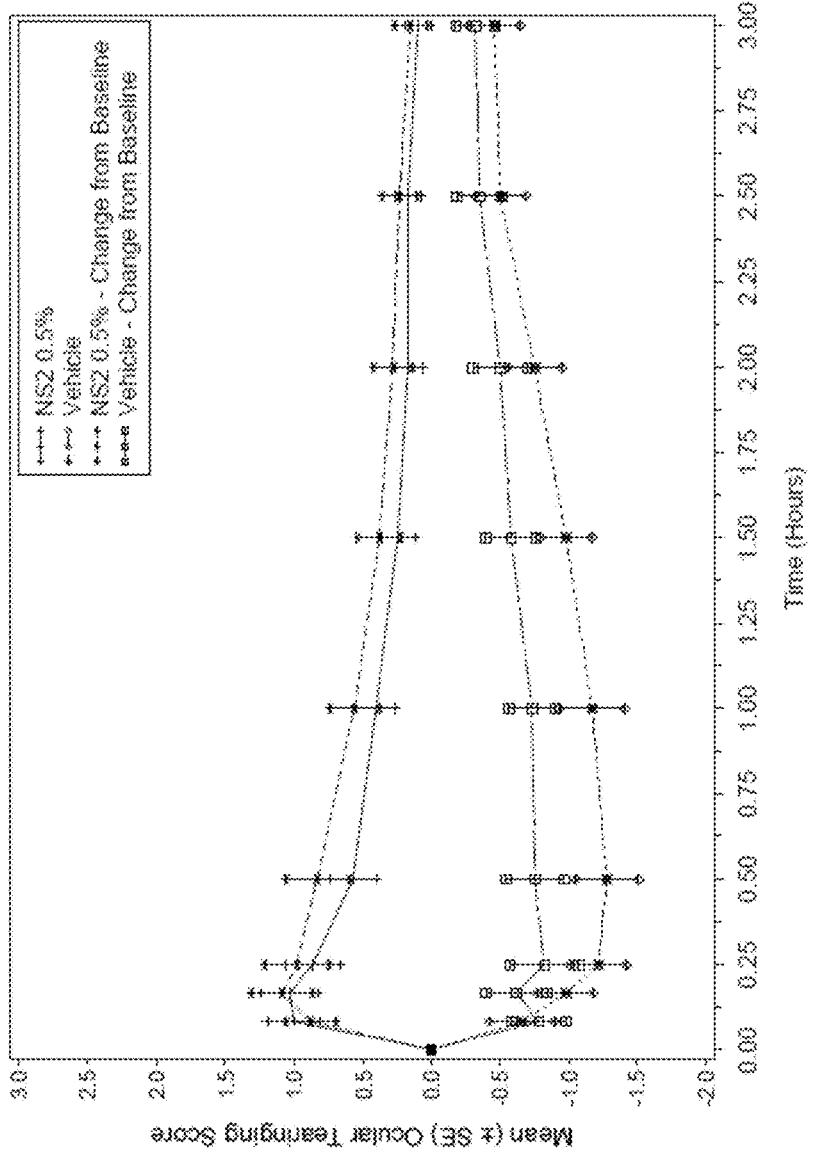
FIG. 7 illustrates the Subject Reported Ocular Tearing at Visit 5 and Change From Base Line to Visit 5.
Figure 8:
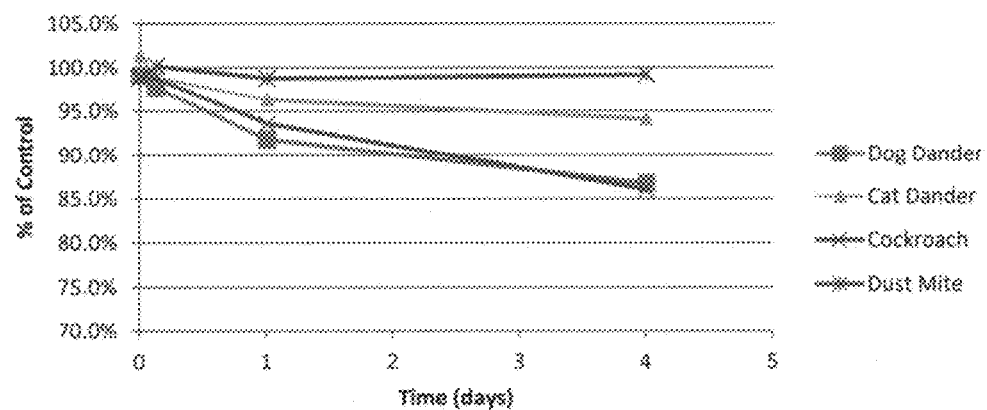
FIG. 8 illustrates the competitive binding of different perennial allergens to sulfobutylether-β-cyclodextrin/NS2 complexes.
Figure 9:
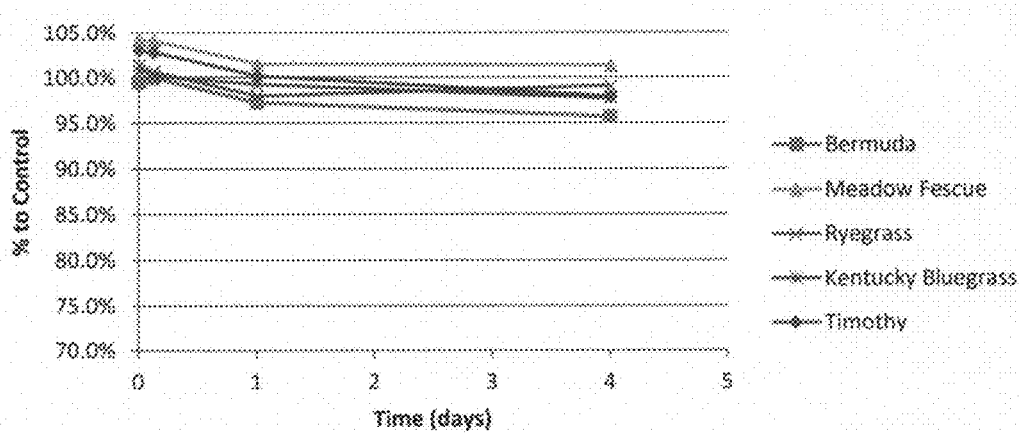
FIG. 9 illustrates the competitive binding of different grass allergens to sulfobutylether-β-cyclodextrin/NS2 complexes.
Figure 10:
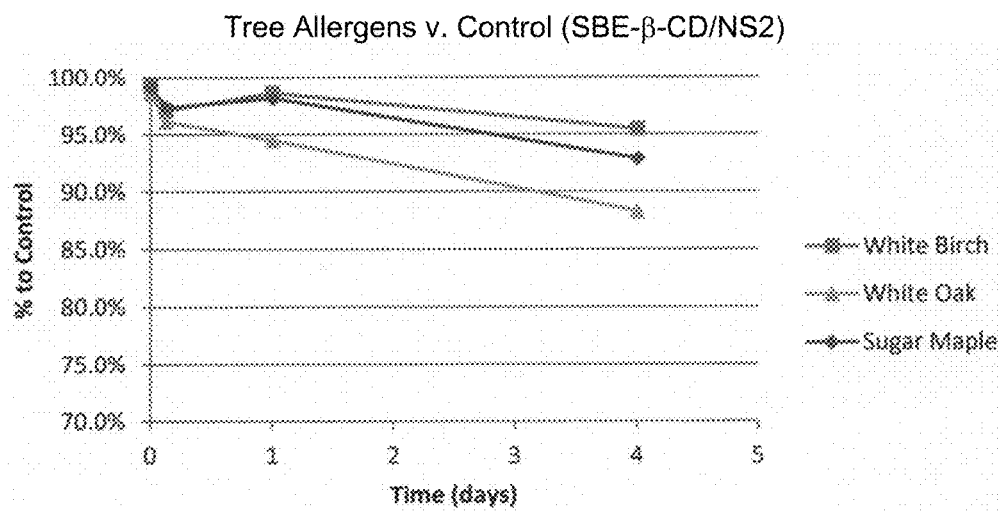
FIG. 10 illustrates the competitive binding of different tree allergens to sulfobutylether-β-cyclodextrin/NS2 complexes.
Figure 11:
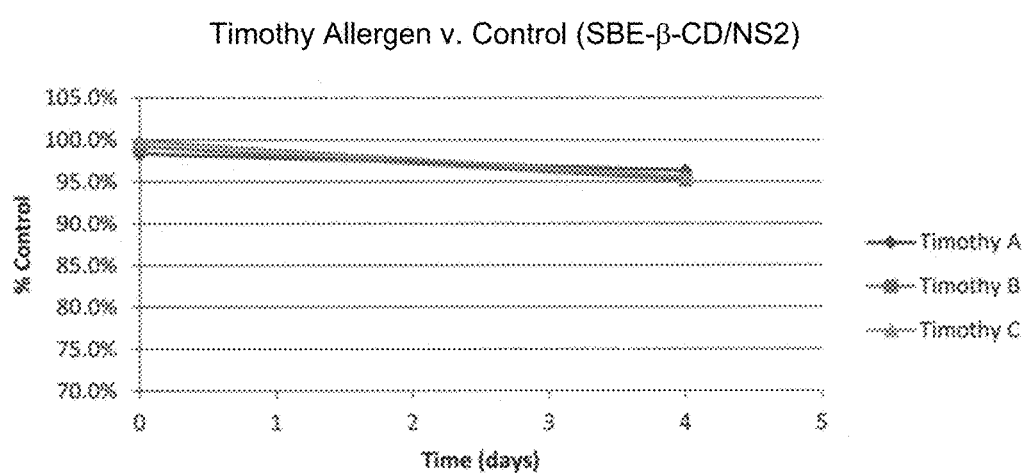
FIG. 11 illustrates the competitive binding of Timothy grass allergen to sulfobutylether-β-cyclodextrin/NS2 complexes.

Results on ocular itching at Visit 4 are shown in FIG. 5. Results on ocular itching and ocular tearing at Visit 5 are shown in FIG. 6 and FIG. 7, respectively.

The statistically significant positive results from the Phase IIa clinical trial of topical ocular NS2 in allergic conjunctivitis demonstrate clinically meaningful effect in allergic conjunctivitis, and the first demonstration of the clinical efficacy of aldehyde trapping in human disease. This suggests that aldehyde trapping could potentially be a novel and important treatment modality for inflammation in general.

Summary of Clinical Trials.

Free aldehydes that are synthesized endogenously are thought to mediate allergic and non-allergic inflammation, both in ocular and non-ocular inflammatory disease. Thus, aldehyde trapping could represent a broad anti-inflammatory approach, and the data lend additional support to this notion. To assess the efficacy of aldehyde trapping in inflammatory disease, two exploratory Phase IIa trials have been initiated in two different forms of ocular inflammation—allergic conjunctivitis and noninfectious anterior uveitis. Ocular inflammation was chosen because the eye is an accessible organ in which biomarkers and clinical signs can be easily and non-invasively measured relatively quickly. In the allergic conjunctivitis trial and the noninfectious anterior uveitis trial, a single dose of drug has been used. The goal of each trial was to demonstrate safety and anti-inflammatory efficacy signals, and there were no primary or secondary efficacy endpoints.

The allergic conjunctivitis Phase IIa trial was a randomized, parallel group, double-masked, vehicle-controlled design evaluating the activity of NS2 ophthalmic solution in subjects with allergic conjunctivitis. The trial utilized the Conjunctival Allergen Provocation Test, known as the CAPT, and was conducted at a single center, Inflamax Research in Ontario, Canada, which has considerable experience with the CAPT model.

NS2 was generally well tolerated in the allergic conjunctivitis population and there were no safety concerns during the study, including vital signs, ocular exam scores, intraocular pressure, and visual acuity. There was an increased frequency of stinging and or burning in the NS2 group. These adverse events were generally mild, with less than 10% reported as moderate, and they were transient, lasting on average only a few minutes after application of the eye drops. These types of adverse events are not uncommon with current therapies and are also not uncommon in patients with allergic conjunctivitis in general, given the hypersensitivity that is characteristic of the disease. There were two subject withdrawals due to stinging in the NS2 group with the other 48 subjects continuing to completion of the 16 day dosing period along with the vehicle patients. There were no serious adverse events.

Because this was a Phase IIa clinical trial, there were no primary or secondary endpoints. It should be noted that the basis for regulatory approval of other eye drops for allergic conjunctivitis is generally patient-reported itching score in CAPT models. In the Phase IIa trial, statistically significant differences were demonstrated between NS2 and vehicle for both ocular itching and ocular tearing patient scores. This was seen after a single dose of NS2 on the Day 1 CAPT challenge and also after 14 days of treatment. These statistically significant differences were evidenced both with comparison at individual time points and by area under the curve analyses by study visit.

There was a consistent pattern of greater effect with NS2 compared to vehicle on itch and tearing following CAPT challenge at all the dosing visits Day 1 through to Day 16. In addition, the clinical efficacy of NS2 was generally sustained throughout the 3 hours studied following each CAPT challenge. Despite a larger than expected vehicle response in the trial, the clinical efficacy of NS2 was generally greater than that of vehicle throughout the entire study.

In terms of clinical significance, the reductions from baseline scores on both Day 1 and the later study visits were of the magnitude seen in the CAPT model with existing allergic conjunctivitis therapies, with peak changes exceeding one point reductions for both ocular itching and ocular tearing scores. The data support the continued development of NS2 in ocular inflammation, and the data continue to be evaluated in conjunction with the anterior uveitis results. Aside from allergic conjunctivitis per se, the data suggest that aldehyde trapping has potential to mitigate inflammation broadly in and outside the eye.

The types of adverse events reported in the clinical trials are not uncommon with current therapies and are also not uncommon in patients with allergic conjunctivitis in general, given the hypersensitivity that is characteristic of the disease. The stinging is not considered to be clinically significant since only 2 patients (4%) of the drug group withdrew from the study during 16 days of dosing four times per day. With regards to the withdrawals, they were in the NS2 group, and 48 out of 50 subjects completing the full 16 days of dosing does not give concern with an allergic conjunctivitis population. One subject withdrew after 1 day of dosing and the other after 2 days. Additionally, anterior uveitis is a different kind of inflammation than allergic conjunctivitis—one that is not characterized by hypersensitivity—and it is expected that the resulting tolerability profile would likely be quite different.

With regards to the better that expected performance of the vehicle group, in trial designs of this nature, when an allergen is present, administration of an aqueous vehicle is expected to have a therapeutic effect and the size of that effect can vary. The fact that NS2 showed such a clear benefit over vehicle in this situation illustrates the magnitude of the clinical activity of NS2.

With regards to any effect on redness, both NS2 and vehicle showed similar improvements in reduction of redness with no pattern of improvement of NS2 vs vehicle. This result is typical in the CAPT model, where demonstration of changes in redness is generally not observed.

The incidence of lid swelling was low in the model with only a minority of subjects having swelling at any stage and so there was no opportunity to evaluate efficacy for this endpoint. The frequency and pattern of lid swelling appeared similar between NS2 and vehicle.

With regard to any insight into what the results of the Uveitis trial might be, the inflammation characteristic of noninfectious anterior uveitis is different from allergy. However, the results from this trial suggest that topical ocular NS2 is well-tolerated and is able to achieve statistically and clinically meaningful changes in efficacy in a form of ocular inflammation.

Discussions of any of the above and any related business of Aldeyra Therapeutics, Inc., as they may be described in the annual report Form 10-K for the year ended Dec. 31, 2014 and quarterly report on Form 10-Q for the quarter ended Sep. 30, 2015, which are on file with the Securities and Exchange Commission (SEC), any other filings with the SEC, including any filings in 2016 and available on the SEC and Aldeyra websites, are incorporated herein by reference in its entirety.

Example 2: Binding of Allergens by Cyclodextrin

The purpose of these experiments was to investigate if NS2 bound to sulfobutylether-β-cyclodextrin (SBE-β-CD) is displaced when incubated with each of twelve different allergen proteins in phosphate buffer at pH 7.0 and 25° C. The experiments tested the interaction of various allergen proteins with the SBE-β-CD/NS2 complex, and the ability of each allergen protein to displace NS2 and render it partially insoluble in the ocular fluid milieu. Time course studies with NS2/SBE-β-CD in each allergen were conducted. The concentration of NS2 was analyzed over a period of 4 days, from T=0 (Day 0) to 96 h (Day 4) after mixing with the allergen protein solution. Each study was conducted using a 19:1 SBE-β-CD/NS2 ratio, at starting concentrations equivalent to the clinical formulation. A 2:1 ratio of protein to NS2 was targeted. The types of allergens and their source are shown in Table 2.

TABLE 2

| Allergens | |
|---|---|
| Grasses | |
| Bermuda Grass | *Cynodon dactylon* |
| Kentucky Blue Grass | *Poa pratensis* |
| Timothy Grass | *Phleum pratense* |
| Ryegrass, Italian | *Lolium perenne* |
| Meadow Fescue | *Festuca pratensis* |
| Trees | |
| White Birch | *Betula populifolia* |
| White Oak | *Quercus Alba* |
| Sugar Maple | *Acer saccharum* |
| Perennials | |
| Cat Dander | *Felis Domesticus* |
| Dog Dander | *Canis familiaris* |
| Cockroach, German | *Blattella germanica* |
| Dust Mite | *Dermatophagoides pteronyssinus* |

Sample Preparation:

Stock solutions of each allergen protein were prepared at a concentration of about 15 mg/mL in 7 mM phosphate buffer, pH 7.2, based on the protein content provided in the label of each lyophilizate, and centrifuged to remove any non-protein, insoluble material originating from the lyophilizate.

Stock solution of NS2 (5.0 mg/mL) and SBE-β-CD (95 mg/mL) was prepared in 7 mM phosphate buffer, pH 7.2. This represents about a 19:1 SBE-β-CD:NS2 ratio in the solution. Working solutions were prepared by mixing 1.2 g of the NS2/SBE-β-CD stock solution with 0.8 g of each of the protein stock solution. These proportions provide a mixture containing approximately 3 mg/g NS2 and 6 mg/g protein (2:1 protein:NS2, w/w). Samples were mix thoroughly by vortexing, and then kept at 25° C. protected from light.

A control solution was prepared using phosphate buffer to dilute the sample to the same NS2 concentration of 3 mg/g. This solution was kept at 25° C., protected from light, alongside the samples containing the allergen proteins.

Sampling:

Test samples were taken at indicated times (T): 0, 3, 24, and 96 h. Each sample was centrifuged and then diluted using 50:50 $H_2O$/Acetonitrile to a concentration measurable by the HPLC method, i.e., to about 0.1 mg/g.

Results and Data Analysis:

All protein-NS2/SBE-β-CD complex mixtures were yellow/brown, clear solutions at T=0. At all other time points, the solutions were visually more cloudy than T=0. Precipitates were visible after centrifugation, only for the samples containing protein. Control solution remained clear, without precipitates. Table 3 and FIG. 8 show results for perennial allergens.

TABLE 3

| Perennial Allergens | | | |
|---|---|---|---|
| Time Point | Protein | mg/g | % to Control |
| T = 0 | Control | 2.90 | — |
| | Dog Dander | 2.88 | 99.1% |
| | Cat Dander | 2.94 | 101.5% |
| | Cockroach | 2.87 | 99.1% |
| | Dust Mite | 2.87 | 98.9% |
| T = 3 hours | Control | 2.90 | — |
| | Dog Dander | 2.84 | 97.7% |
| | Cat Dander | 2.87 | 98.9% |
| | Cockroach | 2.87 | 98.8% |
| | Dust Mite | 2.91 | 100.2% |
| T = 24 hours | Control | 2.91 | — |
| | Dog Dander | 2.67 | 91.8% |
| | Cat Dander | 2.80 | 96.4% |
| | Cockroach | 2.72 | 93.6% |
| | Dust Mite | 2.88 | 98.9% |
| T = 96 hours | Control | 2.94 | — |
| | Dog Dander | 2.55 | 86.7% |
| | Cat Dander | 2.77 | 94.1% |
| | Cockroach | 2.53 | 86.1% |
| | Dust Mite | 2.92 | 99.2% |

Table 4 and FIG. 9 show results for grass allergens.

TABLE 4

| Grass Allergens | | | |
|---|---|---|---|
| Time Point | Protein | mg/g | % to Control |
| T = 0 | Control | 2.95 | — |
| | Bermuda | 2.93 | 99.5% |
| | Meadow Fescue | 3.07 | 104.2% |
| | Ryegrass | 2.97 | 100.7% |
| | Kentucky Bluegrass | 2 99 | 101.4% |
| | Timothy | 3.04 | 103.0% |
| T = 3 hours | Control | 2.93 | — |
| | Bermuda | 2.93 | 100.0% |
| | Meadow Fescue | 3.05 | 104.0% |
| | Ryegrass | 2.95 | 100.6% |

TABLE 4-continued

| Grass Allergens | | | |
|---|---|---|---|
| Time Point | Protein | mg/g | % to Control |
| | Kentucky Bluegrass | 2.94 | 100.2% |
| | Timothy | 3.01 | 102.8% |
| T = 24 hours | Control | 3.01 | — |
| | Bermuda | 2.92 | 97.3% |
| | Meadow Fescue | 3.05 | 101.5% |
| | Ryegrass | 2.95 | 98.0% |
| | Kentucky Bluegrass | 2.99 | 99.3% |
| | Timothy | 3.01 | 100.2% |
| T = 96 hours | Control | 2.98 | — |
| | Bermuda | 2.85 | 95.7% |
| | Meadow Fescue | 3.02 | 101.3% |
| | Ryegrass | 2.95 | 99.1% |
| | Kentucky Bluegrass | 2.91 | 97.8% |
| | Timothy | 2.92 | 97.9% |

Table 5 and FIG. 10 show results for the indicated tree allergens.

TABLE 5

| Tree Allergens | | | |
|---|---|---|---|
| Time Point | Protein | mg/g | % to Control |
| T = 0 | Control | 3.06 | — |
| | White Birch | 3.03 | 99.3% |
| | White Oak | 3.01 | 96.1% |
| | Sugar Maple | 3.03 | 99.2% |
| T = 3 hours | Control | 3.08 | — |
| | White Birch | 2.99 | 97.1% |
| | White Oak | 2.96 | 96.1% |
| | Sugar Maple | 3.00 | 97.3% |
| T = 24 hours | Control | 3.05 | — |
| | White Birch | 2.88 | 98.6% |
| | White Oak | 2.88 | 94.5% |
| | Sugar Maple | 2.99 | 98.1% |
| T = 96 hours | Control | 3.03 | — |
| | White Birch | 2.89 | 95.5% |
| | White Oak | 2.68 | 88.3% |
| | Sugar Maple | 2.82 | 92.9% |

Conclusions

For the study with all allergens, the control solutions in all three groups remained clear, and the concentration of NS2 remained constant. Therefore the change in the solubility of NS2 observed in some of the protein/NS2/SBE-β-CD solutions indicate that certain allergens had an effect in displacing NS2 complexed with SBE-β-CD. This is particularly true for some of the perennial and tree allergens. Specifically, Dog Dander, Cockroach and White Oak had <90% solubility of NS2 after 4 days of incubation. For most of the grass allergens, the proteins showed little to no effect on NS2 solubility relative to the control, even after 4 days of incubation.

Example 3: Study with Timothy Grass Allergen

The interaction of NS2 with Timothy grass allergen was re-tested, using identical parameters as described in Example 2. The lot number of this protein was different from what was tested in the previous study. Time points were taken only at T=0 and T=96 h. The NS2 compound was prepared as in Example 2 in 7 mM sodium phosphate buffer, pH 7.2. Timothy allergen protein was obtained from Greer (Lot No. 243540). Table 6 and FIG. 11 show the results for Timothy allergens.

TABLE 6

| Time Point | Protein | mg/g | % to Control |
|---|---|---|---|
| T = 0 h | Control | 3.07 | — |
| | Timothy A | 3.02 | 98.4% |
| | Timothy B | 3.05 | 99.2% |
| | Timothy C | 3.07 | 99.9% |
| T = 96 h | Control | 3.13 | — |
| | Timothy A | 3.02 | 96.4% |
| | Timothy B | 2.98 | 95.2% |
| | Timothy C | 2.99 | 95.6% |

Conclusions

A moderate decline in NS2 solubility was observed with the Timothy protein, indicating displacement of NS2 complexed with SBE-β-CD by the allergen, consistent with the study in Example 3.

Example 4: Comparison of Allergen Binding to Complexes of NS2 with Sulfobutylether-β-Cyclodextrin and Hydroxypropyl-γ-Cyclodextrin This study examined the displacement of NS2 from its complex with cyclodextrins, sulfobutylether-β-cyclodextrin (SBE-β-CD) and hydroxylpropyl-γ-cyclodextrin (HP-γ-CD), by three different allergen proteins (Birch, Ragweed and Timothy). The goal was to study the interaction between the allergen protein and the cyclodextrins by measuring the effect on NS2 solubility. The concentration of NS2 was analyzed over a period of 5 days, from T0 (Day 0) to 96 hours (Day 4) after mixing with the allergen protein solution.

Study 1 was conducted using a 19:1 SBE-β-CD/NS2 ratio, at starting concentrations equivalent to the clinical formulation. Protein concentration was at 6 mg/mL. A 2:1 ratio of protein to NS2 was targeted. Study 2 was conducted using a 30:1 HP-γ-CD/NS2 ratio, at a starting NS2 concentration similar to Study 1 A 2:1 ratio of protein to NS2 was targeted. Study 3 was conducted at a lower NS2 concentration while using the same allergen protein concentrations, to determine whether the effect was present at the lower concentration. A 19:1 SBE-β-CD/NS2 ratio was still in effect, but the ratio of protein to NS2 was 6:1 due to the lower NS2 concentration.

Study 1.

The experimental parameters used in Study 1 targeted a 2:1 Ratio of Protein to NS2, with a 19:1 ratio of SBE-β-CD to NS2.

TABLE 7

| Materials used in Allergen-NS2-Sulfobutyl Ether Cyclodextrin Study 1<br>Material |
|---|
| 7 mM Sodium Phosphate buffer, pH 7.0 |
| SBE-β-CD |
| NS2 Free Base |
| Birch, European White: allergen per vial |
| 90 mg dry powder, 20.90 mg protein |
| Ragweed, Short: allergen per vial |
| 295 mg dry powder, 72.93 mg protein |
| Timothy: allergen per vial |
| 143.3 mg dry powder, 48.75 mg protein |

Sample Preparation. Stock solutions of each allergen protein were prepared and filtered to remove any non-protein, insoluble portions originating from the lyophilizate.

Each protein solution was prepared at a concentration of about 14 mg/mL in 7 mM Phosphate Buffer, pH 7.3, based on the label claim of protein content in each lyophilizate. Stock solution of NS2 (5.0 mg/mL) and SBE-β-CD (95 mg/mL) was prepared in 7 mM phosphate buffer, pH 7.3. This represents about a 19:1 SBE-β-CD:NS2 ratio in the solution.

Three solutions were prepared where 1.05 mL of the NS2/SBE-β-CD stock solution was mixed with 0.75 mL of each of the protein stock solutions (0.5 mL NS2/SBE-β-CD and 0.36 mL protein for the Birch allergen). These proportions gave a mixture containing approximately 2.95 mg/mL NS2 and 5.8 mg/mL protein (2:1 protein:NS2, w/w). Samples were vortexed to mix thoroughly, then kept at 25° C., protected from light.

A control solution was prepared using phosphate buffer to dilute the sample to the same NS2 concentration of 2.95 mg/mL. This solution was kept at 25° C., protected from light, alongside the samples containing the allergen proteins.

Sampling.

Samples were taken at 3 h, 24 h, and 96 h. Each sample was centrifuged and the supernatant filtered through a PVDF syringe filter. Each filtrate was diluted using 50:50 Water/Acetonitrile to a concentration measurable by the HPLC method, i.e. to about 0.1 mg/mL.

Study 2:

The experimental parameters used in Study 2 targeted a 2:1 Ratio of Protein to NS2, with a 30:1 ratio of HP-γ-CD to NS2 to ensure complete solubility of NS2 at the start of the study.

TABLE 8

| Materials used in Allergen-NS2-Cyclodextrin Study 2<br>Material |
|---|
| 30 mM Sodium Phosphate buffer, pH 7.0 |
| Hydroxypropyl-γ-cyclodextrin (HP-γ-CD) |
| NS2 Free Base |
| Birch, European White: allergen per vial |
| 90 mg dry powder, 20.90 mg protein |
| Ragweed, Short: allergen per vial |
| 295 mg dry powder, 72.93 mg protein |
| Timothy: allergen per vial |
| 143.3 mg dry powder, 48.75 mg protein |

Sample Preparation.

Stock solutions of each allergen protein were prepared and filtered to remove any non-protein, insoluble portions originating from the lyophilizate. Each protein solution was prepared at a concentration of about 14 mg/mL in 30 mM Phosphate Buffer, pH 7.0, based on the label claim of protein content in each lyophilizate. Stock solution of NS2 (5.24 mg/mL) and HP-γ-CD (150 mg/mL) was prepared in 30 mM phosphate buffer, pH 7.0. This represents about a 29:1 HP-γ-CD:NS2 ratio in the solution.

Three solutions were prepared where ~1.3 g of the NS2/HP-γ-CD stock solution was mixed with ~1.0 g of each of the protein stock solutions, to give a mixture containing 2.95 mg/mL NS2 and 6.1 mg/mL protein (2:1 protein:NS2, w/w). Samples were vortexed to mix thoroughly, then kept at 25° C., protected from light.

Sampling.

Samples (~0.5 mL) were taken at T=0 (control), 3 h, 24 h, and 96 h. Each sample was centrifuged and the supernatant filtered through a PVDF syringe filter. Each filtrate was diluted using 50:50 Water/Acetonitrile by serial dilution to a concentration measurable by the HPLC method, i.e. to about 0.1 mg/mL.

Study 3.

The experimental parameters used in Study 3 targeted a 6:1 ratio of Allergen Protein to NS2, due to a lower NS2 concentration, with a 19:1 ratio of SBE-β-CD to NS2. Samples for assay were taken over the course of 5 days (Day 0 to Day 4).

TABLE 9

Materials used in Allergen-NS2-Cyclodextrin Study 3

Material 7 mM Sodium Phosphate buffer, pH 7.0
SBE-β-CD
NS2 Free Base
Birch, European White: allergen per vial
  8.23 mg dry powder, 1.71 mg/g protein
Ragweed, Short: allergen per vial
  30.53 mg dry powder, 7.05 mg protein
Timothy: allergen per vial
  39.23 mg dry powder, 7.89 mg protein Sample Preparation.

Stock solutions of each allergen protein were prepared and centrifuged to remove any non-protein, insoluble portions originating from the lyophilizate. Each protein solution was prepared at a concentration of about 12 mg/mL in 7 mM Phosphate Buffer, pH 7.0, based on the label claim of protein content in each lyophilizate. Stock solution of NS2 (2.0 mg/g) and SBE-β-CD (38.0 mg/g) was prepared in 7 mM phosphate buffer, pH 7.0. This represents about a 19:1 SBE-β-CD:NS2 ratio in the solution.

Three solutions were prepared to give a mixture containing 1.0 mg/g NS2 and 6.0 mg/g protein (6:1 protein:NS2, w/w). Samples were vortexed to mix thoroughly, and then kept at 25° C., protected from light.

A control solution was prepared using phosphate buffer to dilute the sample to the same NS2 concentration of 1.0 mg/mL. This solution was kept at 25° C., protected from light, alongside the samples containing the allergen proteins.

Sampling.

Samples were taken at T=0 (control), 3 h, 24 h, 48 h, and 96 h. Each sample was centrifuged and the supernatant removed. Each sample was diluted using 50:50 Water/Acetonitrile by to a concentration measurable by the HPLC method, i.e. to about 0.1 mg/g.

Results and Data Analysis.

Experimental Observations. In Study 1, there were signs of precipitation in some of the allergen-NS2/SBE-β-CD samples as noted in Table 10 below. The control solution remained clear throughout the study.

TABLE 10

Visual Observations in Study 1

| Time point | Birch | Ragweed | Timothy |
|---|---|---|---|
| 3 hour | Clear | Clear | Clear |
| 24 hour | Clear | Faint Haziness | Cloudiness |
| 48 hour | Clear | Slight Haziness | Moderate Precipitate |
| 96 hour | Clear | Cloudiness | Substantial Precipitate |

In Study 2, the three protein-NS2/HP-γ-CD complex mixtures were yellow, clear solutions at T=0. At T=3 h, 24 h, and 96 h, the solutions were visually unchanged, with no visible precipitates and no hazy appearance either.

In Study 3, the three protein-NS2/SBE-β-CD complex mixtures were yellow, clear solutions at T=0. At T=3 h, 24 h, and 96 h, the solutions were visually more cloudy than T=0. Precipitates were visible after centrifugation, only for the samples containing protein. Control solution remained clear, without precipitates, throughout the solution.

Results of HPLC Analysis.

Each of the samples following centrifugation and filtration to remove precipitate was analyzed by HPLC to determine the content of NS2 remaining in the solution. Results of HPLC analysis for Study 1 are shown in Table 11 and FIG. 12. Target dilution factors were the same for all time points. For the Ragweed sample at 3 hours, for which only the volumes were recorded, the dilution factor was assumed to be the same as for the 24 hour sample, for which the weights were recorded in the dilution.

TABLE 11

HPLC Results and Calculated Recoveries - Study 1.

| Time Point | Protein | mg/mL | % Recovery |
|---|---|---|---|
| Control | N/A | 3.00 | N/A |
| T = 3 hours | Birch | 2.74 | 91.5% |
|  | Ragweed | 2.80 | 93.4% |
|  | Timothy | 2.78 | 92.7% |
| T = 24 hours | Birch | 2.76 | 92.0% |
|  | Ragweed | 2.80 | 93.4% |
|  | Timothy | 2.75 | 91.7% |
| T = 96 hours | Birch | 2.73 | 91.1% |
|  | Ragweed | 2.53 | 84.5% |
|  | Timothy | 2.40 | 80.2% |

Figures 12, 13:
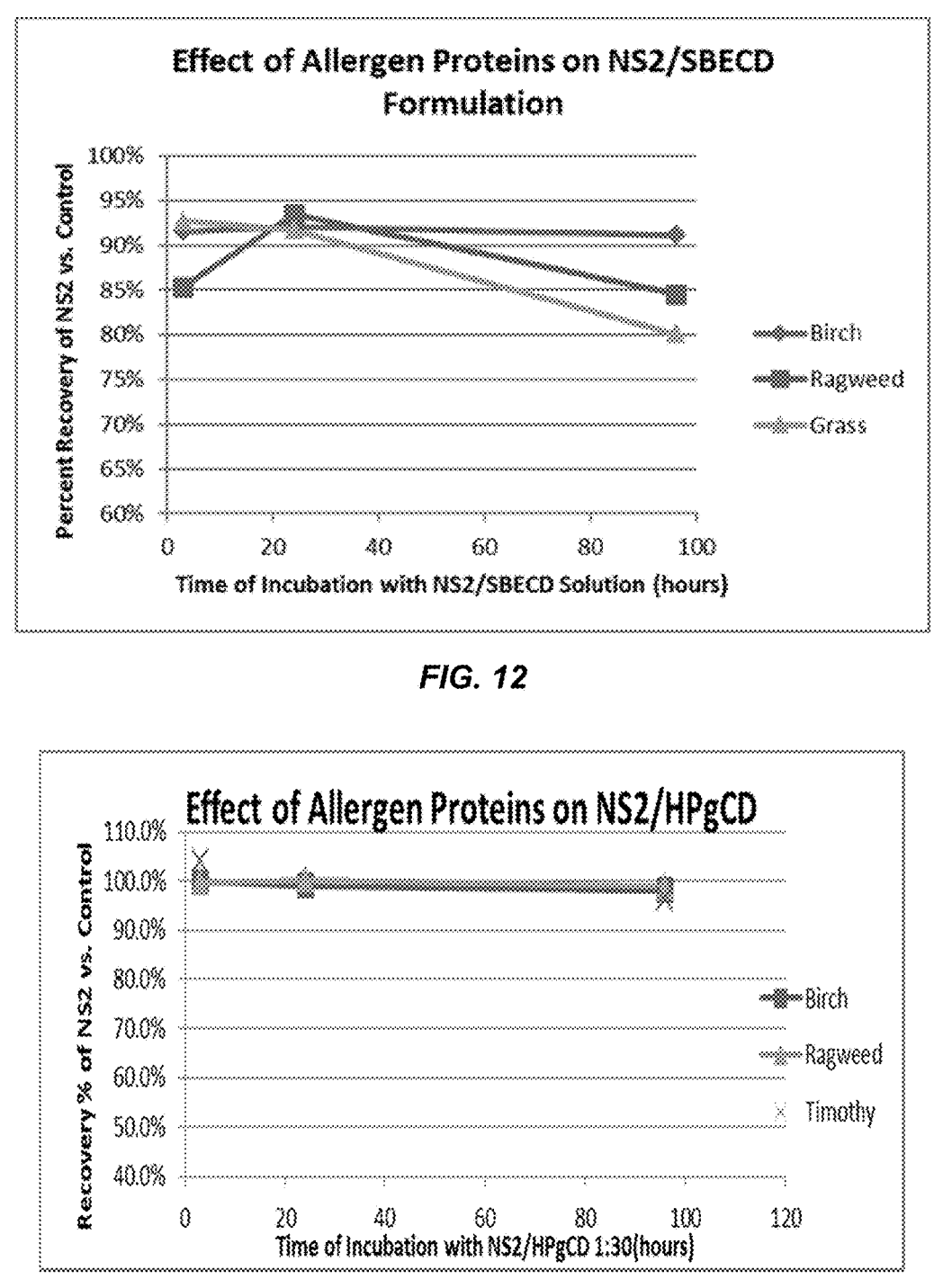

Results of HPLC analysis for Study 2 for time points of NS2 solubility in the presence of excess allergen proteins are shown in Table 12 and FIG. 13. Samples at T=0 were used as controls, then the recovery percentages were calculated based on T=0 control.

TABLE 12

HPLC Results and Calculated Recoveries for Study 2 with HP-γ-CD.

| Time Points | Protein | Calc. Conc., mg/mL | Recovery % |
|---|---|---|---|
| Control T = 0 | Birch | 2.79 | N/A |
|  | Ragweed | 2.78 | N/A |
|  | Timothy | 2.84 | N/A |
| T = 3 h | Birch | 2.78 | 99.9 |
|  | Ragweed | 2.77 | 99.7 |
|  | Timothy | 2.96 | 104.2 |
| T = 24 h | Birch | 2.76 | 99.0 |
|  | Ragweed | 2.79 | 100.3 |
|  | Timothy | 1.33 | 46.9 |
| T = 96 h | Birch | 2.74 | 98.2 |
|  | Ragweed | 2.75 | 98.9 |
|  | Timothy | 2.74 | 96.3 |

When compared to the theoretical NS2 concentration of 2.95 mg/mL, the recovery percentages calculated from the concentrations above were in the range of 93-96%. FIG. 13 charts the percentage recovery of NS2 in the three protein-NS2/HP-γ-CD complex solutions vs. time. For the Timothy-NS2/HP-γ-CD complex solution at T=24 h, the recovery percentage was 46.9%, which appears to be an error from sample preparation or system error, since a subsequent sample from the same solution gave a 96% recovery. Because this time point was an outlier, it was not used in the graph.

The ratio of protein; SBE-β-CD and ratio of protein:NS2 were both higher than in previous studies, and the investigation indicates that these higher ratios result in binding of drug to the PVDF filter. In contrast, previous studies had demonstrated no binding of NS2/SBE-β-CD to the PVDF filter (e.g., PVDF-filtered Control solution for Study 1), and no evidence of binding to the PVDF filters for the NS2/SBE-β-CD/Allergen or NS2/HP-γ-CD/Allergen samples in Studies 1 and 2, where the concentrations were in line with theoretical, at least at early time points.

Figure 14:
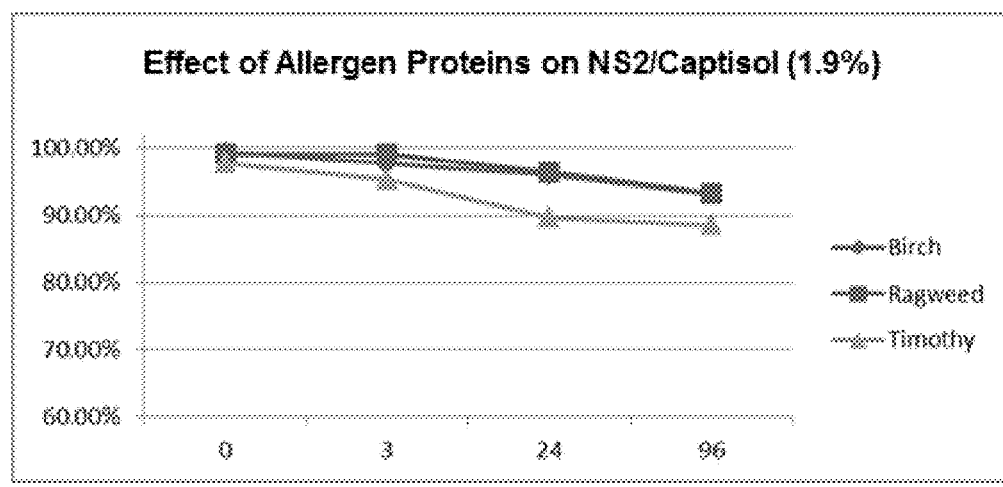
FIG. 14 illustrates the competitive binding of allergens to sulfobutylether-β-cyclodextrin/NS2 complexes, where the ratio of sulfobutylether-β-cyclodextrin:NS2 is 19:1 and the ratio of allergen protein:NS2 is 6:1.

Accordingly, a new set of samples was set up to conduct a repeat of this study, including a control solution (NS2/SBE-β-CD) incubated alongside the allergen protein-NS2-SBE-β-CD samples. For all of these samples, only high-speed centrifugation was used to isolate clear solutions. The results are show in Table 13 and FIG. 14.

TABLE 13

HPLC Results and Calculated Recoveries - Study 3

| Time Points | Protein | mg/g | % to Control |
|---|---|---|---|
| T = 0 | Control | 1.00 | — |
| | Birch | 1.00 | 99.3% |
| | Ragweed | 0.99 | 99.0% |
| | Timothy | 0.98 | 97.8% |
| T = 3 hours | Control | 0.99 | — |
| | Birch | 0.97 | 97.7% |
| | Ragweed | 0.98 | 99.0% |
| | Timothy | 0.94 | 95.3% |
| T = 24 hours | Control | 1.00 | — |
| | Birch | 0.96 | 96.0% |
| | Ragweed | 0.96 | 96.4% |
| | Timothy | 0.89 | 89.7% |
| T = 96 hours | Control | 0.99 | — |
| | Birch | 0.93 | 93.1% |
| | Ragweed | 0.92 | 93.2% |
| | Timothy | 0.87 | 88.6% |

Conclusions

In Study 1, there were clear visual signs, supported by the analytical evaluation of NS2 solubility, that at least some allergen proteins caused displacement of NS2 from the anionically-charged SBE-β-CD cyclodextrin and subsequent precipitation of NS2. This was particularly true for the Timothy and Ragweed allergens, while the Birch allergen had minor effect on NS2 solubility.

Study 2 conducted using HP-γ-CD did not show any significant drops in NS2 solubility, even at 96 hours, and the solutions remained clear. This indicates that there may have been less binding of the allergen proteins to the uncharged HP-γ-CD.

Study 3, which repeated the combination in the first study using lower concentrations of NS2 and SBE-β-CD, showed again a moderate decline in NS2 solubility with some allergen proteins. The Timothy allergen showed the fastest decline, and the Ragweed allergen showed similar results by 96 hours. There was a slight loss of solubility with the Birch allergen. These results confirm that there is an interaction between some allergen proteins, particularly Timothy, and the negatively charged SBE-β-CD cyclodextrin.

All publications, patents, patent applications and other documents cited in this application are hereby incorporated by reference in their entireties for all purposes to the same extent as if each individual publication, patent, patent application or other document were individually indicated to be incorporated by reference for all purposes.

What is claimed is:

1. A method of treating eye allergy, comprising topically administering to an eye of a subject in need thereof a therapeutically effective amount of an ophthalmic composition comprising a cyclodextrin, wherein the composition has cyclodextrin as the sole pharmaceutically active agent.

2. The method of claim 1, wherein the eye allergy is manifested as allergic conjunctivitis.

3. The method of claim 1, wherein the allergic conjunctivitis is seasonal allergic conjunctivitis, perennial allergic conjunctivitis, vernal conjunctivitis, or atopic keratoconjunctivitis.

4. The method of claim 1, wherein the cyclodextrin is selected from α-cyclodextrin, β-cyclodextrin, γ-cyclodextrin, derivatives thereof, and combinations thereof.

5. The method of claim 1, wherein the cyclodextrin comprises β-cyclodextrin or a derivative thereof.

6. The method of claim 5, wherein the β-cyclodextrin or a derivative thereof is carboxyalkyl-β-cyclodextrin, hydroxyalkyl-β-cyclodextrin, sulfoalkylether-β-cyclodextrin, alkyl-β-cyclodextrin, or combinations thereof.

7. The method of claim 5, wherein the β-cyclodextrin is sulfoalkylether-β-cyclodextrin or hydroxyalkyl-β-cyclodextrin.

8. The method of claim 7, wherein the sulfoalkylether-β-cyclodextrin is sulfobutylether-β-cyclodextrin.

9. The method of claim 7, wherein the hydroxyalkyl-β-cyclodextrin is hydroxypropyl-β-cyclodextrin.

10. The method of claim 1, wherein the cyclodextrin is present at about 0.1 to about 30% w/v.

11. The method of claim 1, wherein the cyclodextrin is present at about 0.1 to about 25% w/v.

12. The method of claim 1, wherein the cyclodextrin is present at about 0.1 to about 20% w/v.

13. The method of claim 1, wherein the cyclodextrin is present at about 0.5% to about 10% w/v.

14. The method of claim 1, wherein the composition further comprises one or more of an ophthalmic pharmaceutically acceptable excipient.

15. The method of claim 14, wherein the ophthalmic pharmaceutically acceptable excipient is selected from a tonicity agent, preservative, buffering agent, wetting agent, viscosity enhancing agent, lubricating agent, chelating agent, and antioxidant.

16. A method of preventing or ameliorating onset of symptoms of eye allergy, comprising topically administering to an eye of a subject in need thereof an effective amount of an ophthalmic composition comprising a cyclodextrin, wherein the composition has cyclodextrin as the sole pharmaceutically active agent and wherein the subject has been previously diagnosed with an eye allergy.

17. The method of claim 16, wherein the cyclodextrin is selected from α-cyclodextrin, β-cyclodextrin, γ-cyclodextrin, derivatives thereof, and combinations thereof.

18. The method of claim 17, wherein the cyclodextrin comprises β-cyclodextrin or a derivative thereof.

19. The method of claim 18, wherein the β-cyclodextrin or a derivative thereof is carboxyalkyl-β-cyclodextrin, hydroxyalkyl-β-cyclodextrin, sulfoalkylether-β-cyclodextrin, alkyl-β-cyclodextrin, or combinations thereof.

20. The method of claim 19, wherein the β-cyclodextrin is sulfoalkylether-β-cyclodextrin or hydroxyalkyl-β-cyclodextrin.

21. The method of claim 20, wherein the sulfoalkylether-β-cyclodextrin is sulfobutylether-β-cyclodextrin.

22. The method of claim 20, wherein the hydroxyalkyl-β-cyclodextrin is hydroxypropyl-β-cyclodextrin.

23. The method of claim 16, wherein the cyclodextrin is present at about 0.1 to about 30% w/v.

24. The method of claim 16, wherein the composition further comprises one or more of an ophthalmic pharmaceutically acceptable excipient.

25. The method of claim 24, wherein the ophthalmic pharmaceutically acceptable excipient is selected from a tonicity agent, preservative, buffering agent, wetting agent, viscosity enhancing agent, lubricating agent, chelating agent, and antioxidant.

26. The method of claim 16, wherein the cyclodextrin is present at about 0.1 to about 20% w/v.

27. The method of claim 16, wherein the cyclodextrin is present at about 0.5% to about 10% w/v.

28. The method of claim 1, wherein the composition is administered as needed.

29. The method of claim 1, wherein the composition is administered at least once per day.

30. The method of claim 1, wherein the composition is administered at least two times per day, at least three times per day, at least four times per day, at least five times per day, or at least six times per day.

* * * * *